(12) United States Patent
Hewes et al.

(10) Patent No.: US 11,826,288 B2
(45) Date of Patent: *Nov. 28, 2023

(54) DISPOSABLE KIT

(71) Applicant: Neurasignal, Inc., Los Angeles, CA (US)

(72) Inventors: Henry Hewes, Los Angeles, CA (US); Kevin Lai, Los Angeles, CA (US); Jan Zwierstra, Los Angeles, CA (US); Kiah Lesher, Los Angeles, CA (US); Lane Stith, Los Angeles, CA (US)

(73) Assignee: Neurasignal, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/969,243

(22) Filed: Oct. 19, 2022

(65) Prior Publication Data
US 2023/0116245 A1 Apr. 13, 2023

Related U.S. Application Data

(63) Continuation of application No. 16/698,817, filed on Nov. 27, 2019, now Pat. No. 11,504,290, which is a
(Continued)

(51) Int. Cl.
*A45D 8/36* (2006.01)
*A61B 8/00* (2006.01)
(Continued)

(52) U.S. Cl.
CPC .......... *A61G 13/121* (2013.01); *A45D 8/36* (2013.01); *A61B 8/40* (2013.01); *A61B 8/42* (2013.01);
(Continued)

(58) Field of Classification Search
CPC ............ A61G 13/121; A61G 2210/50; A61B 8/4281; A61B 50/30; A61B 8/40;
(Continued)

(56) References Cited

U.S. PATENT DOCUMENTS 3,992,722 A 11/1976 Rhee
4,058,854 A 11/1977 Rhee
(Continued)

FOREIGN PATENT DOCUMENTS

EP 0 727 651 A1 8/1996
WO WO-2012/092598 A2 7/2012

OTHER PUBLICATIONS

International Preliminary Report on Patentability dated Oct. 15, 2020, from application No. PCT/US2018/044253.
(Continued)

*Primary Examiner* — Tarla R Patel
(74) *Attorney, Agent, or Firm* — Polygon IP, LLP

(57) ABSTRACT

Arrangements described herein relate to systems, apparatuses, and methods for a disposable kit containing medical items configured for a medical device including a head cradle to support a head of a subject, the disposable kit includes a container that encloses a head cradle pad configured to be affixed to the head cradle, at least one fiducial marker configured to be disposed on a location at the head of the subject, and at least one enclosure configured to cover a portion of the medical device.

20 Claims, 37 Drawing Sheets

Related U.S. Application Data continuation of application No. 16/048,209, filed on Jul. 27, 2018, now Pat. No. 10,492,877.

(60) Provisional application No. 62/660,499, filed on Apr. 20, 2018.

(51) Int. Cl.

| | | |
|---|---|---|
| *A61B 46/00* | (2016.01) | |
| *A61B 50/30* | (2016.01) | |
| *A61F 17/00* | (2006.01) | |
| *A61G 13/12* | (2006.01) | |
| *A61B 46/10* | (2016.01) | |
| *B32B 1/00* | (2006.01) | |
| *A61F 13/12* | (2006.01) | |
| *A61F 13/00* | (2006.01) | |
| *A61G 15/12* | (2006.01) | |
| *A61B 34/30* | (2016.01) | |
| *A61B 90/00* | (2016.01) | |
| *A61B 17/00* | (2006.01) | |
| *A61F 5/37* | (2006.01) | |
| *A61N 7/00* | (2006.01) | |
| *A61G 7/07* | (2006.01) | |
| *A61B 50/33* | (2016.01) | |
| *A61B 50/00* | (2016.01) | |
| *A61B 8/08* | (2006.01) | |
| *A61G 5/12* | (2006.01) | |
| *A61B 34/20* | (2016.01) | |

(52) U.S. Cl.
CPC .......... *A61B 8/4209* (2013.01); *A61B 8/4281* (2013.01); *A61B 17/00* (2013.01); *A61B 34/30* (2016.02); *A61B 46/00* (2016.02); *A61B 46/10* (2016.02); *A61B 50/30* (2016.02); *A61B 90/361* (2016.02); *A61F 5/3707* (2013.01); *A61F 13/00072* (2013.01); *A61F 13/12* (2013.01); *A61F 17/00* (2013.01); *A61G 15/125* (2013.01); *A61N 7/00* (2013.01); *B32B 1/00* (2013.01); *A45D 2200/25* (2013.01); *A61B 8/0808* (2013.01); *A61B 8/4218* (2013.01); *A61B 50/33* (2016.02); *A61B 2017/0023* (2013.01); *A61B 2034/2057* (2016.02); *A61B 2050/005* (2016.02); *A61B 2050/0055* (2016.02); *A61B 2050/0056* (2016.02); *A61B 2050/3008* (2016.02); *A61B 2090/3937* (2016.02); *A61G 5/121* (2016.11); *A61G 7/072* (2013.01); *A61G 2203/30* (2013.01); *A61G 2210/50* (2013.01)

(58) Field of Classification Search
CPC . A61B 46/00; A61B 2050/3008; A61B 17/00; A61B 46/10; A61B 34/30; A61B 90/361; A61B 2034/2057; A61B 2050/0055; A61B 2090/3937; A61B 2017/0023; A45D 8/36; A45D 2200/25; A61F 17/00; A61F 5/3707; A61N 7/00
See application file for complete search history.

(56) References Cited

U.S. PATENT DOCUMENTS

| | | |
|---|---|---|
| 6,273,896 B1 | 8/2001 | Franck et al. |
| 6,640,976 B1 | 11/2003 | Franks-Farah et al. |
| 7,450,985 B2 | 11/2008 | Meloy |
| 10,265,234 B1 * | 4/2019 | Zwierstra ............... A61B 34/30 |
| 10,492,877 B2 * | 12/2019 | Hewes ...................... B32B 7/12 |
| 11,504,290 B2 * | 11/2022 | Hewes ...................... B32B 5/18 |
| 2005/0081860 A1 | 4/2005 | Gonzales |
| 2009/0048508 A1 | 2/2009 | Gill et al. |
| 2011/0290262 A1 | 12/2011 | Tomes et al. |
| 2014/0018664 A1 | 1/2014 | Weiss et al. |
| 2018/0250183 A1 | 9/2018 | Zwierstra et al. |
| 2019/0021666 A1 | 1/2019 | Hynynen |

OTHER PUBLICATIONS

Partial International Search Report dated Dec. 7, 2018, from application No. PCT/US2018/044253.
U.S. Corrected Notice of Allowability dated Mar. 21, 2019, from U.S. Appl. No. 16/048,213.
U.S. Non-Final Office Action dated Feb. 25, 2019, from U.S. Appl. No. 16/048,209.
U.S. Non-Final Office Action dated Oct. 29, 2018, from U.S. Appl. No. 16/048,213.
U.S. Notice of Allowance dated Feb. 25, 2019, from U.S. Appl. No. 16/048,213.
U.S. Notice of Allowance dated Jul. 21, 2022, from U.S. Appl. No. 16/698,817.
U.S. Notice of Allowance dated Jul. 22, 2019, from U.S. Appl. No. 16/048,209.

\* cited by examiner

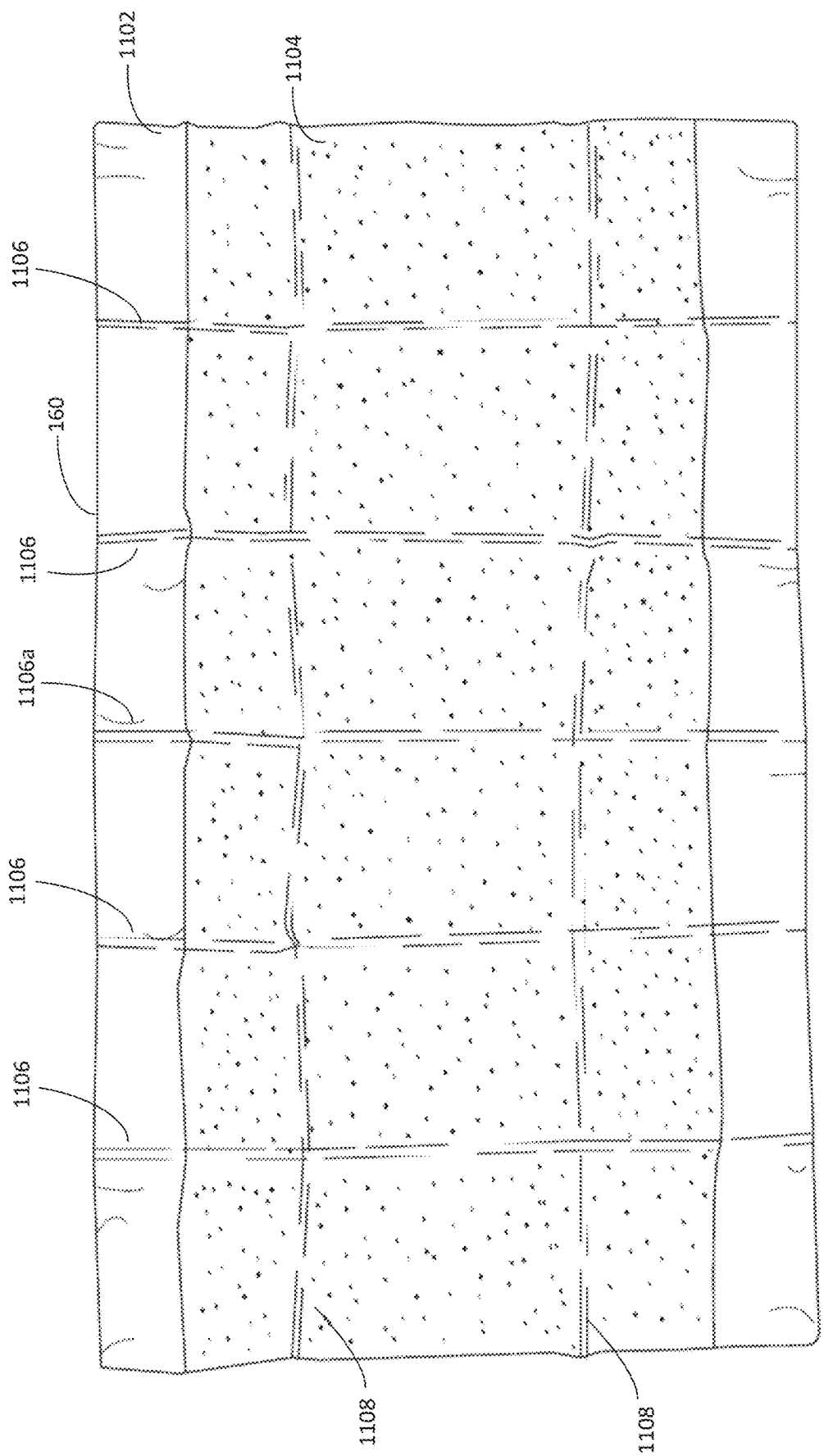

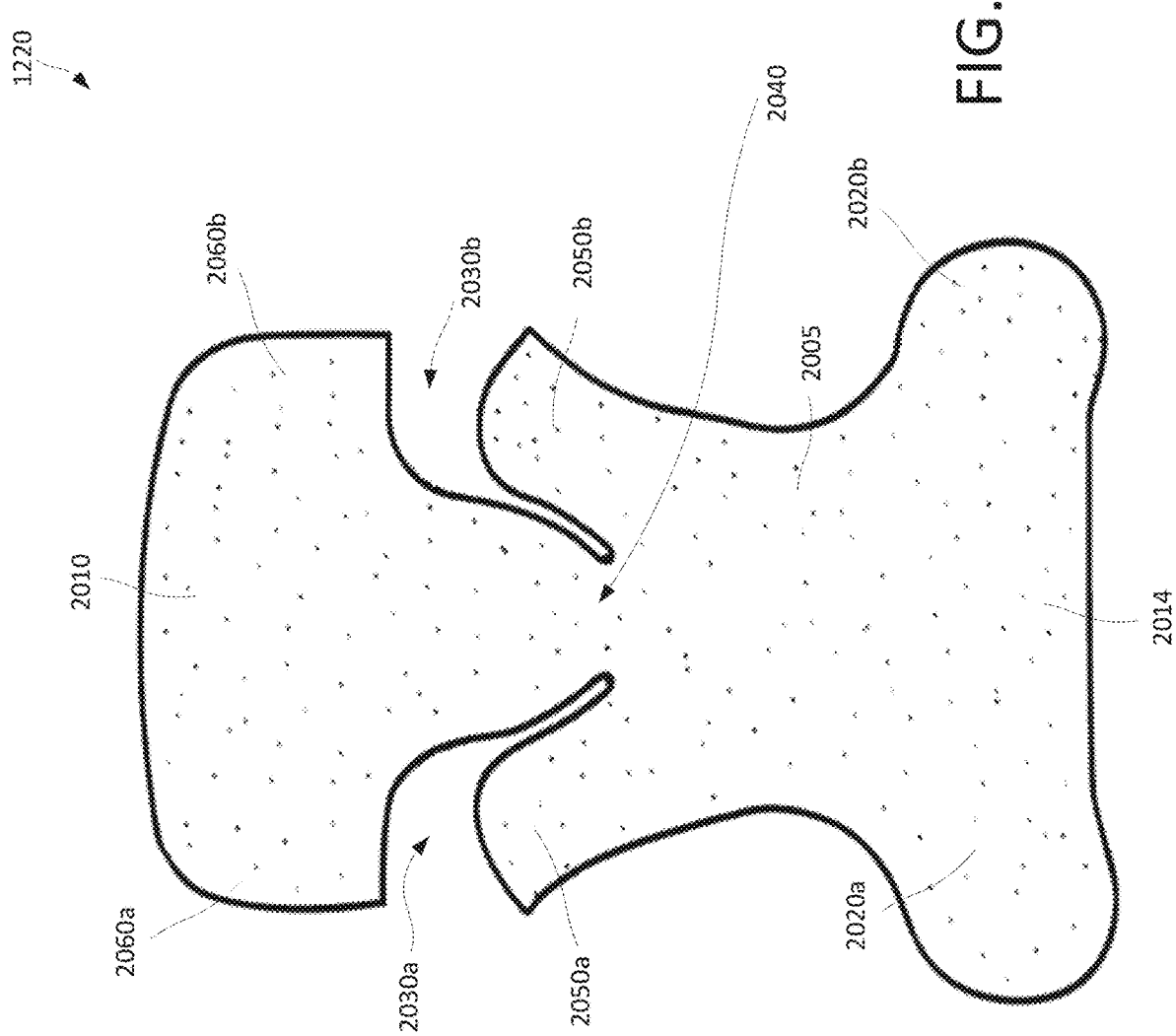

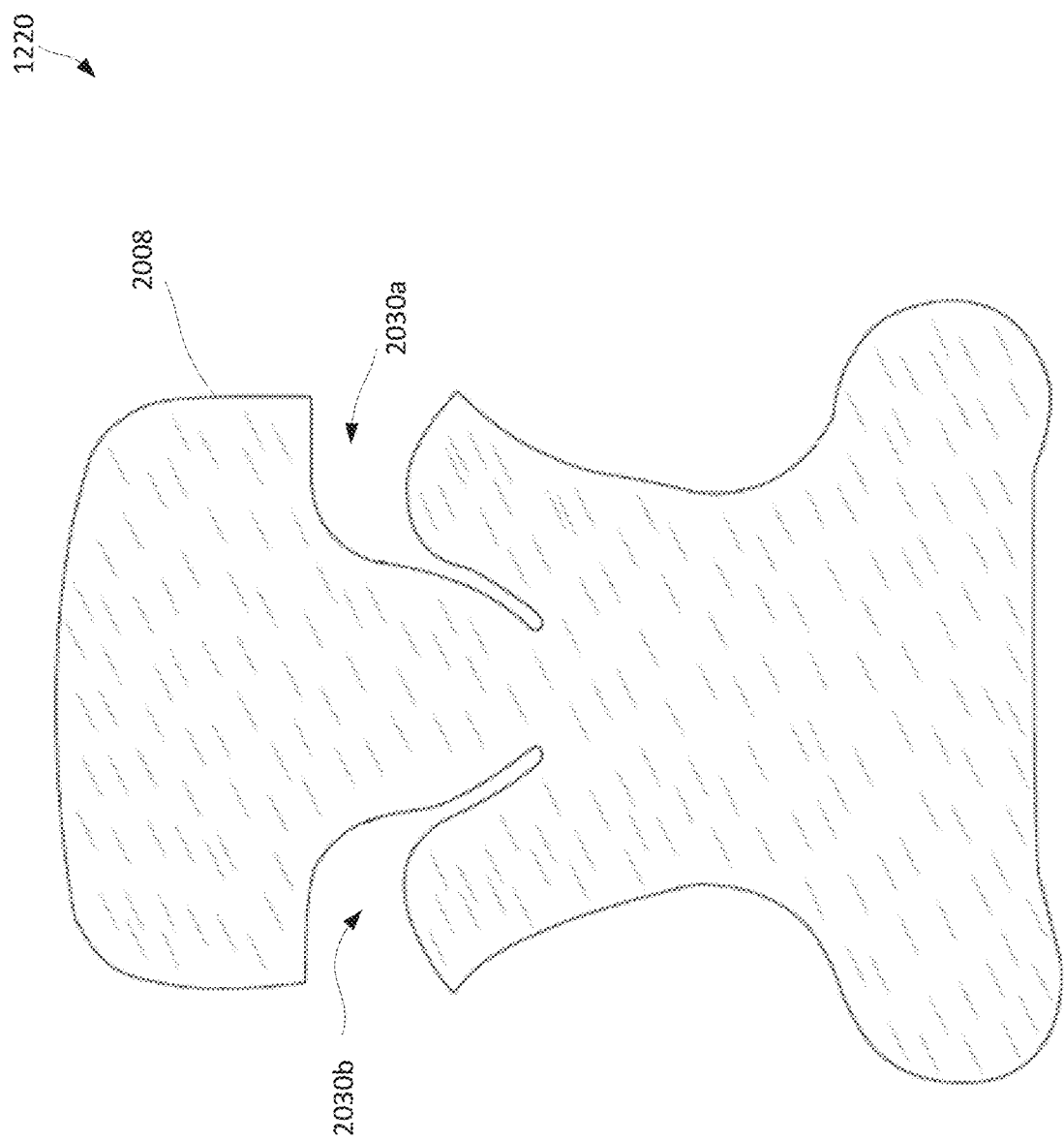

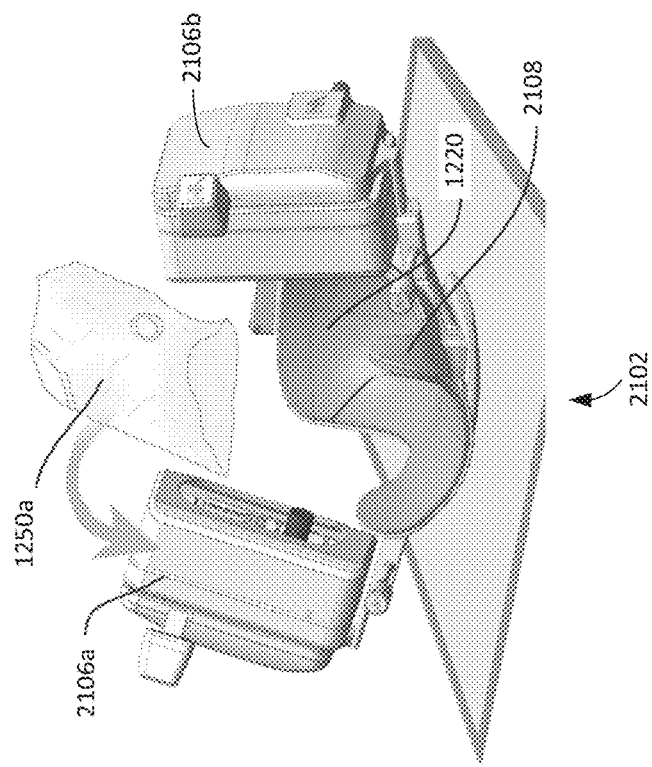
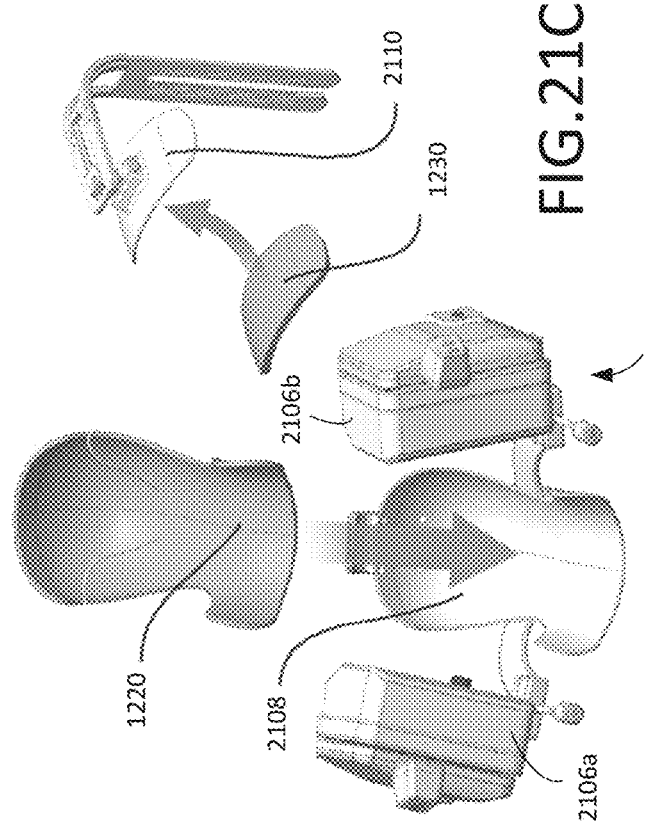
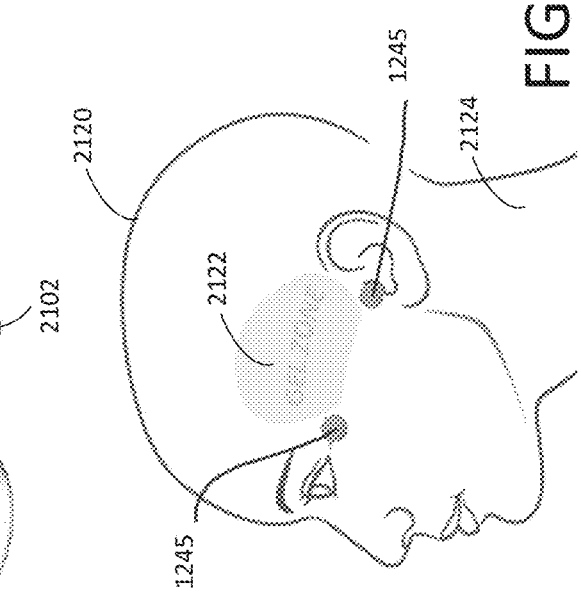

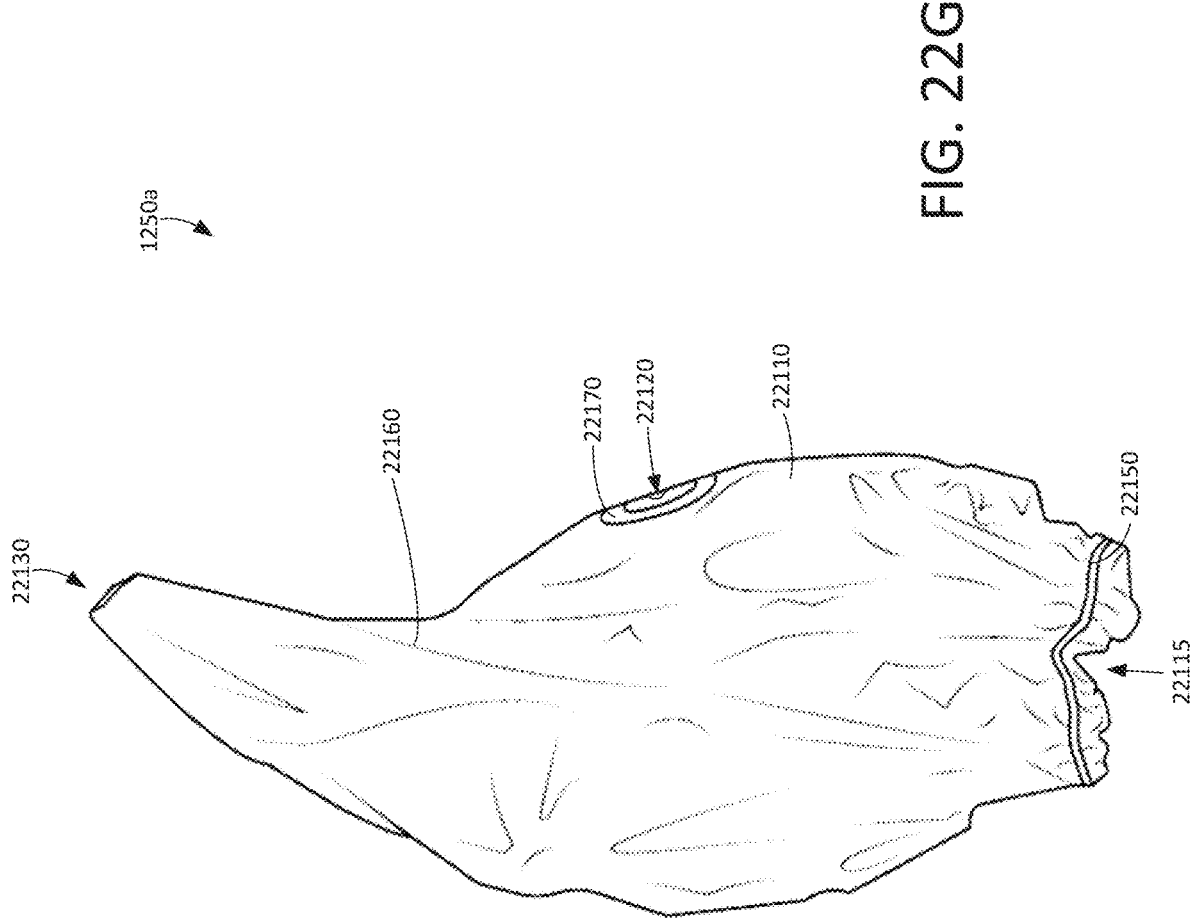

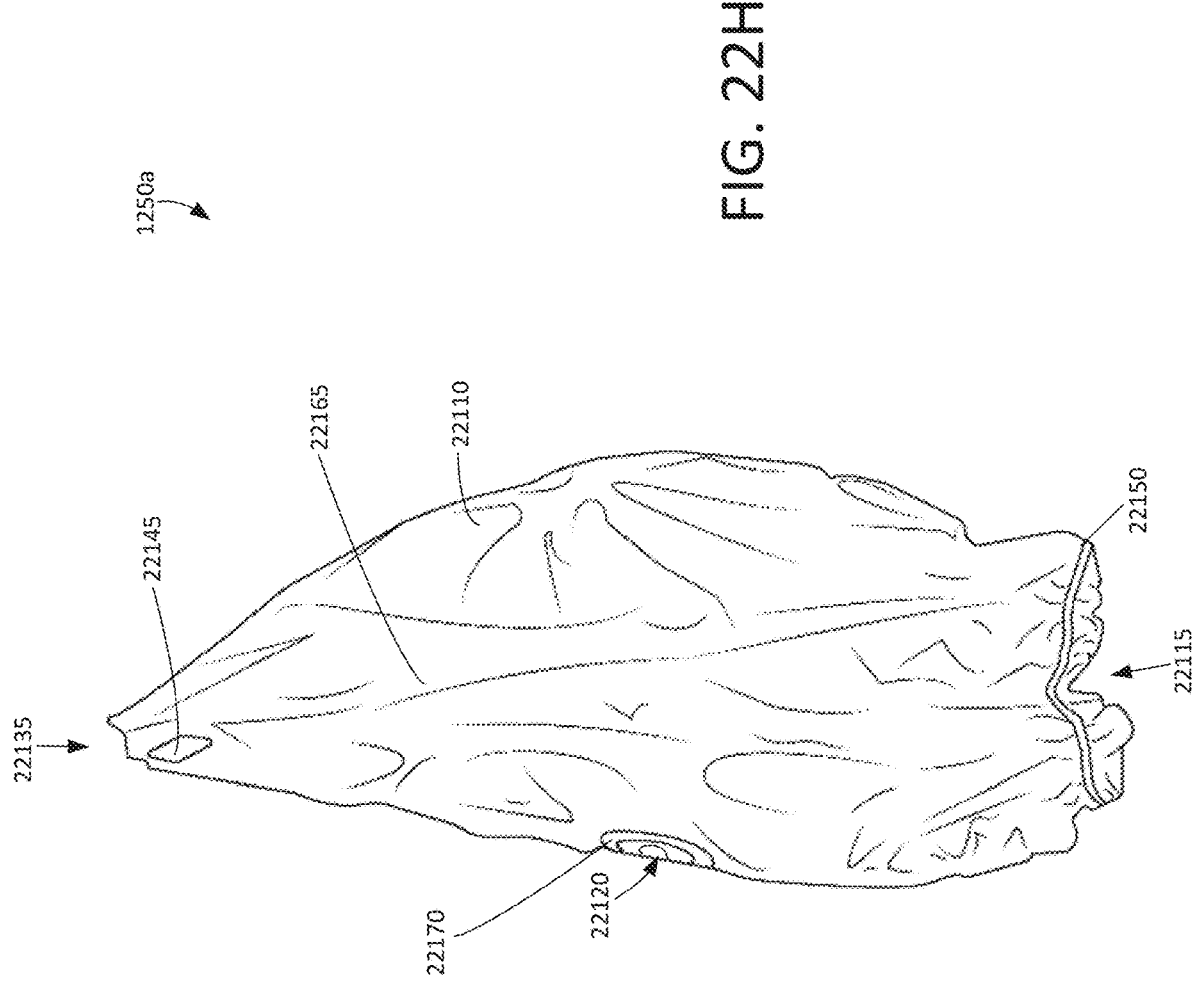

DISPOSABLE KIT

CROSS-REFERENCES TO RELATED PATENT APPLICATIONS

This application is a continuation of U.S. patent application Ser. No. 16/698,817, filed Nov. 27, 2019, which is a continuation of U.S. patent application Ser. No. 16/048,209, filed Jul. 27, 2018, now U.S. Pat. No. 10,492,877, issued on Dec. 3, 2019, which claims the priority to and the benefit of U.S. Provisional Patent Application No. 62/660,499, filed on Apr. 20, 2018, each of which is incorporated herein by reference in their entireties.

FIELD

Subject matter described herein relates generally to disposable kits configured to use in a medical procedure such as but not limited to, an ultrasound-related procedure.

BACKGROUND

For providing more effective healthcare, maintaining hygiene and cleanliness is a high priority for healthcare providers. One scenario in which hygiene may be compromised is when medical materials and instruments (e.g., placemats and sheets) are reused on different patients, which may enable and/or accelerate the transfer of bacteria or illness from patient to patient. In addition, reusable medical instruments and materials may be cumbersome for use by a healthcare provider, for example, due to storing, deploying, safekeeping, monitoring, and the like, of the reusable equipment.

SUMMARY

In some arrangements, a disposable kit containing medical items configured for a medical device includes a head cradle to support a head of a subject, the disposable kit includes a container that encloses a head cradle pad configured to be affixed to the head cradle, at least one fiducial marker configured to be disposed on a location at the head of the subject, and at least one enclosure configured to cover a portion of the medical device.

In some arrangements, the disposable kit contains medical items configured to be used for an ultrasound medical procedure.

In some arrangements, the head cradle pad is configured to be releasably affixed to the head cradle.

In some arrangements, the head cradle pad includes a pad layer and an adhesive layer. The head cradle pad is configured to be affixed to the head cradle via the adhesive layer.

In some arrangements, the pad layer is configured to be pressed into a concave surface of the head cradle. The adhesive layer contacts and adheres to the concave surface of the head cradle when the pad layer is pressed into the concave surface of the head cradle.

In some arrangements, the medical device includes a head restraint to restrain the head of the subject. The container further encloses a head restraint pad configured to be releasably affixed to the head restraint.

In some arrangements, the head restraint pad includes a pad layer and an adhesive layer. The head restraint pad is configured to be affixed to the head cradle via the adhesive layer.

In some arrangements, the pad layer is configured to be pressed into a concave surface of the head restraint. The adhesive layer contacts and adheres to the concave surface of the head restraint when the pad layer is pressed into the concave surface of the head restraint.

In some arrangements, the head restraint pad is configured to contact a forehead of the head of the subject.

In some arrangements, the head restraint pad contacts a bottom surface of the container and fits into a space defined by the bottom surface, a portion of side walls extending from the bottom surface, and a side surface of the head cradle pad.

In some arrangements, the at least one fiducial marker has an adhesive surface configured to be affixed to the head of the subject, and a light reflective surface opposite to the adhesive surface.

In some arrangements, the at least one fiducial marker includes a plurality of fiducial markers, each of the plurality of fiducial markers configured to be adhered to a same side of the head of the subject.

In some arrangements, the at least one fiducial marker includes a first set of fiducial markers and a second set of fiducial markers, each of the first set and the second set includes a plurality of fiducial markers and configured to be adhered to opposite sides of the head of the subject.

In some arrangements, the medical device includes at least one robotic pod includes a camera and a probe. The at least one enclosure has a removable enclosure body configured to cover a cavity defined by a housing of the at least one robotic pod, and a center hole configured to expose at least a portion of the probe.

In some arrangements, the medical device includes at least one robotic pod includes a camera and a probe. The at least one enclosure defines a top hole configured to expose the camera of the at least one robotic pod.

In some arrangements, the at least one enclosure includes a plurality of enclosures.

In some arrangements, the head cradle pad contacts a bottom surface of the container and fits into a space defined by the bottom surface and side walls extending from the bottom surface.

In some arrangements, the disposable kit includes no more and no less than the container. The container encloses no more and no less than the head cradle pad, a head restraint pad configured to be affixed to a head restraint of the medical device, a sheet carrying the at least one fiducial marker, the at least one enclosure, and a packaging enclosing the container.

In some arrangements, the medical device includes a Transcranial Doppler device.

In some arrangements, a method for providing a disposable kit containing medical items configured for a medical device having a head cradle to support a head of a subject, the method includes providing a container, wherein providing the container includes enclosing, in the container a head cradle pad configured to be affixed to the head cradle, at least one fiducial marker configured to be disposed on a location at the head of the subject, and at least one enclosure configured to cover a portion of the medical device.

BRIEF DESCRIPTION OF THE FIGURES

Features and aspects of arrangements will become apparent from the following description and the accompanying example arrangements shown in the drawings, which are briefly described below.

FIG. 11B shows a front view of the disposable placemat (unfolded) of the disposable kit shown in FIG. 1, according to various arrangements.

FIG. 20B shows a front view of the head cradle pad of the disposable kit shown in FIG. 12, according to various arrangements.

FIG. 20C shows a back view of the head cradle pad of the disposable kit shown in FIG. 12, according to various arrangements.

FIGS. 21C-21E illustrate a method of using the disposable kit shown in FIG. 12, according to various arrangement.

FIG. 22G shows a first side view of the disposable enclosure (unfolded) of the disposable kit shown in FIG. 12, according to various arrangements.

FIG. 22H shows a second side view of the disposable enclosure (unfolded) of the disposable kit shown in FIG. 12, according to various arrangements.

DETAILED DESCRIPTION

Figure 1:
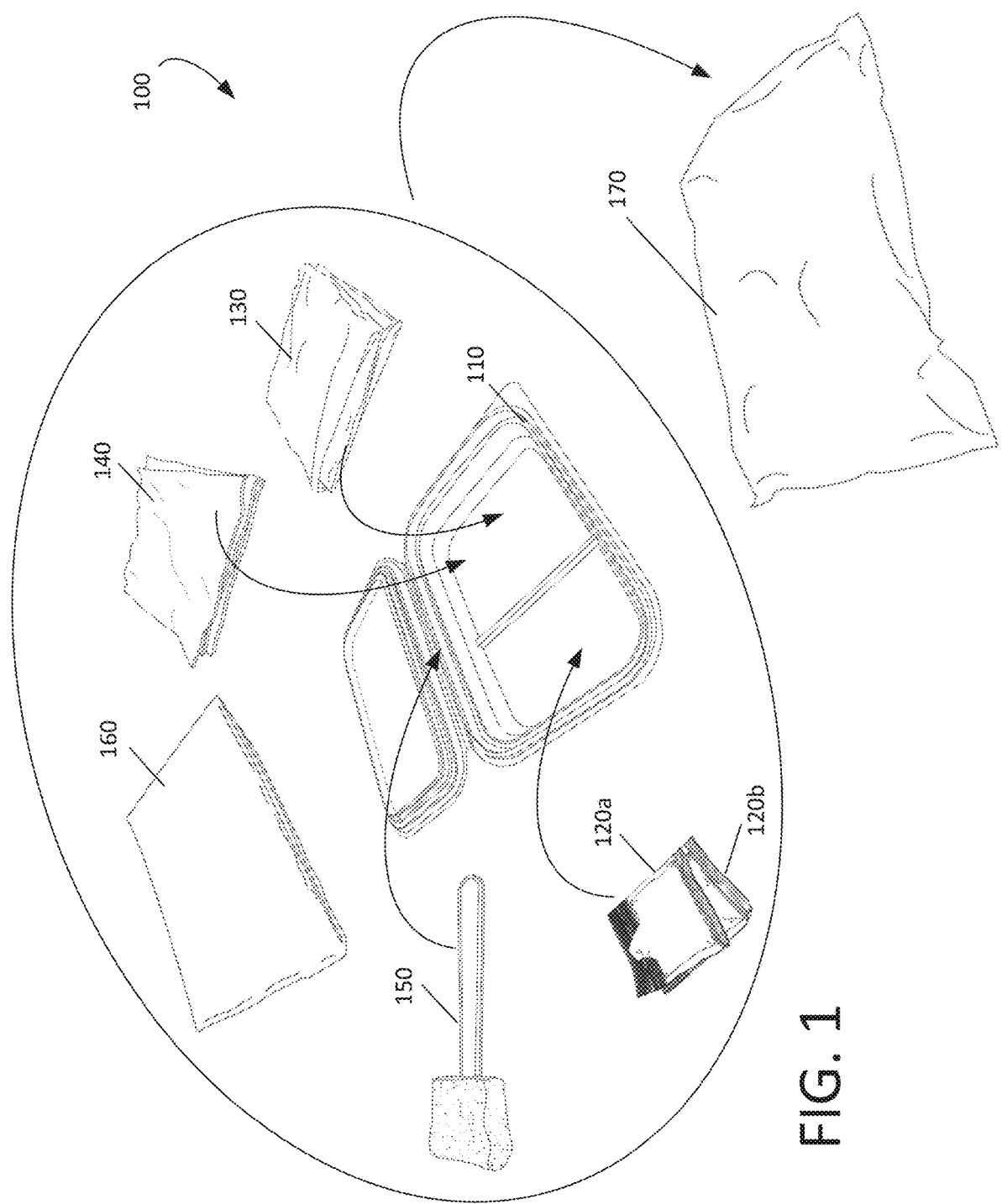
FIG. 1 shows components of an example of a disposable kit, according to various arrangements.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Arrangements described herein relate to systems, apparatuses, and methods for providing a disposable kit that contains a plurality of different disposable, medical items. For example, in some arrangements, the disposable kit and the medical items contained therein are not reused between different subjects. In some arrangements, a disposable kit as described herein can be used per a medical procedure and/or per a subject. In other arrangements, a disposable kit is reused between different medical procedures and/or between different medical subjects. In some arrangements, implementation and usage of the disposable kit described herein can improve hygiene and cleanliness while allowing healthcare providers to administer healthcare more efficiently, effectively, and easily.

In some arrangements, the disposable kit as described herein is used in conjunction with a medical procedure involving, for example, but not limited to, ultrasound (e.g., a Transcranial Doppler (TCD) procedure). In some arrangements, the disposable kit can be used for and in connection with a device (e.g., an ultrasound device, such as, but not limited to, a TCD ultrasound device) having one or more probes (e.g., ultrasound probes).

In some arrangements, the disposable kit as described herein is used in conjunction with other diagnostic ultrasound procedures, such as, but not limited to, needle guidance, intravascular ultrasound (e.g., examination of vessels, blood flow characteristics, clot identification, emboli monitoring, and so on), echocardiograms, abdominal sonography (e.g., imaging of the pancreas, aorta, inferior vena cava, liver, gall bladder, bile ducts, kidneys, spleen, appendix, rectal area, and so on), gynecologic ultrasonography (e.g., examination of pelvic organs such as uterus, ovaries, Fallopian tubes, and so on), obstetrical sonography, otolaryngological sonography (e.g., imaging of the thyroid (such as for tumors and lesions), lymph nodes, salivary glands, and so on), neonatal sonography (e.g., assessment of intracerebral structural abnormalities through soft spots of a skull of an infant, bleeds, ventriculomegaly, hydrocephalus, anoxic insults, and so on), ophthalmological procedures (e.g., A-scan ultrasound biometry, B-scan ultrasonography, and so on), pulmonological uses (e.g., endobronchial ultrasound (EBUS)), urological procedures (e.g., determination of an amount of fluid retained in a subject's bladder, imaging of pelvic organs (such as uterus, ovaries, urinary bladder, prostate, and testicles), and detection of kidney stones), scrotal sonography (e.g., to evaluate testicular pain, identify solid masses, and so on), musculoskeletal procedures (e.g., examination of tendons, muscles, nerves, ligaments, soft tissue masses, bone surfaces, and so on), bone fracture sonography, testing for myopathic disease, estimating lean body mass, proxy measures of muscle quality (e.g., tissue composition), nephrological procedures (e.g., renal ultrasonography), and the like.

In some arrangements, the disposable kit as described herein is used in conjunction with therapeutic ultrasound procedures, such as, but not limited to, high-intensity focused ultrasound (HIFU), focused ultrasound surgery (FUS), Magnetic resonance-guided focused ultrasound (MRgFUS), lithotripsy (e.g., breaking up kidney stones, bezoars, gall stones, and the like), targeted ultrasound drug delivery, trans-dermal ultrasound drug delivery, ultrasound hemostasis, cancer therapy, ultrasound-assisted thrombolysis, dental hygiene (e.g., cleaning teeth), phacoemulsification, ablation (e.g., of tumors or other tissue), acoustic targeted drug delivery (ATDD), trigger release of drugs (e.g., anti-cancer drugs), ultrasound-guided treatments (sclerotherapy, endovenous laser treatment, liposuction, and so on), and the like. In some arrangements, ultrasound is used for physical therapy applications, including, but not limited to, stimulating tissue beneath the skin's surface (e.g., by using very high frequency sound waves, such as, as an example, between about 800,000 Hz and 2,000,000 Hz), treating musculoskeletal ailments with ultrasound exposure (e.g., ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion), and the like.

In some arrangements, the one or more probes are configured to emit and/or receive ultrasound acoustic energy. For example, the device having one or more probes can automatically locate an artery (e.g., a middle cerebral artery (MCA)) of a brain of a subject. The subject may be a person, such as a medical patient, a test or experimentation subject, a wounded soldier, an animal, an inanimate object (e.g., pipes), or the like. In some arrangements, a probe can be positioned in a temporal window region (temple) of a head of the subject to collect the ultrasound data. In other arrangements, a probe can be positioned over different acoustic windows such as, but not limited to, the transorbital window or the suboccipital window. In some arrangements, a lubricating gel can be applied between the head and a probe to facilitate and improve acoustic transmission. Further disclosure regarding examples of a probe and a device with probes can be found in U.S. patent application Ser. No. 15/399,648, titled ROBOTIC SYSTEMS FOR CONTROL OF AN ULTRASONIC PROBE, filed on Jan. 5, 2017, and in U.S. patent application Ser. No. 15/853,433, titled HEADSET SYSTEM, filed Dec. 22, 2017, each of which is incorporated herein by reference in its entirety.

The current disclosure relates to a set of selected medical items, packaged or otherwise contained in a disposable kit as described herein, where the particular set of medical items in the package are provided and arranged in the package, to enable a healthcare provider to perform a medical procedure for a given subject, and efficiently and easily use the medical items in the package during the medical procedure. In some arrangements, the selection of items in a disposable kit as described herein is for a particular medical procedure (e.g., involving diagnostic or therapeutic ultrasound) for a subject, such that under ordinary circumstances, some or all of the items in the disposable kit are used for the medical procedure for the single subject. In certain examples, the disposable kit includes all of the medical items, and no more medical items, than typically used in the particular medical procedure. As such, in some arrangements, the disposable kit includes medical items that can be used during the medical procedure and disposed of after the medical procedure is completed, such that the same medical items are not re-used for another medical procedure or another subject. In that regard, in some arrangements, the kit and the medical items packaged or otherwise contained therein can be characterized as "disposable."

In addition, in some arrangements, the medical items packaged or otherwise contained in a disposable kit are arranged in a particular order and configuration to enable a healthcare provider to efficiently and easily use the medical items with respect to a medical procedure. In some arrangements, the items in a disposable kit as described herein can be arranged in the disposable kit according to an order in which the items are to be retrieved from the disposable kit by the healthcare provider in performing the medical procedure. To generally illustrate, in some arrangements, the disposable kit as described herein includes at least a first item and a second item. The first item is to be used before the second item for a medical procedure. The first item can be arranged on top of the second item or other items, or to be closer to an opening of a disposable container than the second item, such that the first item can be easily retrieved from the opened container, first, without the user having to touch or otherwise contact or move the second (or other) items. Particularly in some examples, the first item can be placed on top of the second item within the disposable container such that the first item can be retrieved or otherwise accessed by the healthcare provider prior to the second item is exposed. The second item is between the first item and a third item or a bottom surface of the disposable kit. The second item is exposed after the first item is retrieved, thus allowing the second item to be subsequently retrieved, and so on.

Traditionally, different types of medical items used for a given medical procedure (e.g., an ultrasound scan) are stored in different containers, such that all medical items used for the medical procedure are sorted and stored according to type. Given that, in some arrangements, a disposable kit contains a selection and arrangement of medical items that are no more than and no fewer/less than those needed for a single medical procedure (e.g., a single ultrasound scan) for a single subject, a healthcare provider does not need to separately retrieve different types of medical items from different containers. This significantly improves operational efficiency for administering the medical procedure.

Furthermore, in some arrangements, a suitable number of disposable kits with medical items (e.g., sterilized medical items) can be made available to the healthcare provider for use. In some arrangements, the disposable kits and the medical items contained therein can be sterilized before the medical procedure. In that manner, the healthcare provider does not need to re-sterilize medical items before and/or after each use. As such, the disposable kits as described herein can improve overall operational efficiency and hygiene/cleanliness (reduce infections) in medical or emergency settings (e.g., hospital emergency rooms, urgent care, veterinarian offices, physician offices, military hospitals, penitentiaries, combat support hospitals, forward surgical teams, mobile military medicine teams, military medics, disaster relief medical teams, and the like) in which different subjects are in need of the medical procedures.

FIG. 1 shows various components of an example of a disposable kit 100, according to various arrangements. Referring to FIG. 1, in some arrangements, the disposable kit 100 includes a disposable container 110, at least one disposable gel container (e.g., the disposable gel containers 120a and 120b), a disposable hair restraint 130, disposable wipes 140, a disposable gel applicator 150, a disposable placemat 160, and disposable packaging 170. In some arrangements, each of the disposable gel containers 120a and 120b are openable packets configured to store a gel, which can be applied between the head of a subject and a probe to facilitate and improve acoustic transmission. In some arrangements, the disposable hair restraint 130 is a stretchable band configured to be placed on the head of a subject to hold hair of the subject in place during the medical procedure, to prevent the hair from interfering with data collection and movements of the probe. In some arrangements, the disposable wipes 140 can be used to wipe blood, sweat, particles (e.g., hair, sand, dirt, and the like), and previously applied gel off the subject. In some arrangements, the disposable wipes 140 can be used to wipe gel off of the head of the subject after the medical procedure is performed. The disposable gel applicator 150 can be used to apply the gel stored by the disposable gel containers 120a and 120b onto the subject. In some arrangements, the disposable placemat 160 is configured to absorb a fluid (e.g., a bodily fluid, the gel, and the like) used in conjunction with a medical procedure, while keeping a surface on which the subject lies clean.

In some arrangements, one or more of the items 120a, 120b, 130, 140, and 150 in the disposable container 110 are sterilized before being placed into the disposable container 110. In some arrangements, the disposable container 110, the disposable placemat 160, and the disposable packaging 170 are sterilized. In some use cases, even when the disposable packaging 170 and the disposable placemat 160 have been opened and used, the disposable container 110 (which may be sealed to provide ingress protection) maintains the items 120a, 120b, 130, 140, and 150 in their sterilized conditions so that the healthcare provider can later use the items 120a, 120b, 130, 140, and 150, for example, after breaking the seal of the disposable container 110. As such, in some arrangements, the disposable kit 100 provides two levels of protection for the items therein (e.g., protection from the items being contaminated from outside): a first level corresponding to the disposable packaging 170 protecting the disposable placemat 160 and the disposable container 110, and a second level corresponding to the disposable container 110 protecting the items 120a, 120b, 130, 140, and 150.

In some arrangements, the disposable container 110 is configured to store or otherwise contain the disposable gel containers 120a and 120b, the disposable hair restraint 130, the disposable wipes 140, and the disposable gel applicator 150. In some arrangements, the disposable container 110 can be opened to allow a healthcare provider to retrieve or otherwise access the medical items 120a, 120b, 130, 140, and 150 in the disposable container 110, in a desired order. The disposable container 110 can be closed to enclose the items 120a and 120b, 130, 140, and 150.

In some arrangements, the disposable kit 100 includes no more and no fewer types of medical items than the types of medical items shown in FIG. 1. For example, the disposable kit 100 may include no more and no fewer than disposable gel container(s) (e.g., the disposable gel containers 120a and 120b), disposable hair restraint(s) (e.g., the disposable hair restraint 130), disposable wipe(s) (e.g., the disposable wipes 140), disposable gel applicator(s) (e.g., the disposable gel applicator 150), and disposable placemat(s) (e.g., the disposable placemat 160). In other arrangements, the disposable kit 100 includes more or fewer types of items than the types shown in FIG. 1. In some arrangements, the disposable kit 100 includes any number of each item type. In particular examples, the number of each type of medical item and/or the types of medical items included are selected to correspond to the number of such items that are typically used in the particular medical procedure associated with the disposable kit 100. In other examples, one or more extra items of one or more (or each) of each type of item is included in the disposable kit 100, for example, where the one or more extra items are selected to correspond to the number of extra items that are typically used in the particular medical procedure, when extra items are needed.

In particular examples, the item types in the disposable kit 100 and the number of items for each item type in the disposable kit 100 are enough for a medical procedure involving ultrasound (such as but not limited to, an ultrasound scan, such as TCD) for a single patient or subject. In other words, in some arrangements, the selection of the items in the disposable kit 100 includes the appropriate number and types of items that can be used on a single subject for a single ultrasound procedure, without the need to open an additional disposable kit and with minimal or no wasting of unused items in the disposable kit 100. As an example, the disposable kit 100 includes the two disposable gel containers 120a and 120b, each having a net weight of 20 g. The number of disposable gel containers depends on the size of each gel container and the anticipated amount of gel needed to complete the medical procedure involving ultrasound. For example, the anticipated amount of gel may depend on sizes of one or more body areas on which the gel is to be applied. In some arrangements, the disposable kit 100 includes one disposable hair restraint 130. In some arrangements, one hair restraint is used to tie up the hair of one subject, therefore, one hair restraint is included in the disposable kit 100. In some arrangements, the disposable kit 100 includes the five disposable wipes 140. The number of disposable wipes depends on the anticipated number of wipes needed to complete the medical procedure involving ultrasound (e.g., the number of wipes for adequately cleaning the gel from a subject after the medical procedure is concluded). In some arrangements, the disposable kit 100 includes the one disposable gel applicator 150, given that one gel applicator is sufficient to apply the gel for a single subject. In some arrangements, the disposable kit 100 includes the one disposable placemat 160, given that one placemat is sufficient to be deployed to absorb liquid and keep the work surface clean.

Figure 2:
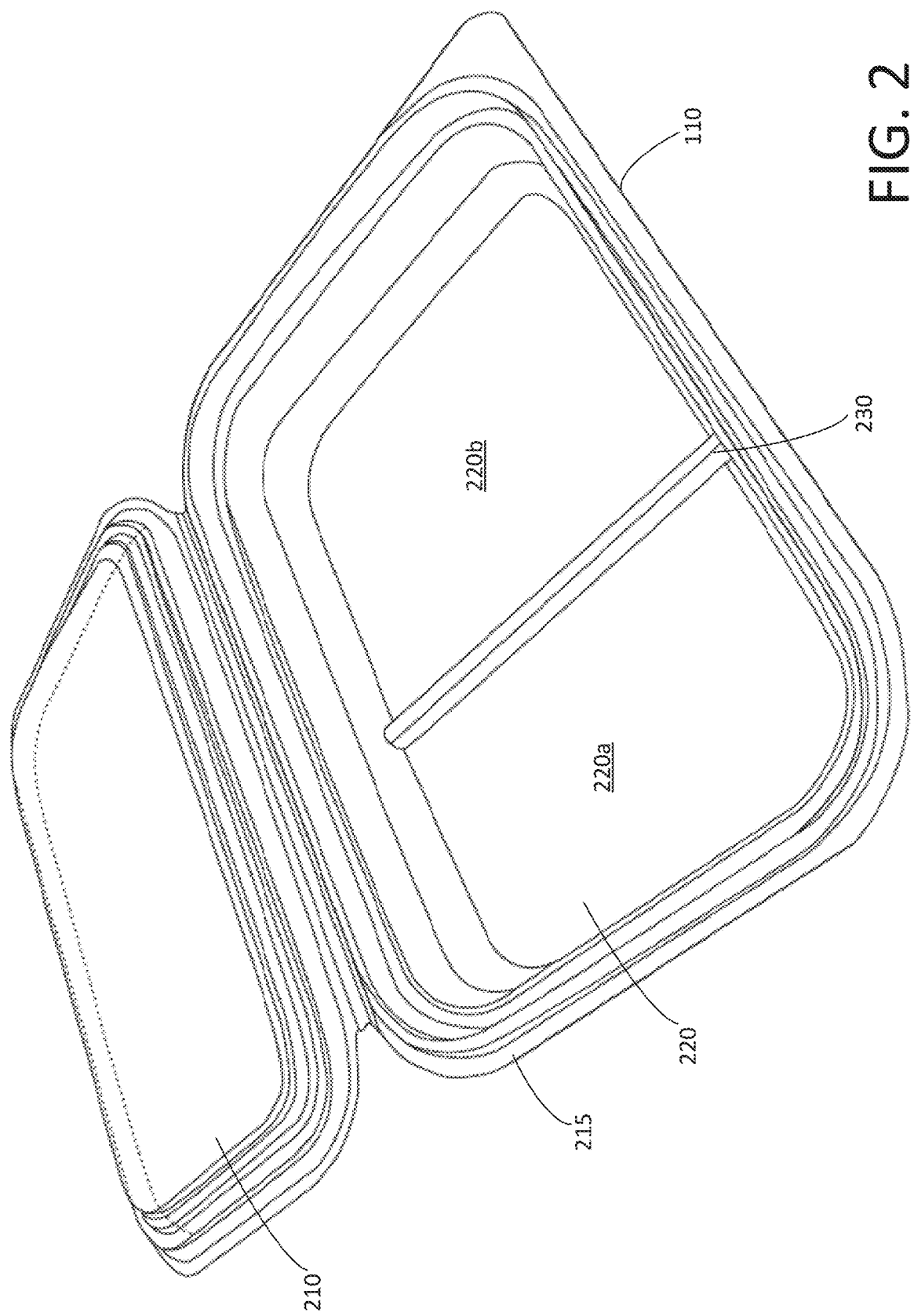
FIG. 2 shows a perspective view of the disposable container (opened) of the disposable kit shown in FIG. 1, according to various arrangements.

FIGS. 2-10 illustrate a method by which the disposable kit 100 is manufactured or otherwise assembled. In certain examples, the disposable kit 100 may be assembled in the order shown in FIGS. 2-10, to provide an arrangement of medical items organized and positioned within the disposable kit 100 to allow the medical items to be easily retrieved from the disposable kit in the order in which they are typically used, without touching or disrupting the order of other medical items in the disposable kit. FIG. 2 shows the disposable container 110 (opened) of the disposable kit 100, according to various arrangements. Referring to FIGS. 1-2, the disposable container 110 is lightweight for easy transportation and storage. In some examples, the disposable container 110 can be made from an inexpensive material having sufficient rigidity to hold its shape, and suitable for mass production. The disposable container 110 can be made from a transparent or translucent material such that the healthcare provider can easily see whether the items stored in the disposable container 110 have already been used and whether the items stored in the disposable container 110 have been tampered with or contaminated. In that regard, the disposable container 110 can be made from a plastic material such as but not limited to, polyethylene, polypropylene, polystyrene, and the like. In other examples, the disposable container 110 can be made from glass, paperboard, ceramic, and the like.

As shown, the disposable container 110 includes a bottom portion 215. The bottom portion 215 includes a bottom surface 220 and side walls extending from the bottom surface 220. The bottom surface 220 supports the items 120a, 120b, 130, 140, and 150. The bottom surface 220 is divided into a first bottom surface 220a and a second bottom surface 220b by a wall or ridge 230. In some examples, one of the bottom surfaces 220a and 220b has a bigger area than that of the other one of the bottom surfaces 220a and 220b. As shown, the first bottom surface 220a has a smaller area than that of the second bottom surface 220b. This is because the first bottom surface 220a is configured to support the disposable gel containers 120a and 120b, and the second bottom surface 220b is configured to support the disposable hair restraint 130 (folded) and the disposable wipes 140 (folded). The width of each of the disposable gel containers 120a and 120b is less than the width of each of the disposable hair restraint 130 (folded) and the disposable wipes 140 (folded). Thus, in order for the disposable gel containers 120a and 120b, the disposable hair restraint 130 (folded), and the disposable wipes 140 (folded) to fit tightly in the disposable container 110 (e.g., on the bottom portion 215), the ridge 230 partitions the bottom surface 220 according to the dimensions (e.g., the widths) of the disposable gel containers 120a and 120b, the disposable hair restraint 130 (folded), and the disposable wipes 140 (folded). The ridge 230 and some portions of the side wall of the bottom portion 215 define a space in which the disposable gel containers 120a and 120b fit. The ridge 230 and other portions of the side wall of the bottom portion 215 define another space in which the disposable hair restraint 130 and the disposable wipes 140 fit. In other examples, the bottom surfaces 220a and 220b have the same area (e.g., the ridge 230 divides the bottom surface 220 evenly).

In some arrangements, the ridge 230 is located at any location along the bottom surface to provide varying surface areas of the first bottom surface 220a and the second bottom surface 220b as desired to accommodate different types of items to be stored within the disposable container 110. In other arrangements, a plurality of ridges 230 are implemented to provide more than two compartmentalized bottom surfaces of equal or varying surface areas. In some arrangements, the ridge 230 is located along the length of the container 110 or along the width of the container 110 or along both (e.g., such that four or more compartments are formed). In some arrangements, the ridge 230 is located diagonally along the bottom surface 220 such that two or more non-rectangular-shaped compartments are formed (e.g., triangular-shaped compartments). In other arrangements, the container 110 does not include the ridge such that the container 110 defines one continuous and uninterrupted bottom surface 220.

In some arrangements, the disposable container 110 includes a lid 210. The lid 210 is configured to be opened to provide access to an interior of the disposable container 110. The interior of the container 110 is defined by the bottom portion 215 (e.g., by the side walls and the bottom surface 220). The lid 210 has an interior surface facing the interior of the container 110 when the lid 210 is closed. The interior surface of the lid 210 faces the bottom surface 220 (e.g., the bottom surfaces 220*a* and 220*b*) when the lid 210 is closed. As shown, the lid 210 can mate with the bottom portion 215 via friction fit. In other examples, the lid 210 can mate with the bottom portion 215 via one or more of a zipper, buttons, a press seal, a re-sealable seal (e.g., a zip-top), adhesives, latches, strings, and the like. In some arrangements, the lid 210 and the bottom portion 215 are connected by one or more hinges. In other arrangements, the lid 210 and the bottom portion 215 are separate and are not connected. In some arrangements, the lid 210 and the bottom portion 215 can form a water-tight seal or air-tight seal (or both) to provide ingress protection, thus maintaining the cleanliness of the items 120*a*, 120*b*, 130, 140, and 150 and reducing bacteria count within the interior of the disposable container 110 when the lid 210 is closed. In some arrangements, the disposable container 110 is sealed shut between the lid 210 and the bottom portion 215 so that the items 120*a*, 120*b*, 130, 140, and 150 therein are secured, and such that a healthcare provider can readily determine whether the disposable container 110 has been tampered with prior to use, in which case the healthcare provider can simply use another disposable kit 100. For example, the disposable container 110 can be sealed with a tape such that it is readily apparent whether the tape has been previously released, cut, or otherwise opened.

Figure 3:
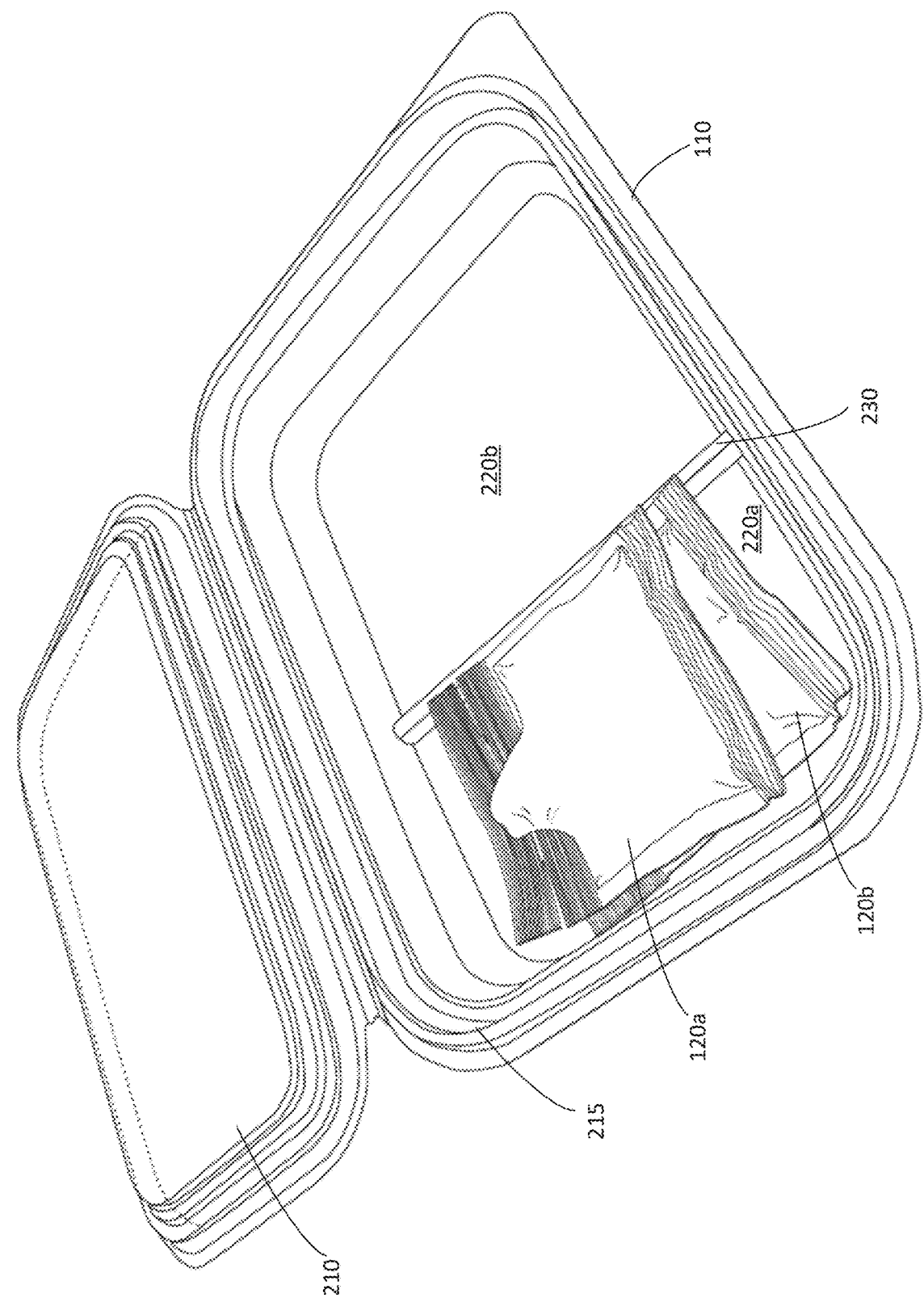
FIG. 3 shows a perspective view of the disposable container (opened) containing the disposable gel containers of the disposable kit shown in FIG. 1, according to various arrangements.

FIG. 3 shows the disposable container 110 (opened) containing the disposable gel containers 120*a* and 120*b* of the disposable kit 100, according to various arrangements. Referring to FIGS. 1-3, the disposable gel containers 120*a* and 120*b* can be first placed in the disposable container 110 during a manufacturing process of the disposable kit 100. In some arrangements, the disposable gel containers 120*a* and 120*b* are disposable gel packets that store ultrasound gel, which aids in the transmission of ultrasound waves for ultrasound procedures. Each of the disposable gel containers 120*a* and 120*b* includes perforations or tears to allow a healthcare provider to easily and swiftly open the disposable gel containers 120*a* and 120*b* and apply the gel. The gel stored in the disposable gel containers 120*a* and 120*b* can be water soluble, hypoallergenic, dye-free, and greaseless. In other examples, the disposable gel containers 120*a* and 120*b* may store any other suitable types of liquid such as but not limited to, cleaning solutions for the device or other liquids or gels used in conjunction with a medical procedure.

The disposable gel containers 120*a* and 120*b* are arranged on the bottom surface 220*a*, in a stacked configuration. For example, the disposable gel container 120*b* rests on and contacts the first bottom surface 220*a*. The disposable gel container 120*a* is stacked on top of the disposable gel container 120*b*. The disposable gel container 120*b* is between the disposable gel container 120*a* and the first bottom surface 220*a*.

Figure 4:
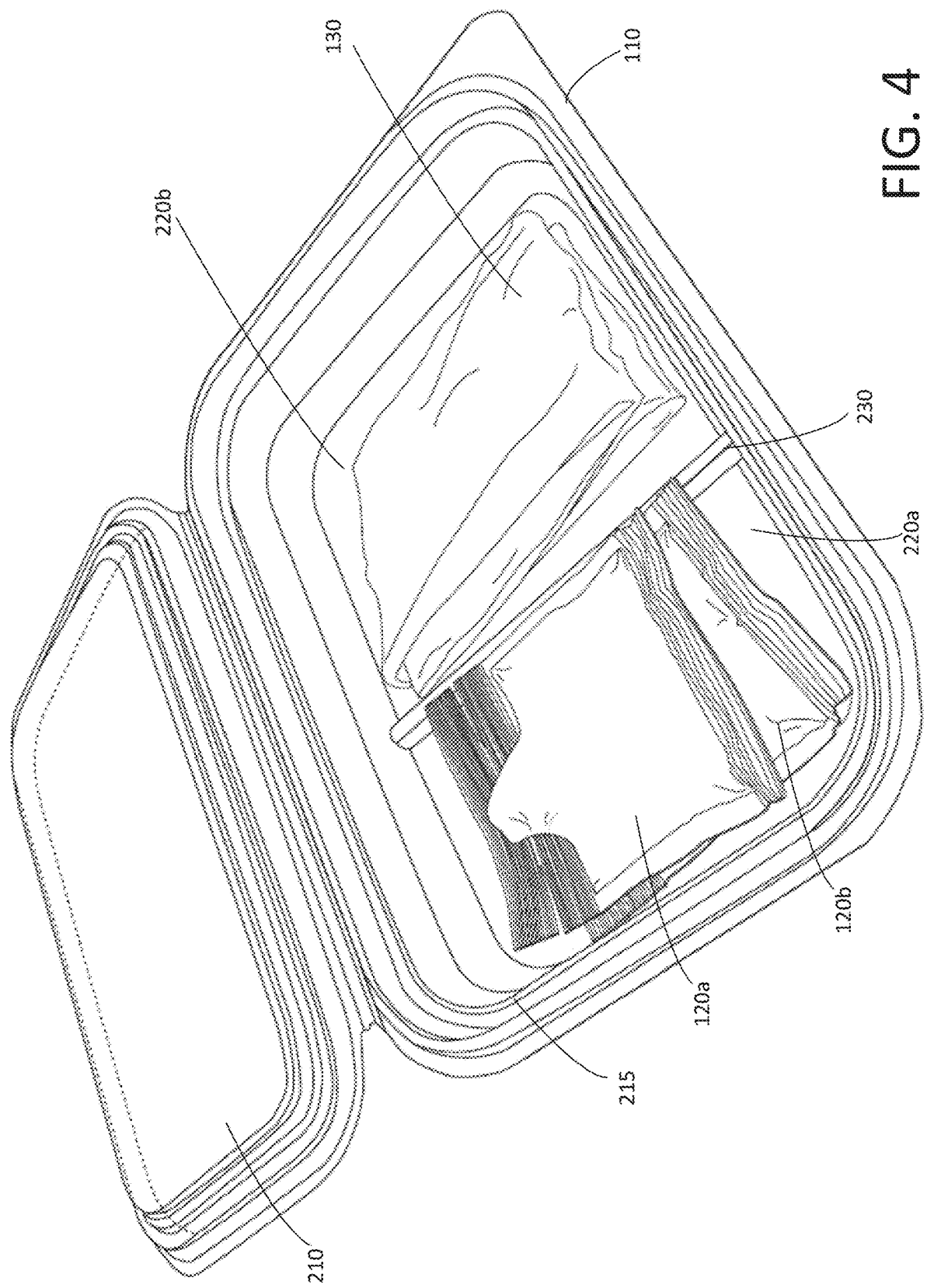
FIG. 4 shows a perspective view of the disposable container (opened) containing the disposable gel containers and the disposable hair restraint of the disposable kit shown in FIG. 1, according to various arrangements.

FIG. 4 shows the disposable container 110 (opened) containing the disposable gel containers 120*a* and 120*b* and the disposable hair restraint 130 of the disposable kit 100, according to various arrangements. Referring to FIGS. 1-4, the disposable hair restraint 130 can be placed in the disposable container 110 after the disposable gel containers 120*a* and 120*b* are placed in the disposable container 110 in some examples during the manufacturing process of the disposable kit 100. In other examples, the disposable hair restraint 130 can be first placed in the disposable container 110 during the manufacturing process of the disposable kit 100. The disposable hair restraint 130 is configured to be supported by and contacts the second bottom surface 220*b*. In the example shown in FIG. 4, the disposable hair restraint 130 is located on one side of the disposable gel containers 120*a* and 120*b*, for example, with the ridge 230 between the disposable hair restraint 130 and the stacked disposable gel containers 120*a* and 120*b*, such that both (or either) the disposable hair restraint 130 and the stacked disposable gel containers 120*a* and 120*b* may be retrieved, or either the disposable hair restraint 130 or the stacked disposable gel containers 120*a* and 120*b* may be retrieved without touching the other of the disposable hair restraint 130 and the stacked disposable gel containers 120*a* and 120*b*.

The disposable hair restraint 130 can be made from any suitable elastic or stretchable material configured as a band to expand to fit over a head of the subject. In that regard, the disposable hair restraint 130 is configured to remove and maintain a subject's hair away from an area at which the gel is applied and a medical procedure (e.g., a medical procedure using ultrasound, such as, but not limited to, a TCD procedure) is performed. The disposable hair restraint 130 can prevent the hair from interfering with data collection and movements of the probe during the medical procedure. As shown, the disposable hair restraint 130 is a disposable elastic band. In other examples, the disposable hair restraint 130 can be cap, a string, a band with adhesives configured to allow the band to stick to the skin of the subject, and the like. The disposable hair restraint 130 can be made from a biocompatible material. Examples of the material of the disposable hair restraint 130 include but are not limited to, elastic cloth, a layer of thin silicone, biocompatible fibers or fabric, a medical curtain (e.g., a polyethylene curtain), treated paper, Tyvek®, and the like.

Figure 5:
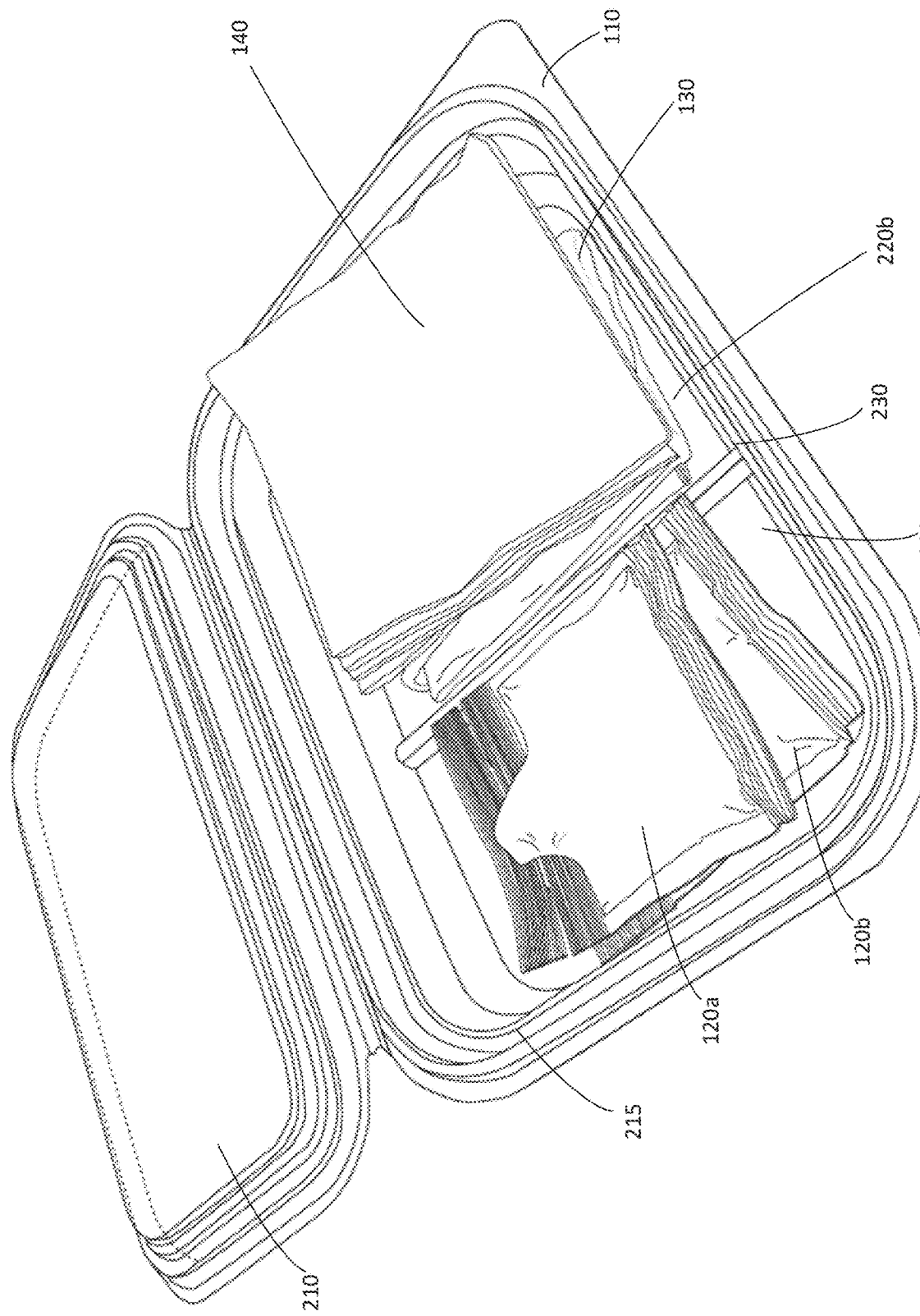
FIG. 5 shows a perspective view of the disposable container (opened) containing the disposable gel containers, the disposable hair restraint, and the disposable wipes of the disposable kit shown in FIG. 1, according to various arrangements.

FIG. 5 shows the disposable container 110 (opened) containing the disposable gel containers 120*a* and 120*b*, the disposable hair restraint 130, and the disposable wipes 140 of the disposable kit 100, according to various arrangements. Referring to FIGS. 1-5, the disposable wipes 140 are placed in the disposable container 110 after the disposable hair restraint 130 has been placed in the container. The disposable wipes 140 are placed on top of the disposable hair restraint 130, over the second bottom surface 220*b*. In that regard, the disposable hair restraint 130 is between the second bottom surface 220*b* and the disposable wipes 140. In some examples, the disposable wipes 140 are placed after the disposable gel containers 120*a* and 120*b* are placed in the disposable container 110 during the manufacturing process of the disposable kit 100. In other examples, the disposable wipes 140 are placed before the disposable gel containers 120*a* and 120*b* are placed in the disposable container 110 during the manufacturing process of the disposable kit 100.

The disposable wipes 140 are configured to wipe off gel previously applied to the subject. The disposable wipes 140 can be further configured to wipe off other types of liquid such as but not limited to water, bodily fluid (e.g., blood, urine, vomit, fecal matter, pus, and saliva), and the like. In that regard, the disposable wipes 140 may be made from one or more suitable absorbent materials such as but not limited to, paper, fabric, gauze, cotton, rayon, polyester, polyethylene, polypropylene, fiber, sponge, polyethylene terephthalate, wood pulp, combinations thereof, and the like.

In some examples, the disposable wipes 140 are disinfecting wipes configured to disinfect the device and the one or more probes without damaging such equipment. A problem with using other wipes that are not designed for use with device (e.g., ultrasound equipment) is that the non-ultrasound equipment wipes may damage the equipment. For example, alcohol and solvents can dry and crack cables, touchscreens can become unresponsive to touch, and imaging effectiveness of ultrasound probes can be damaged. Thus, according to some arrangements, the disposable wipes 140 can be compatible with ultrasound equipment and can be made from such compounds as, but not limited to, water, decyldimethyloctylammonium chloride, dimethyldioctylammonium chloride, didecyldimethylammonium chloride, quaternary ammonium compounds, benzyl-C12-16-alkyldimethyl, combinations thereof, and the like. As such, the chemical compound as described above can have antibacterial, disinfecting, and ultrasound equipment compatibility characteristics. The disposable wipes 140 can include a membrane, a cover, or a container for retaining the disinfecting solution.

Figure 6:
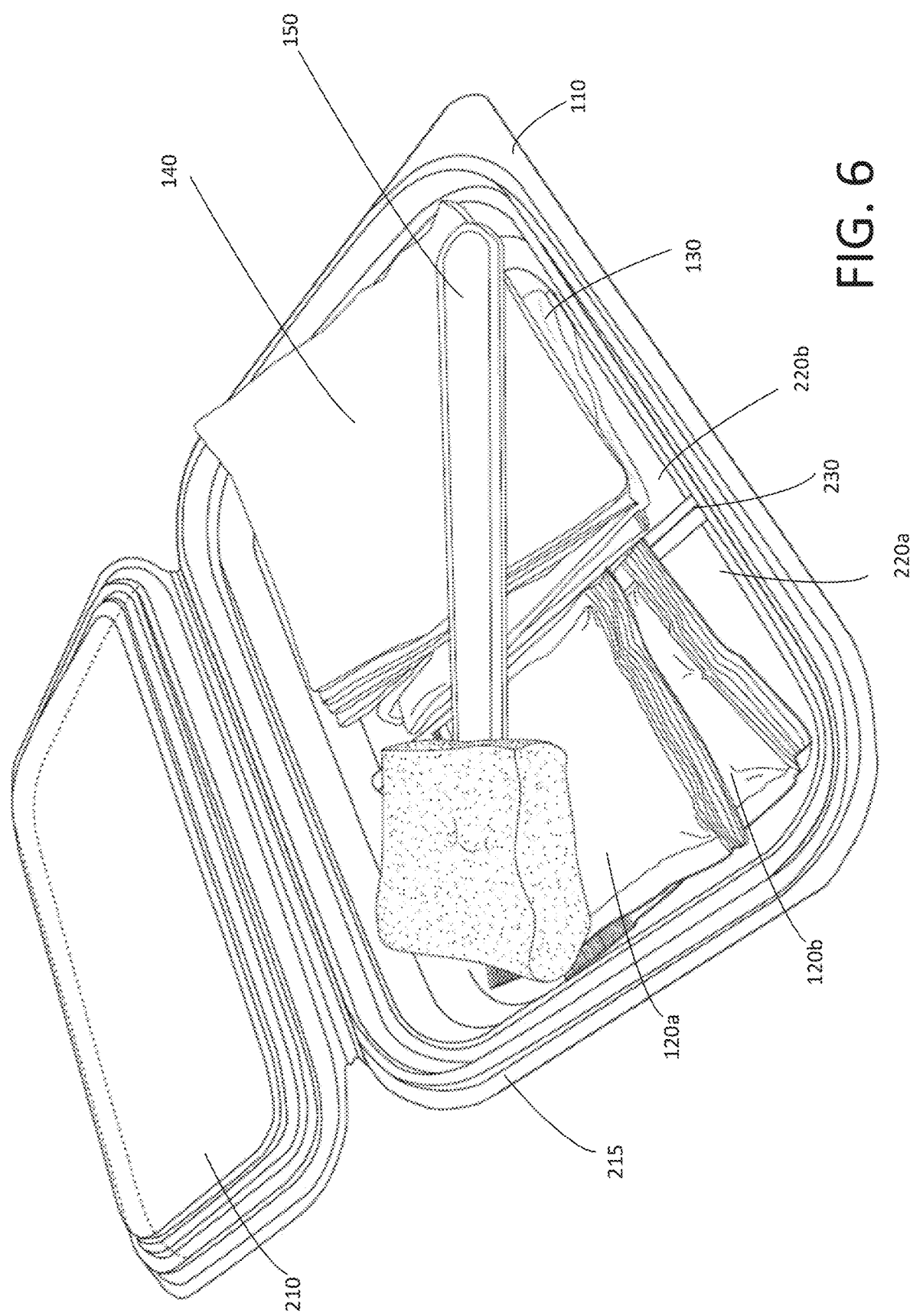
FIG. 6 shows a perspective view of the disposable container (opened) containing the disposable gel containers, the disposable hair restraint, the disposable wipes, and the disposable gel applicator of the disposable kit shown in FIG. 1, according to various arrangements.
Figure 7:
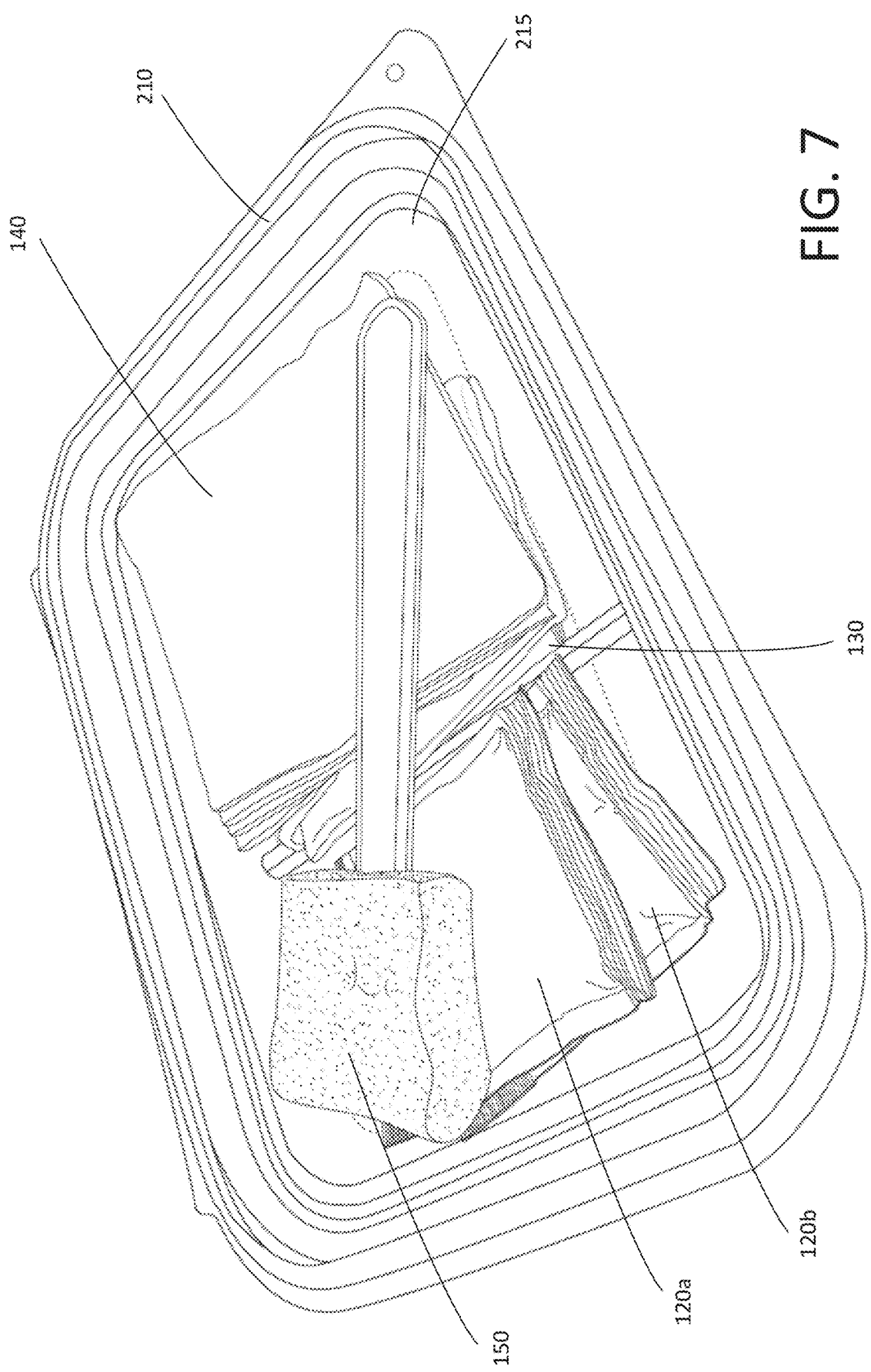
FIG. 7 shows a perspective view of the disposable container (closed) containing the disposable gel containers, the disposable hair restraint, the disposable wipes, and the disposable gel applicator of the disposable kit shown in FIG. 1, according to various arrangements.

FIG. 6 shows the disposable container 110 (opened) containing the disposable gel containers 120*a* and 120*b*, the disposable hair restraint 130, the disposable wipes 140, and the disposable gel applicator 150 of the disposable kit 100, according to various arrangements. FIG. 7 shows the disposable container 110 (closed) containing the disposable gel containers 120*a* and 120*b*, the disposable hair restraint 130, the disposable wipes 140, and the disposable gel applicator 150 of the disposable kit 100, according to various arrangements. Referring to FIGS. 1-7, the disposable gel applicator 150 is placed in the disposable container 110 after the disposable gel containers 120*a* and 120*b*, the disposable hair restraint 130, and the disposable wipes 140 are placed in the disposable container 110. The disposable gel applicator 150 is configured to be set on top of and to contact the disposable gel containers 120*a* and 120*b* and the disposable wipes 140. The disposable gel containers 120*a* and 120*b*, the disposable hair restraint 130, and the disposable wipes 140 are between the bottom surface 220 and the disposable gel applicator 150. As shown, the disposable gel applicator 150 is configured to be placed diagonally within the space defined by the bottom surface 220, the side walls of the bottom portion 215, and the lid 210 when the lid 210 is closed as shown in FIG. 7. The disposable gel applicator 150 is configured to be placed diagonally over the disposable gel containers 120*a* and 120*b* and the disposable wipes 140. The diagonal arrangement of the disposable gel applicator 150 in the disposable container 110 allows the disposable gel applicator to have a maximized length dimension, relative to the size of the disposable container 110, where the length dimension of the disposable gel applicator 150 may be longer than the width and length dimensions of the disposable container 110. In particular examples, the ridge 230 in the bottom portion of the disposable container 110 is sufficiently small in height so as not to extend above the other items housed within the disposable container 110 (e.g., the disposable gel containers 120*a* and 120*b* and the disposable wipes 140) so as to allow the disposable gel applicator 150 to be arranged diagonally within the disposable container 110 without obstruction by the ridge 230.

As shown, the disposable gel applicator 150 includes a handle and a foam pad at a first end of the handle. The handle may be made of any suitably rigid material such as, but not limited to plastic, wood, metal, ceramic, composite material or the like. The foam pad can be made from any compressible absorbent material. The gel from the disposable gel containers 120*a* and 120*b* can be applied to the foam pad for application onto a subject (e.g., onto the subject's head). The foam pad is configured to be placed over the disposable gel containers 120*a* and 120*b*. A second end of the handle opposite to the first end is configured to be placed over the disposable hair restraint 130 and the disposable wipes 140. This is because a space in the disposable container 110 between the lid 210 (closed) and the disposable gel container 120*a* is larger than a space in the disposable container 110 between the lid 210 (closed) and the disposable wipes 140. Given that the disposable hair restraint 130 and the disposable wipes 140 are at least somewhat elastic, the second end of the plastic handle may compress the disposable hair restraint 130 and the disposable wipes 140 toward the bottom surface 220 when the lid 210 is closed. The disposable gel applicator 150 (the foam pad and/or the plastic handle) contacts the interior surface of the lid 210 when the lid is closed. This minimizes movement of the disposable gel applicator 150, the disposable hair restraint 130, and the disposable wipes 140 within the disposable container 110 when the lid 210 is closed. Given that the foam pad (as well as the disposable gel containers 120*a* and 120*b* in some examples) is compressible, the foam pad may compress the disposable gel containers 120*a* and 120*b* and/or push the disposable gel containers 120*a* and 120*b* into a position within the disposable container 110 that minimizes movement of the disposable gel applicator 150 and the disposable gel containers 120*a* and 120*b* within the disposable container 110 when the lid 210 is closed. In other examples, the disposable gel applicator 150 can be configured in other forms such as but not limited to, a foam pad without a handle, a flat stick (e.g., a popsicle stick), a sponge, a spoon, a stick, a dispenser, syringe, and the like.

Figure 8:
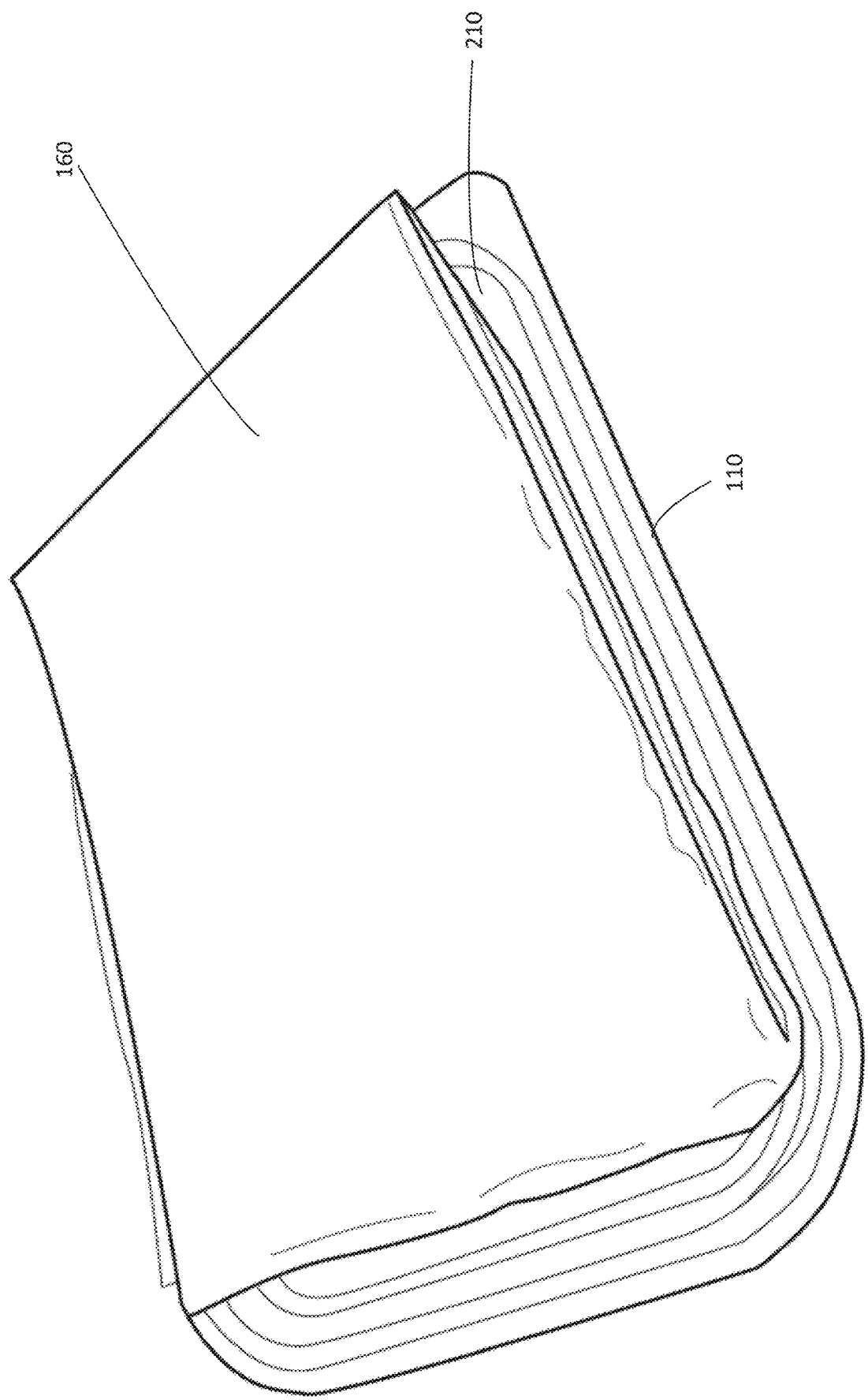
FIG. 8 shows a perspective view of the disposable container (closed) containing the disposable gel containers, the disposable hair restraint, the disposable wipes, and the disposable gel applicator, with the disposable placemat placed on top of the disposable container of the disposable kit shown in FIG. 1, according to various arrangements.
Figure 9:
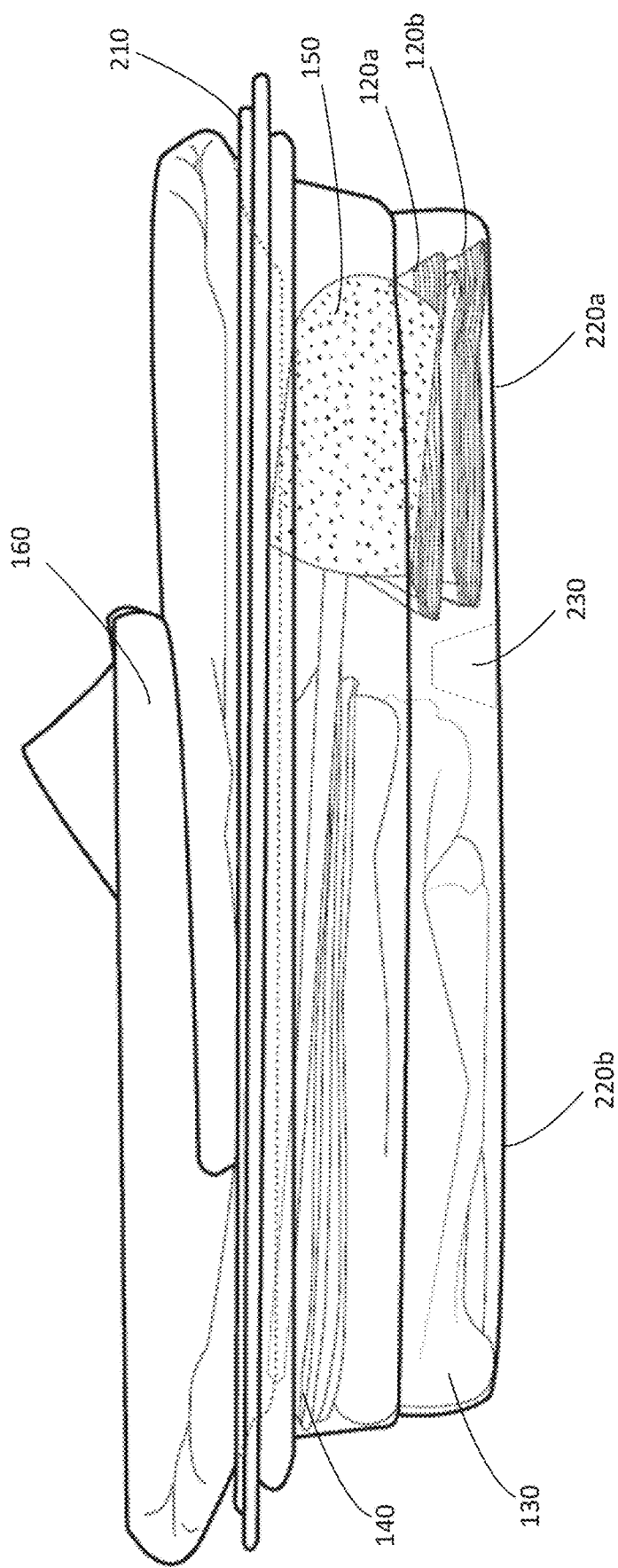
FIG. 9 shows a side view of the disposable container (closed) containing the disposable gel containers, the disposable hair restraint, the disposable wipes, and the disposable gel applicator, with the disposable placemat placed on top of the disposable container of the disposable kit shown in FIG. 1, according to various arrangements.
Figure 10:
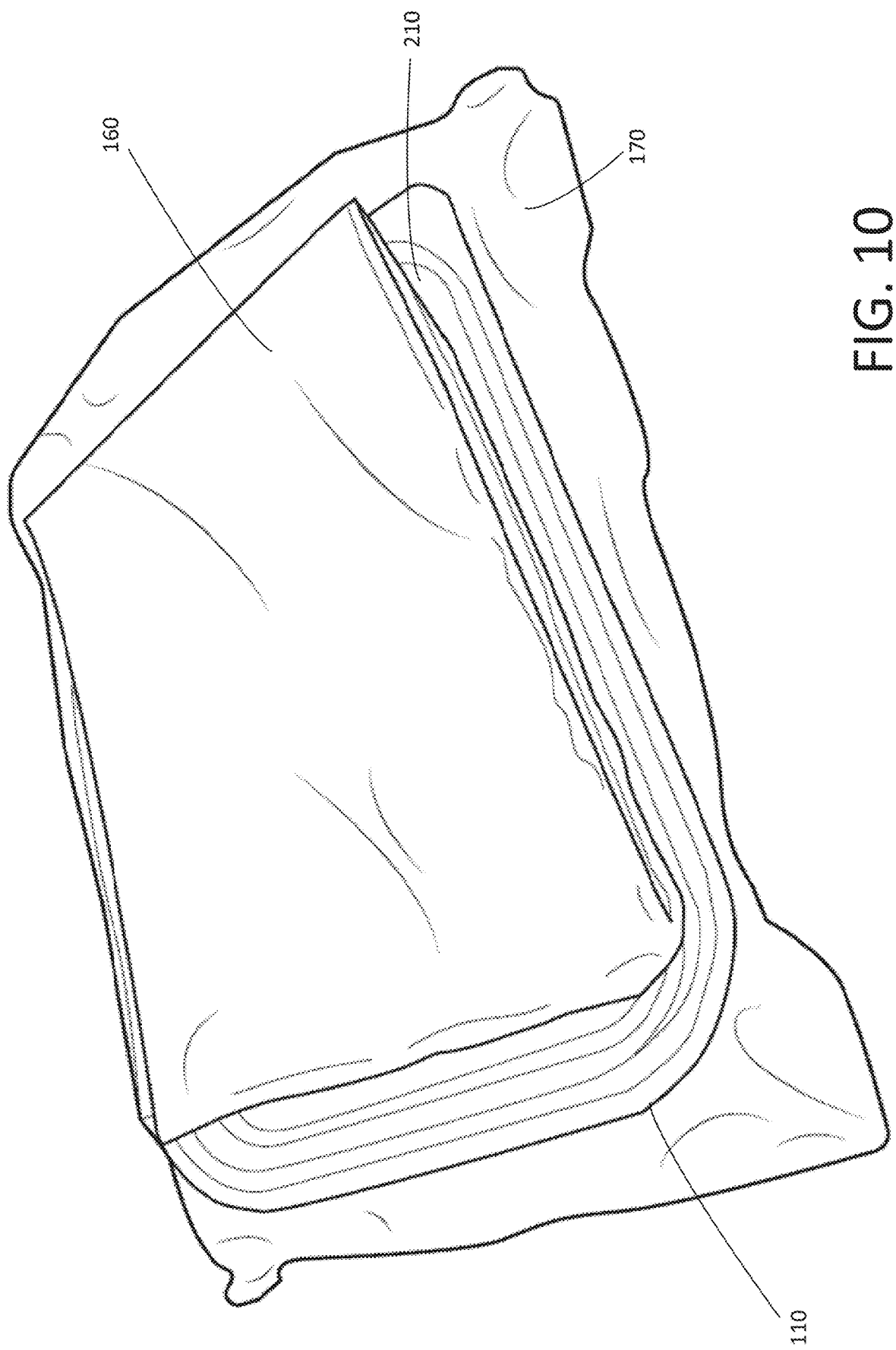
FIG. 10 shows a perspective view of the disposable packaging enclosing the disposable container (closed) and the disposable placemat, the disposable container containing the disposable gel containers, the disposable hair restraint, the disposable wipes, and the disposable gel applicator of the disposable kit shown in FIG. 1, according to various arrangements.

FIG. 8 shows a perspective view of the disposable container 110 (closed) containing the disposable gel containers 120*a* and 120*b*, the disposable hair restraint 130, the disposable wipes 140, and the disposable gel applicator 150, with the disposable placemat 160 placed on top of the disposable container 110 (closed), according to various arrangements. FIG. 9 shows a side view of the disposable container 110 (closed) containing the disposable gel containers 120*a* and 120*b*, the disposable hair restraint 130, the disposable wipe 140*s*, and the disposable gel applicator 150, with the disposable placemat 160 placed on top of the disposable container 110, according to various arrangements. FIG. 10 shows the disposable packaging 170 enclosing the disposable container 110 (closed) and the disposable placemat 160, the disposable container 110 contains the disposable gel containers 120*a* and 120*b*, the disposable hair restraint 130, the disposable wipes 140, and the disposable gel applicator 150, according to various arrangements.

Referring to FIGS. 1-10, the disposable packaging 170 can be made of a material that provides ingress protection against liquid (e.g., blood, sweat, and water) and particles (e.g., dust and hair) for the disposable placemat 160 and the items 120*a*, 120*b*, 130, 140, and 150 in the disposable container 110. An example of a relevant ingression protection rating met by the disposable packaging 170 is Ingression Protection Rating (IPxx). In some arrangements, the disposable packaging 170 is made of an elastic material that can be form-fitted to the disposable container 110 and the disposable placemat 160 when the disposable packaging 170 encloses the disposable container 110 and the disposable placemat 160. Furthermore, in some arrangements, the disposable packaging 170 is made from a biocompatible material suitable for contacting a human body. An example of a relevant biocompatibility standard met by the material of the disposable packaging 170 is the ISO 10993-1 standard. Moreover, in some arrangements, the disposable packaging 170 is made of a lightweight material or an ultra-lightweight material, for easy transportation and storage. The disposable packaging 170 can be made from a transparent material so that a healthcare provider can easily see whether the items stored in the disposable container 110 have already been used and whether the items stored in the disposable container 110 have been tampered with or spoiled. The disposable packaging 170 can be made from a material such as but not limited to, polyethylene, polypropylene, polycarbonate, polyurethane, polyetherimide, polyvinyl chloride, and polyether ether ketone. In other examples, the disposable packaging 170 can be made from a layer of thin silicone, biocompatible waterproof fibers or fabric, a medical curtain (e.g., a polyethylene curtain), treated paper, Tyvek®, and the like.

The disposable packaging 170 may include a fastening mechanism configured to close the disposable packaging 170 to form an enclosure to enclose the disposable placemat 160 and the disposable container 110 (with the items 120a, 120b, 130, 140, and 150 stored therein). The disposable packaging 170 can be opened via the fastening mechanism to create an opening through which the disposable placemat 160 and the disposable container 110 (with the items 120a, 120b, 130, 140, and 150 stored therein) can be removed. In some arrangements, the fastening mechanism is a sealing mechanism that forms a watertight seal and/or an airtight seal. Examples of the fastening mechanism include but are not limited to, adhesive, a zipper, a press seal, a string, zip-top, and a hook-and-loop fastener. In some arrangements, the disposable packaging 170 is welded or press-fitted over the disposable placemat 160 and the disposable container 110. In that regard, the disposable packaging 170 may have perforations suitable to be torn to access the disposable placemat 160 and the disposable container 110.

The disposable placemat 160 is outside of the interior of the disposable container 110. The disposable placemat 160 is between a portion of the disposable packaging 170 and the disposable container 110 when the disposable packaging 170 is unopened and encloses the disposable container 110 and the disposable placemat 160.

The disposable placemat 160 is shown to be in folded state and can be placed on top of the disposable container 110 (e.g., on the lid 210 of the disposable container 110). For example, the lid 210 has a concaved surface extending towards the interior of the disposable container 110. The concaved surface defines a concave space. As shown, the disposable placemat 160 can be folded and placed within the concave space. At least a portion of the disposable placemat 160 is within the concave space when the disposable packaging 170 is unopened and encloses the disposable container 110 and the placemat 160. In other arrangements, the disposable placemat 160 is housed within the disposable container 110 (e.g., the disposable container 110 has enough space or height to accommodate housing of the disposable placemat 160 along with the other items 120a, 120b, 130, 140, and 150 stored therein).

Examples of the disposable placemat 160 include those disclosed in U.S. patent application Ser. No. 15/923,906, titled Placemat System, filed on Mar. 16, 2018, which is hereby incorporated by reference in its entirety.

Figure 11A:
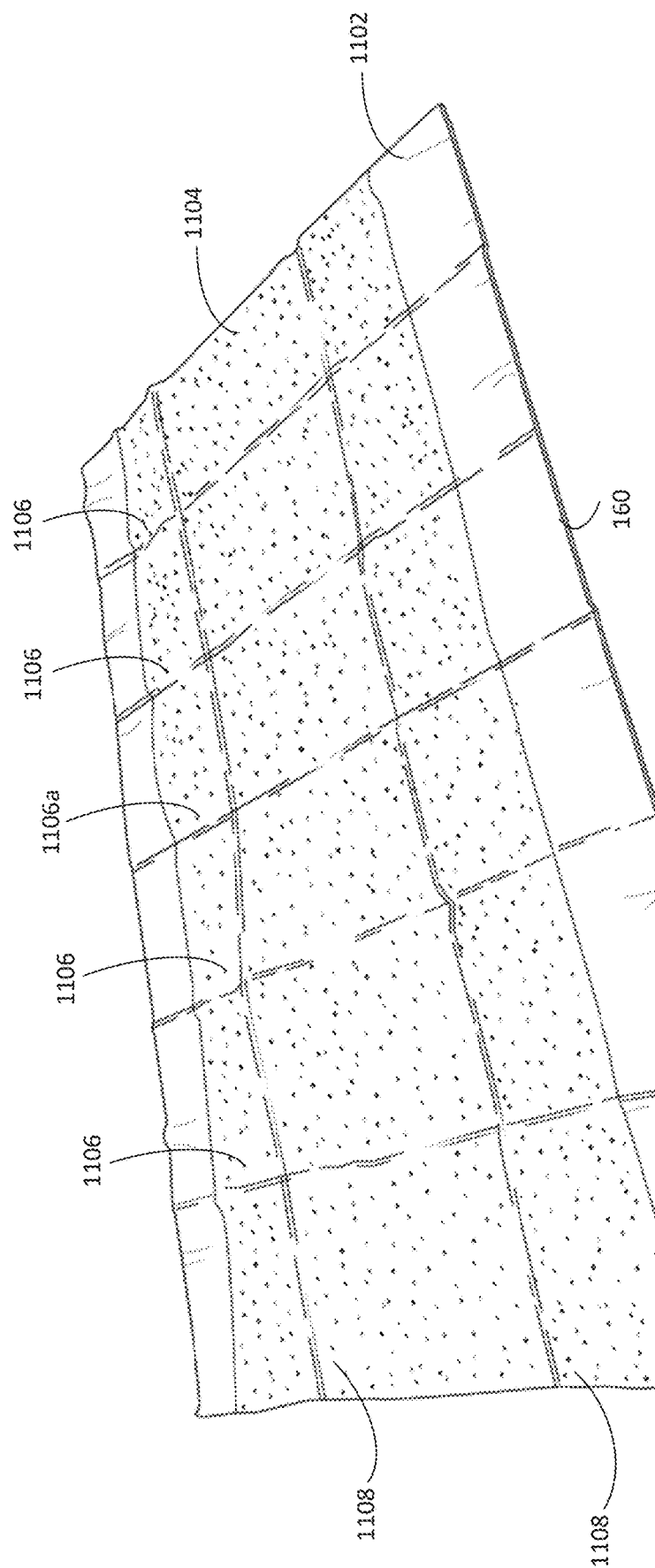
FIG. 11A shows a perspective view of the disposable placemat (unfolded) of the disposable kit shown in FIG. 1, according to various arrangements.
Figure 11C:
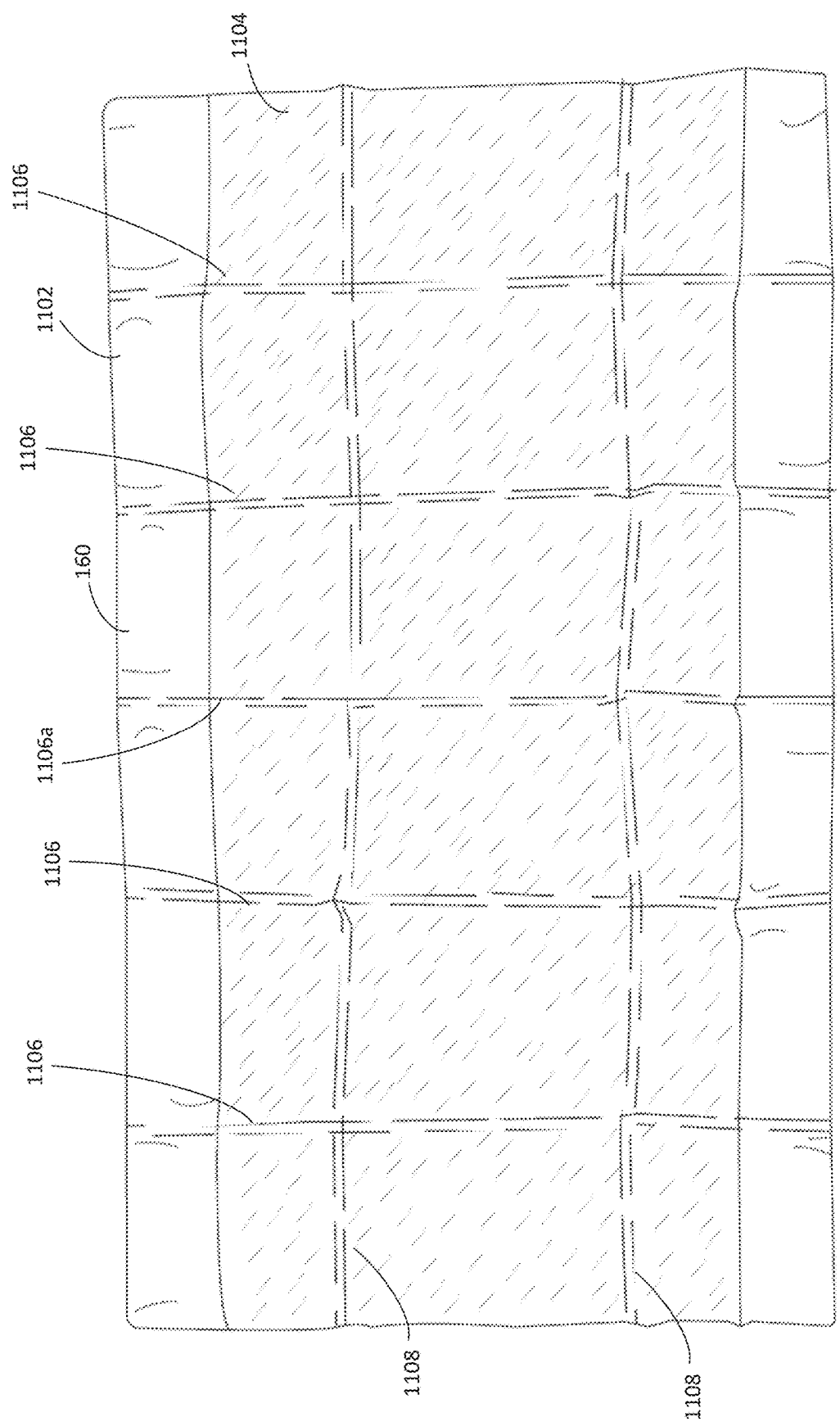
FIG. 11C shows a back view of the disposable placemat (unfolded) of the disposable kit shown in FIG. 1, according to various arrangements.
Figure 11D:
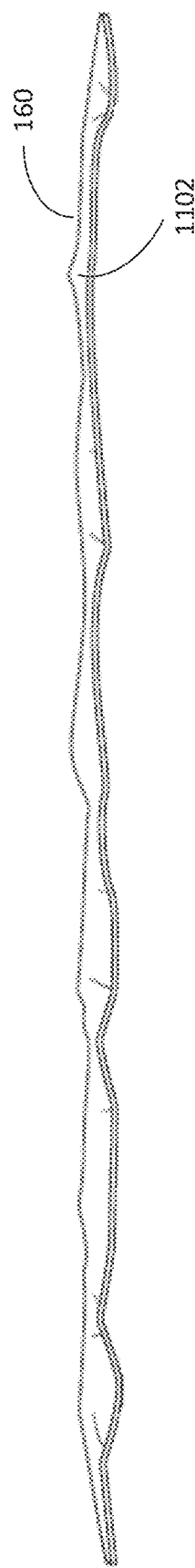
FIG. 11D shows a first side view of the disposable placemat (unfolded) of the disposable kit shown in FIG. 1, according to various arrangements.
Figure 11E:
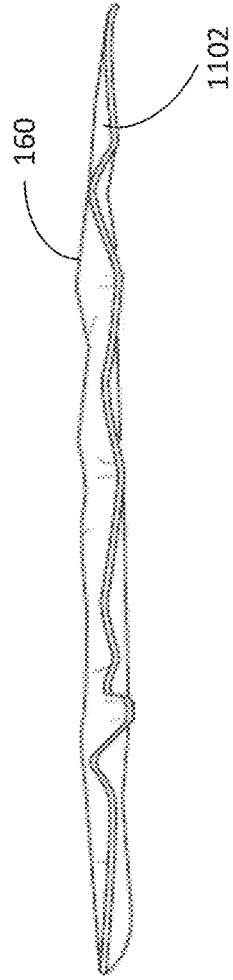
FIG. 11E shows a second side view of the disposable placemat (unfolded) of the disposable kit shown in FIG. 1, according to various arrangements.

FIG. 11A shows a perspective view of the disposable placemat 160 (unfolded), according to various arrangements. FIG. 11B shows a front view of the disposable placemat 160 (unfolded), according to various arrangements. FIG. 11C shows a back view of the disposable placemat 160 (unfolded), according to various arrangements. FIG. 11D shows a first side view of the disposable placemat 160 (unfolded), according to various arrangements. The first side view of the disposable placemat 160 shows a lengthwise dimension of the disposable placemat 160. The view corresponding to another, opposite lengthwise dimension of the disposable placemat 160 is similar to the first side view. FIG. 11E shows a second side view of the disposable placemat 160 (unfolded), according to various arrangements. The second side view of the disposable placemat 160 shows a widthwise dimension of the disposable placemat 160. The view corresponding to another, opposite widthwise dimension of the disposable placemat 160 is similar to the second side view. Referring to FIGS. 1-11E, in some arrangements, the folded disposable placemat 160 can be unfolded by a healthcare provider for use with respect to a subject in connection with a medical procedure, for example, involving ultrasound.

The disposable placemat 160 is made from a sheet of a first material 1102 and a sheet of a second material 1104. The first material 1102 includes any suitable flexible material, such as, but not limited to, fabric, plastic, and the like. In some arrangements, the first material 1102 is a stretchable or elastic material. In some arrangements, the first material 1102 includes a slick material or is coated with a slick material to allow frictionless movement along a surface. For example, the first material 1102 can be made from or coated with a water-repellent material, hydrophobic material, or a superhydrophobic (nanoscopic surface) material. In some examples, the first material 1102 is slippery to allow the frictionless movement of an object (e.g., a head of a subject, a medical instrument, and the like) on the surface of the first material 1102. Examples of the first material 1102 include, but are not limited to, polytetrafluoroethylene, waterproof composite fabric, and the like. In some arrangements, the second material 1104 is made from any suitable soft, absorbent material, such as, but not limited to, paper, cotton, rayon, polyester, polyethylene, polypropylene, fiber, sponge, polyethylene terephthalate, wood pulp, combinations thereof, and the like. In particular arrangements, the second material 1104 is made from a soft material that is configured to cushion a subject when placed thereon for added comfortability of the subject. In that regard, the sheet of the second material 1104 may have a suitable thickness for providing the cushion. In some arrangements, both the first material 1102 and the second material 1104 are made from a relatively inexpensive material such that the disposable placemat 160 can be mass-produced and disposed of after a single use.

In some arrangements, the second material 1104 is configured to be absorbent with respect to one or more fluids so as to aid in healthcare administration by, for example, cleaning a subject or equipment before, during, or after a medical procedure. In some arrangements, fluids that are used in a medical procedure can be absorbed by the sheet of the second material 1104. Examples of the fluids include, but are not limited to, an ultrasound gel, disinfectants (rubbing alcohol or another liquid disinfectant), water, and the like. In some arrangements, bodily fluids from a patient can be absorbed by the sheet of the second material 1104. Examples of the bodily fluids include, but are not limited to, blood, urine, vomit, fecal matter, pus, saliva, and the like. For example, the sheet of second material 1104 can have a large enough area to encompass a body of an infant or toddler that can be placed on the sheet of second material 1104 for medical examination or procedure, and any fluids discharged from the infant or toddler or used in connection with the medical examination or procedure can be absorbed by the sheet of the second material 1104.

In some arrangements, using the disposable placemat 160 in the manner disclosed allows a work surface for the medical examination or procedure on which the disposable placemat 160 is positioned to remain clean and sterile from subject to subject, resulting in increased infection control and higher quality medical care. For example, in the case where a subject has experienced mild traumatic brain injury and is to undergo a brain diagnostic (e.g., Transcranial Doppler) to confirm, the subject may be bleeding from the experience and the disposable placemat 160 can be used to form a barrier between the patient and a surface (e.g., a surface of a table, a bed, the ground, and the like) on which medical procedures occur such that the surface can remain sterile from such bodily fluids. In addition, the sheet of second material 1104 can be utilized to help absorb and clean the blood from the patient.

In some arrangements, the sheet of the second material 1104 is configured to retain or absorb fluids that are involved in different medical procedures. For example, in some situations in which the subject is bleeding, the sheet of the second material 1104 is configured to have sufficient absorbency, thickness, and size to be capable of wiping and retaining the blood from the subject so that the medical procedure can be properly performed. In such arrangements, the sheet of the second material 1104 is made from materials capable of absorbing or retaining blood, such as, but not limited to, cotton, rayon, polyester, polyethylene, polypropylene, combinations thereof, and the like.

As another example, in some situations in which fluids (e.g., such as but not limited to, ultrasound gel for facilitating ultrasound signal propagation from an ultrasound probe into a subject's body) are used in conjunction with a medical procedure, the sheet of the second material 1104 is configured to have sufficient absorbency, thickness, and size to be capable of wiping, retaining, and/or absorbing the ultrasound gel from the subject during or after the medical procedure. Accordingly, in some arrangements, the sheet of the second material 1104 aids in the administration of healthcare by allowing a user to clean the patient of any medical fluids (e.g., ultrasound gel) with edges or corners of the sheet of the second material 1104 or physically guide the fluid applied to the patient or a piece of medical equipment to optimal locations, by a user via the sheet of the second material 1104, for increasing the effectiveness of the medical procedure (e.g., the ultrasound gel can be physically directed and constrained, via use of the sheet of the second material 1104, to an acoustic window at a subject's head that is optimal for receiving the ultrasound signal). Accordingly, in some arrangements, the sheet of the second material 1104 is made from materials capable of absorbing or retaining ultrasound gel, such as, but not limited to, wood pulp, resin, paper sheets, cotton, polyester, rayon, polyethylene, polypropylene, combinations thereof, and the like.

In some arrangements, the sheet of the first material 1102 is fluid-impermeable so that fluids that are absorbed by the sheet of the second material 1104 do not pass beyond the sheet of first material 1102, providing increased infection control because the fluids are contained within the disposable placemat 160 that can be disposed of. For example, the surface upon which the disposable placemat 160 is positioned can remain sterile and clean due to the fluid impermeable first material 1102. Any other objects are also protected as the disposable placemat 160 is disposed of since the first material 1102 will not allow leakage of fluid outside of the disposable placemat 160 (e.g., when the disposable placemat 160 is cinched or folded up for disposal). In other arrangements, the second material 1104 is made from any suitable fluid impermeable material, such as, but not limited to, glass, plastic, metal, polytetrafluoroethylene, coated fabrics, silicone, polyurethane, rubber, rubber-coated textiles, combinations thereof, and the like. Furthermore, the sheet of the first material 1102 and the sheet of the second material 1104 have any suitable thickness to be sufficiently thin for storage (e.g., when folded up).

In some arrangements, the first material 1102 has a larger surface area than that of the second material 1104. In some arrangements, the second material 1104 has a thickness greater than that of the first material 1102. The first material 1102 is affixed to the second material 1104 by any suitable and secure method, such as, but not limited to, by adhesive (e.g., hot-melt glue), by thermo-forming, by sewing, by molding, by welding, by Velcro, by stapling, and the like. In some arrangements, the second material 1104 extends along an entire length of the first material 1102, but not along an entire width of the first material 1102, or vice versa. The length of the first material 1102 is greater than the width of the first material 1102. In other arrangements, the second material 1104 extends along the entire width and the entire length of the first material 1102. In other arrangements, all sides of the sheet of the second material 1104 are encompassed by the sheet of the first material 1102 (e.g., the sheet of the second material 1104 has a square shape within the larger rectangular sheet of the first material 1102). In some arrangements, the disposable placemat 160 is designed to have a rectangular shape. In other arrangements, the disposable placemat 160 is designed to have any suitable shape (such as, but not limited to, a circle, a triangle, a hexagon, and the like) for receiving a patient or a specific body part of the patient.

In some arrangements, the disposable placemat 160 has any suitable size for receiving a body part or the entire body of a patient. For example, in arrangements where the disposable placemat 160 is configured to receive a head of a patient, the sheet of the first material 1102 can have a length in a range of about 30 centimeters (cm) to about 95 cm and a width in a range of about 25 cm to about 65 cm. In such arrangements, the sheet of the second material 1104 can have a length in a range of about 30 cm to about 95 cm and a width in a range of about 20 cm to about 50 cm. In such arrangements, the sheet of the second material 1104 has a size and position at the sheet of the first material 1102 such that a first strip of the first material 1102 is located above the sheet of the second material 1104 and a second strip of the second material 1104 is located below the sheet of the first material 1102 (e.g., the non-limiting configuration shown in FIG. 1). In some arrangements, the first strip and the second strip of the first material 1102 has the same width, which is in a range from about 4 cm to about 9 cm. In some arrangements, the sheet of the second material 1104 has any suitable weight for absorbing and cushioning a patient, such as, but not limited to, in a range from about 50 grams per square meter (gsm) to about 110 gsm. In some arrangements, the sheet of the second material 1104 has any suitable absorbency characteristic for absorbing fluids thereon, such as absorbency in a range of about 4 grams of fluid to about 30 grams of fluid (e.g., blood or ultrasound gel). The absorbency can be a measurement of how much fluid the second material 1104 holds before leaking therefrom, as determined by, for example, the Syngina Test.

As shown, the disposable placemat 160 is foldable (e.g., for simple and easy storage and disposal thereof). In some arrangements, the disposable placemat 160 includes at least one vertical folding guide 1106 and at least one horizontal folding guide 1108. In some arrangements, the folding guides 1106, 1108 provide sections along which the disposable placemat 160 can be folded such that the disposable placemat 160 can be folded into a smaller form factor to allow convenient, easy storage and transportation of the disposable placemat 160, for instance, to be supported on the lid 210 of the disposable container 110. For example, the disposable placemat 160 includes a plurality of vertical folding guides 1106 and/or a plurality of horizontal folding guides 1108. The disposable placemat 160 includes any desired number and orientation of vertical folding guides 1106 and horizontal folding guides 1108 to facilitate suitable miniaturization of the disposable placemat 160.

In some arrangements, the second material 1104 or an additional material between the first material 1102 and the second material 1104 is or includes a cushioning material for providing a comfortable experience to a patient. In particular arrangements, the cushioning material is concentrated in a substantially central portion of the disposable placemat 160. For example, the cushioning material can be located between the two vertical folding guides 1106 directly surrounding a center vertical line of the disposable placemat 160 (e.g., the center vertical line in an example may fall along the central vertical folding guide 1106a). In other arrangements, the cushioning material is located over an entirety of the second material 1104.

In some arrangements, the sheet of the second material 1104 is pre-soaked or treated with a compound configured to be a disinfectant or to kill bacteria. In particular arrangements, the second material 1104 is pre-soaked or treated with, for example, but not limited to, alcohol, ethanol, isoproponal, dodecanoic acid, triclosan, triclocarban, a combination thereof, and the like. In some arrangements, the compound at the second material 1104 is safe to contact skin of the subject. In some arrangements, an extra layer of a disposable thin film is applied to the patient-facing surface of the sheet of the second material 1104 such that the film prolongs the lifespan of the treated second material 1104 such that the compound therein does not dry out during storage. In other arrangements, the back surface of the sheet of the first material 1102 (e.g., the surface that is opposite to the surface connected to the sheet of the second material 1104) is treated with the compound such that when the disposable placemat 160 is positioned on a work surface, the work surface is disinfected for increased sterility and hygiene. When the disposable placemat 160 is positioned on the work surface, the back surface comes in contact with the work surface. For example, another sheet of the second material 1104 can be affixed to the back surface of the sheet of the first material 1102 and pre-soaked or treated with a disinfecting or antibacterial compound. Accordingly, by including a layer of disinfecting or antibacterial compound on the back surface of the sheet of the first material 1102, the disposable placemat 160 also serves as a sterilization apparatus that sterilizes the work surface on which the disposable placemat 160 is positioned (e.g., a medical examination bed, gurney, table, and so on). Furthermore, by including a layer of disinfecting or antibacterial compound on the back surface of the sheet of the first material 1102, the chemical compound does not contact the skin of the subject, which may otherwise cause irritation to the subject (e.g., for those chemical compounds that are not recommended or safe to contact subject's skin). In other arrangements, the disinfecting or antibacterial compound is included at both the front and back surfaces of the disposable placemat 160.

Accordingly, FIGS. 2-10 illustrate a sequence by which the disposable kit 100 is assembled or otherwise provided, as described. In one example, the disposable gel containers 120a and 120b are first placed in the disposable container 110. Next, the disposable hair restraint 130 is placed in the disposable container 110. Next, the disposable wipes 140 are placed in the disposable container 110. Next, the gel applicator 150 is placed in the disposable container 110. Next, the disposable container 110 is closed. Next, the disposable placemat 160 is placed on the lid 210 of the disposable container 110. Next, the disposable container 110 with the disposable placemat 160 are placed in the disposable packaging 170. In another example, the disposable hair restraint 130 is first placed in the disposable container 110. Next, the disposable gel containers 120a and 120b are placed in the disposable container 110. Next, the disposable wipes 140 are placed in the disposable container 110. Next, the gel applicator 150 is placed in the disposable container 110. Next, the disposable container 110 is closed. Next, the disposable placemat 160 is placed on the lid 210 of the disposable container 110. Next, the disposable container 110 with the disposable placemat 160 are placed in the disposable packaging 170. In yet another example, the disposable hair restraint 130 is first placed in the disposable container 110. Next, the disposable wipes 140 are placed in the disposable container 110. Next, the disposable gel containers 120a and 120b are placed in the disposable container 110. Next, the gel applicator 150 is placed in the disposable container 110. Next, the disposable container 110 is closed. Next, the disposable placemat 160 is placed on the lid 210 of the disposable container 110. Next, the disposable container 110 with the disposable placemat 160 are placed in the disposable packaging 170. In various arrangements, other suitable sequences by which the disposable kit 100 is assembled can be likewise implemented.

FIG. 10 to FIG. 2, in that order, illustrate a sequence by which the disposable kit 100 is used by a healthcare provider for an ultrasound medical procedure according to some arrangements. To begin, the healthcare provider retrieves the disposable kit 100 (shown in FIG. 10) and removes the disposable packaging 170. After the disposable packaging 170 is removed, the disposable container 110 and the disposable placemat 160 are accessible as show in FIGS. 8 and 9. The disposable placemat 160 is placed outside of and on top of the disposable container 110 (e.g., on top of the lid 210 of the disposable container 110) because the healthcare provider typically needs to unfold and deploy the disposable placemat 160 to allow the subject to lay down on the disposable placemat 160, before beginning or otherwise preparing the medical procedure. Therefore, the disposable placemat 160 is placed in the most accessible position as the disposable packaging 170 is removed. The accessibility of the disposable placemat 160 is significant especially in emergency situations when the subject needs to lie down quickly.

As shown in FIG. 7, after the disposable placemat 160 is removed, the unopened disposable container 110 is revealed. The disposable container 110 provides additional ingress protection to the items 120a and 120b, 130, 140, and 150, reducing bacteria, liquid, and particles from entering into the disposable container 110. Upon opening the lid 210 of the disposable container 110 as shown in FIG. 6, the healthcare provider retrieves the disposable gel applicator 150. As shown in FIG. 5, after the disposable gel applicator 150 is removed, the disposable gel containers 120*a* and 120*b* and the disposable wipes 140 become accessible. The healthcare provider can then retrieve the disposable wipes 140, the disposable hair restraint 130, and the disposable gel containers 120*a* and 120*b*, as shown in FIG. 4 to FIG. 2, in any suitable order. For example, the healthcare provider can open the disposable gel containers 120*a* and 120*b* to access the gel stored therein and apply the gel using the gel applicator 150. The healthcare provider can tie the hair of the subject using the disposable hair restraint 130. The healthcare provider can wipe excess gel or bodily fluid of the subject using the disposable wipes 140.

In some examples, after the disposable gel applicator 150 (which holds the items 120*a* and 120*b*, 130, 140 in place when the lid 210 is closed) is removed from the disposable container 110, the healthcare provider may first use the disposable wipes 140 to wipe off bodily fluid (e.g., blood and sweat) from the subject, to clean the area on which the gel is to be applied. Then, the healthcare provider may use the disposable hair restraint 130 to tie the hair of the subject. Thereafter, the healthcare provider may open the disposable gel containers 120*a* and 120*b* to access the gel stored therein and apply the gel using the gel applicator 150. The healthcare provider may use some of the disposable wipes 140 to wipe off excessive gel applied. As such, the subject is prepared for the medical procedure involving ultrasound. After the procedure, the healthcare provider may use some of the disposable wipes 140 to wipe off the gel applied.

In some arrangements, after removal and use of one or more of the items 120*a*, 120*b*, 130, 140, 150, and 160, a user can place the used items back into the disposable container 110. Accordingly, the disposable container 110 containing the used items can be thrown away easily, safely, and such that the used items 120*a*, 120*b*, 130, 140, 150, and 160 are prevented from contacting anything outside of the disposable container 110. As such, the disposable container 110 not only can be used as a barrier for preventing ingress therein (e.g., to protect the items 120*a*, 120*b*, 130, 140, and 150), but can also be used to safely and hygienically dispose of the items 120*a*, 120*b*, 130, 140, 150, and 160 after use by resealing them in the disposable container 110 such that the items 120*a*, 120*b*, 130, 140, 150, and 160 do not contaminate any surrounding objects or people. For further protection of the surrounding environment, a user can place the used items 120*a*, 120*b*, 130, 140, 150, and 160 into the disposable container 110 and then place the filled disposable container 110 in the disposable packaging 170 before disposing of everything. Accordingly, in some arrangements, the disposable kit 100 provides a mechanism for maintaining medically safe and uncontaminated items housed therein and for preventing contamination of the surrounding environment once the items of the disposable kit 100 are used and transported for disposal.

Accordingly, FIGS. 1-11E show an example of a disposable kit (e.g., the disposable kit 100) configured to be used for a medical procedure (e.g., an ultrasound procedure) in connection with a device (e.g., an ultrasound device having one or more probes).

FIGS. 12-22H show another example of a disposable kit (e.g., a disposable kit 1200) configured to be used for a medical procedure (e.g., an ultrasound procedure) in connection with a device (e.g., an ultrasound device having one or more probes). According to various arrangements, the disposable kit 1200 is disposable. The disposable kit 1200 includes a plurality of different disposable medical items such that the disposable kit 1200 and the items therein are not reused between subjects and between medical procedures. As such, hygiene and cleanliness of an environment are increased, while allowing healthcare providers to more efficiently and easily administer healthcare.

Figure 12:
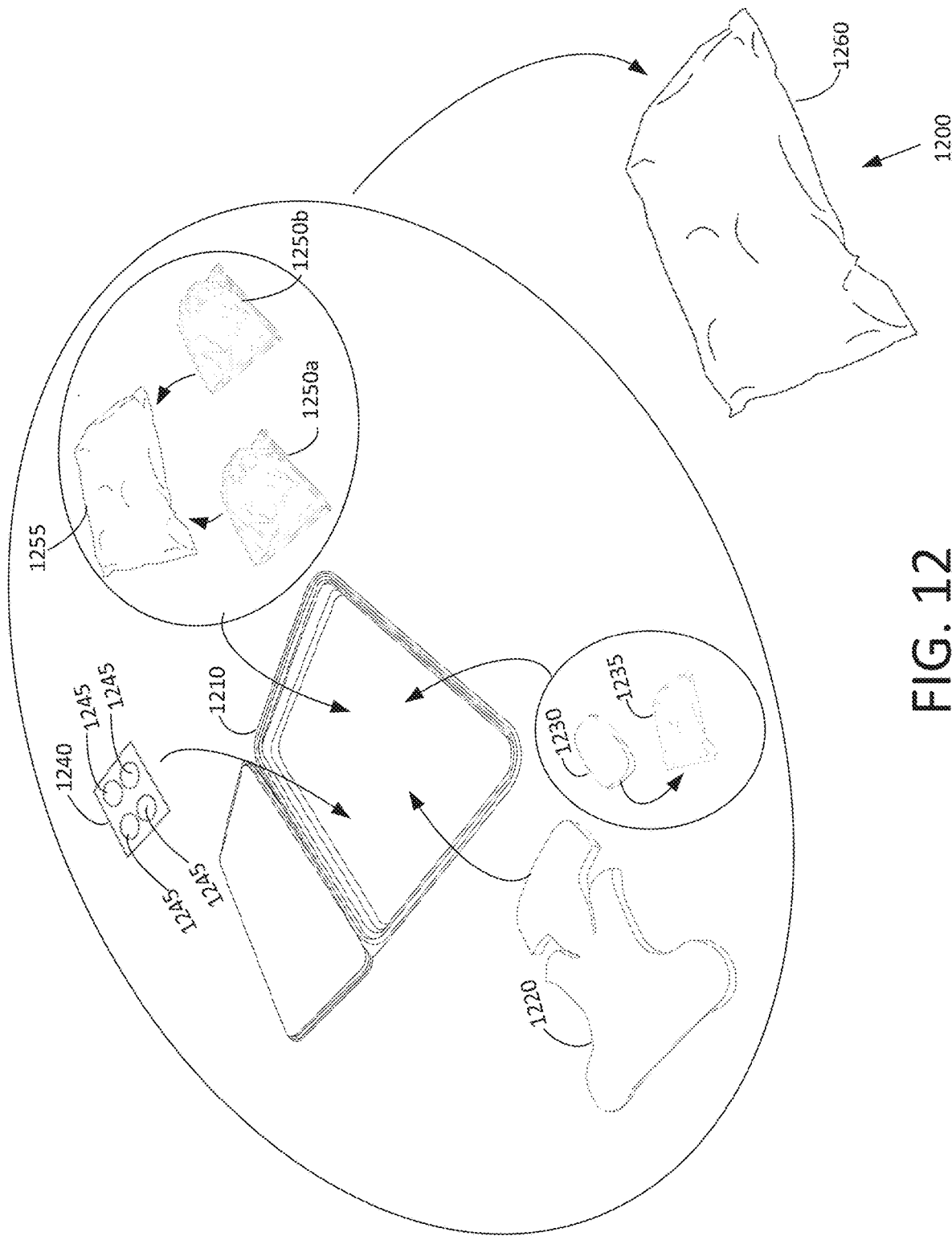
FIG. 12 shows components of an example of a disposable kit, according to various arrangements.

FIG. 12 shows components of an example of the disposable kit 1200, according to various arrangements. Referring to FIG. 12, the disposable kit 1200 includes a disposable container 1210, a head cradle pad 1220, a head restraint pad 1230, a sheet 1240 with fiducial markers 1245, at least one disposable enclosure (e.g., disposable enclosures 1250*a* and 1250*b*), and disposable packaging 1260. The head cradle pad 1220 is configured to be placed on a head cradle of the robotic device. The head restraint pad 1230 is configured to be placed on a head restraint of the robotic device. The fiducial markers 1245 are configured to facilitate registration or alignment of the robotic device. The disposable enclosures 1250*a* and 1250*b* are configured to enclose at least a portion of the robotic device to provide ingress protection. The disposable kit 1200 further includes enclosures 1235 and 1255, to enclose the head restraint pad 1230 and the disposable enclosures 1250*a* and 1250*b*, respectively. In some arrangements, one or more of the items 1220, 1230, 1235, 1240, 1245, 1250*a*, 1250*b*, and 1255 in the disposable container 1210 are sterilized before being placed into the disposable container 110. In some arrangements, the disposable container 1210 and the disposable packaging 1260 are sterilized.

In some arrangements, the disposable container 1210 is configured to store or otherwise contain the disposable container 1210, the head cradle pad 1220, the head restraint pad 1230, the sheet 1240 with the fiducial markers 1245, the disposable enclosures 1250*a* and 1250*b*, and the enclosures 1235 and 1255. The disposable container 1210 can be opened to allow a healthcare provider to retrieve or otherwise access the medical items 1220, 1230, 1235, 1240, 1245, 1250*a*, 1250*b*, and 1255 in the disposable container 1210. The disposable container 1210 can be closed to enclose the items 1220, 1230, 1235, 1240, 1245, 1250*a*, 1250*b*, and 1255.

In some arrangements, the disposable kit 1200 includes no more and no fewer types of medical items than the types of medical items shown in FIG. 12. For example, the disposable kit 1200 may include no more and no fewer than head cradle pad(s) (e.g., the head cradle pad 1220), head restraint pad(s) (e.g., the head restraint pad 1230), sheet(s) with fiducial markers (e.g., the sheet 1240 with the fiducial markers 1245), disposable enclosure(s) (e.g., the disposable enclosures 1250*a* and 1250*b*), and enclosure (e.g., the enclosures 1235 and 1255). In other arrangements, the disposable kit 1200 includes more or fewer amounts and/or types of items than the amounts and types shown in FIG. 12. In some arrangements, the disposable kit 1200 includes any suitable amount or number of each item type.

In some arrangements, the item types in the disposable kit 2100 and the number of items for each item type in the disposable kit 1200 are just enough for a medical procedure involving ultrasound (such as but not limited to, an ultrasound scan) for a single patient or subject, using the robotic device. In other words, the selection of the items in the disposable kit 1200 includes the appropriate number and types of items that can be used on a single subject for a single ultrasound procedure in connection with the robotic device, without the need to open an additional disposable kit and without wasting any unused items in the disposable kit 1200. As an example, the disposable kit 1200 includes the head cradle pad 1220 and the head restraint pad 1230, sufficient to be deployed onto the head cradle and the head restraint of the robotic device, respectively, for a single subject for a single medical operation. The disposable kit 1200 further includes the four fiducial markers 1245, just enough for a single subject for a single medical operation. In one example, for each side of the subject's face, one of the fiducial markers 1245 can be disposed at a particular landmark at a subject's head (e.g., at a corner of a subject's eye), and one of the fiducial markers 1245 can be disposed at another landmark at the subject's head (e.g., at a tragus of the subject), as shown in FIG. 21E. The disposable kit 1200 further includes the two disposable enclosures 1250a and 1250b, each of which encloses one of two robotic pods 2106a and 2106b of a robotic device 2102 as shown in FIGS. 21C and 21D.

Figure 13:
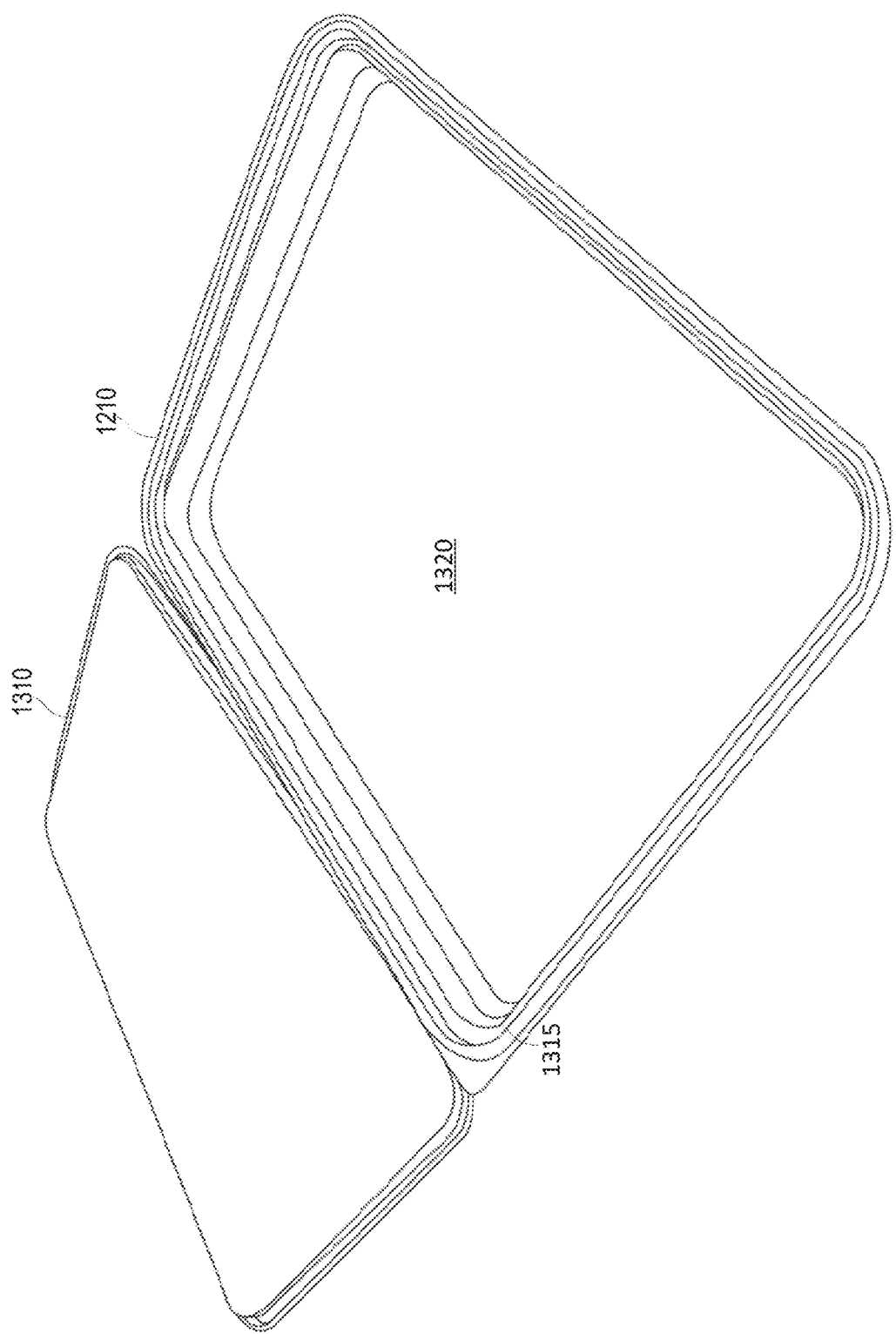
FIG. 13 shows a perspective view of the disposable container (opened) of the disposable kit shown in FIG. 12, according to various arrangements.

FIGS. 13-19 illustrate a method by which the disposable kit 1200 is manufactured or otherwise assembled. FIG. 13 shows a perspective view of the disposable container 1210 (opened) of the disposable kit 1200, according to various arrangements. Referring to FIGS. 12-13, the disposable container 1210 is light-weight for easy transportation and storage. In some examples, the disposable container 1210 can be made from an inexpensive material, having sufficient rigidity to hold its shape, and suitable for mass production. The disposable container 1210 can be made from a transparent or translucent material such that the healthcare provider can easily see whether the items stored in the disposable container 1210 have already been used and whether the items stored in the disposable container 1210 have been tempered with or spoiled. In that regard, the disposable container 1210 can be made from a plastic material such as but not limited to, polyethylene, polypropylene, polystyrene, and the like. In other examples, the disposable container 1210 can be made from glass, paperboard, ceramic, and the like. The disposable container 1210 may have some similar or same attributes to those of the disposable container 110 described above.

As shown, the disposable container 1210 includes a bottom portion 1315. The bottom portion 1315 includes a bottom surface 1320 and side walls extending from the bottom surface 1320. The bottom surface 1320 supports the items 1220, 1230, 1235, 1240, 1245, 1250a, 1250b, and 1255.

The disposable container 1210 includes a lid 1310. The lid 1310 is configured to be opened to provide access to an interior of the disposable container 1210. The interior of the container 1210 is defined by the bottom portion 1315 (e.g., by the side walls and the bottom surface 1320). The lid 1310 has an interior surface facing the interior of the container 1210 when the lid 1310 is closed. The interior surface of the lid 1310 faces the bottom surface 1320 when the lid 1310 is closed. As shown, the lid 1310 can mate with the bottom portion 1315 via friction fit. In other examples, the lid 1310 can mate with the bottom portion 1315 via one or more of a zipper, buttons, a press seal, a re-sealable seal (e.g., a zip-top), adhesives, latches, strings, and the like. In some arrangements, the lid 1310 and the bottom portion 1315 are connected by one or more hinges. In other arrangements, the lid 1310 and the bottom portion 1315 are separate and are not connected. In some arrangements, the lid 1310 and the bottom portion 1315 can form a water-tight seal or air-tight seal to provide ingress protection, thus maintaining the cleanliness of the items 1220, 1230, 1235, 1240, 1245, 1250a, 1250b, and 1255 and reducing bacteria count within the interior of the disposable container 1210 when the lid 1310 is closed. In some arrangements, the disposable container 1210 is sealed shut between the lid 1310 and the bottom portion 1315 so that the items 1220, 1230, 1235, 1240, 1245, 1250a, 1250b, and 1255 therein are secured, and such that a healthcare provider can readily determine whether the disposable container 1210 has been tampered with prior to use, in which case the healthcare provider can simply use another disposable kit 1200. For example, the disposable container 1210 can be sealed with a tape such that it is readily apparent whether the tape has been previously released, cut, or otherwise opened.

Figure 14:
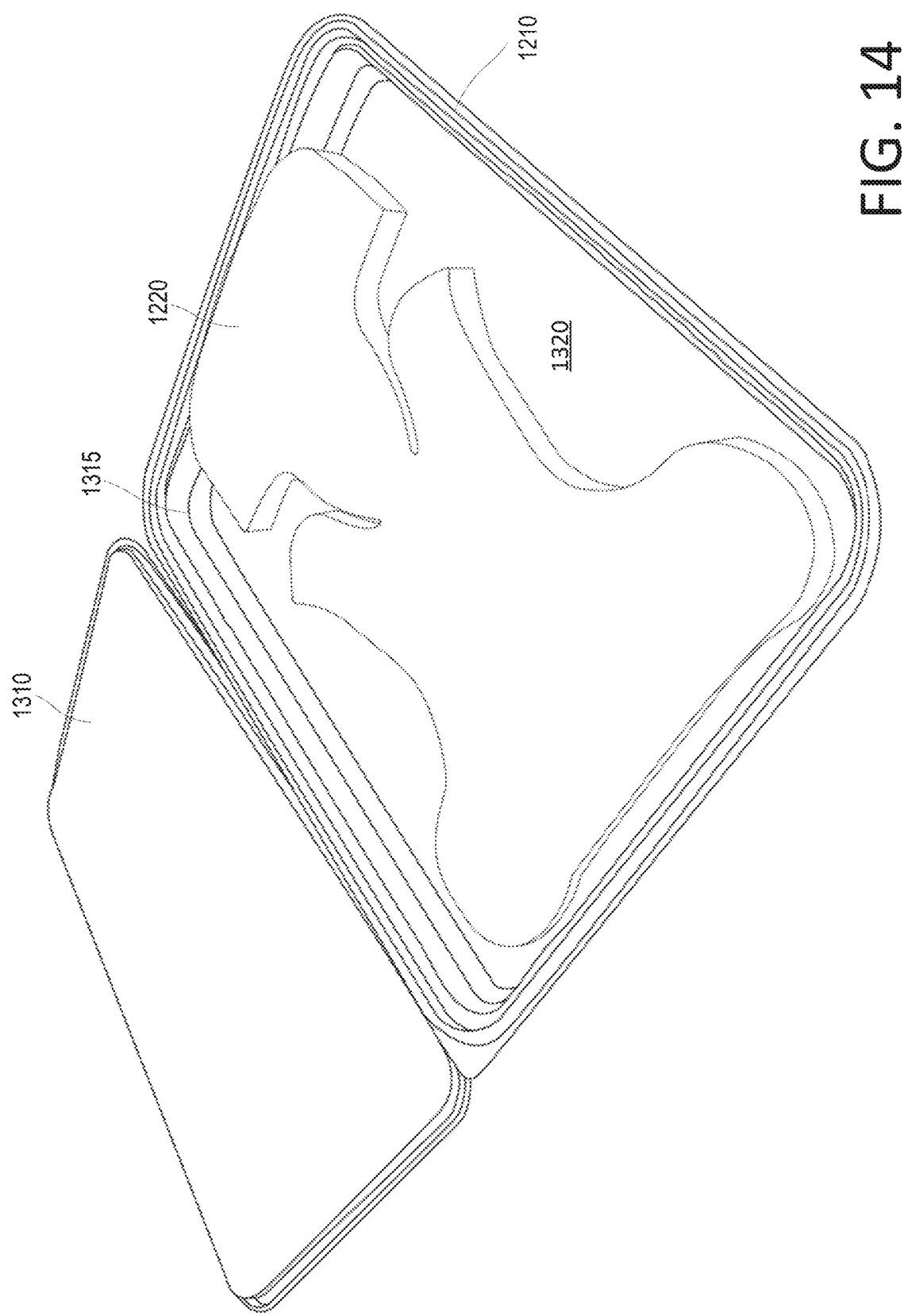
FIG. 14 shows a perspective view of the disposable container (opened) containing a head cradle pad of the disposable kit shown in FIG. 12, according to various arrangements.

FIG. 14 shows a perspective view of the disposable container 1210 (opened) containing the head cradle pad 1220 of the disposable kit 1200, according to various arrangements. Referring to FIGS. 12-14, the head cradle pad 1220 is configured to be placed on a head cradle (e.g., a head cradle 2108 of FIGS. 21A, 21C, and 21D) of a robotic device (e.g., the robotic device 2102 of FIGS. 21C and 21D). For example, as discussed in further detail herein, a back surface of the head cradle pad 1220 can include an adhesive layer (e.g., an adhesive layer 2008 of FIGS. 20A and 20C-20F) such that the head cradle pad 1220 can be releasably affixed to the head cradle so that the head cradle pad 1220 is temporarily attached to the head cradle of the robotic device.

The head cradle pad 1220 is made from any suitable soft material for receiving and cushioning a back of a head of a subject. In some arrangements, the head cradle pad 1220 is suitably shaped and flexible enough to fit within and contour to the head cradle, as further described herein. In that regard, the head cradle pad 1220 is or includes padding for providing comfort to the head of the subject. In some arrangements, the head cradle pad 1220 is made from any suitable soft material, such as, but not limited to, closed cell foam, open cell foam, self-skinning open or closed cell foams, cast, aerated, extruded silicone or urethane, polyurethane gels that are configured to distribute pressure efficiently, or the like. In some arrangements, the head cradle pad 1220 has any suitable firmness for supporting the head of the subject, such as, but not limited to, in a range of about 0.1 pound per square inch (psi) to about 60 psi (e.g., in a range of about 0.1 psi to about 10 psi) or within other suitable ranges of firmness. In some arrangements, the head cradle pad 1220 has memory for expanding to fit contours of the head of the subject. In some arrangements, the head cradle pad 1220 can be compressed and expands after the head of the subject is placed in the head cradle so that the padding expands around the head to better secure and cushion the head.

Dimensions (e.g., a length and width) of the bottom surface 1320 and the side walls of the bottom portion 1315 are equal to or slightly greater than dimensions (e.g., a length-wise dimension and a width-wise dimension) of the head cradle pad 1220, such that the head cradle pad 1220 fits snugly into the space defined by the bottom surface 1320 and the side walls of the bottom portion 1315. Due to that the head cradle pad 1220 is made of soft material (e.g., a pad layer 2005), the dimensions of the bottom surface 1320 can be sized such that the head cradle pad 1220 (e.g., the pad layer 2005) is compressed along the length-wise dimension and the width-wise dimension as the head cradle pad 1220 is being placed in the disposable container 1210, and expands against the side walls after the head cradle pad 1220 has been placed in the disposable container 1210.

Figure 15:
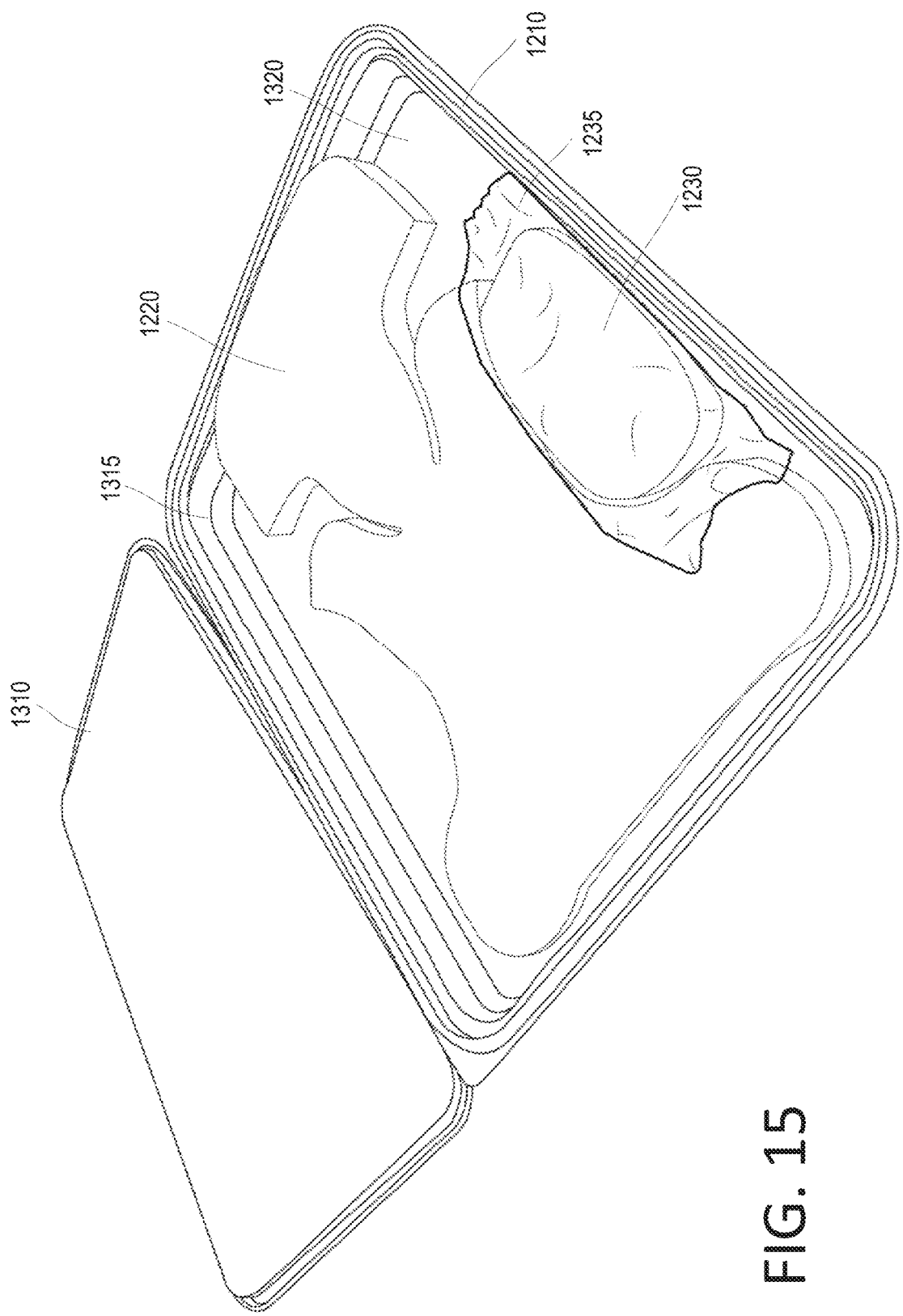
FIG. 15 shows a perspective view of the disposable container (opened) containing the head cradle pad and a head restraint pad of the disposable kit shown in FIG. 12, according to various arrangements.

FIG. 15 shows a perspective view of the disposable container 1210 (opened) containing the head cradle pad 1220 and the head restraint pad 1230 of the disposable kit 1200, according to various arrangements. Referring to FIGS. 12-15, the head restraint pad 1230 is configured to be placed on a head restraint (e.g., a head restraint 2110 of FIGS. 21B and 21C) of a robotic device (e.g., the robotic device 2102 of FIGS. 21C and 21D). For example, as discussed in further detail herein, a back surface of the head restraint pad 1230 can include an adhesive layer (similar to the adhesive layer 2008) such that the head restraint pad 1230 can be releasably affixed to the head restraint so that the head restraint pad 1230 is temporarily attached to the head restraint of the robotic device. As shown, the head restraint pad 1230 is placed in the enclosure 1235 for additional ingress protection. The enclosure 1235 may be an enclosure such as, but not limited to, the disposable packaging 170. The enclosure 1235 has a suitable size configured to form-fit or otherwise enclose the head restraint pad 1230.

The head restraint pad 1230 is made from any suitable soft material for contacting, cushioning, and applying pressure against a front of a head (e.g., a forehead) of a subject. In some arrangements, the head restraint pad 1230 is suitably shaped and flexible enough to fit within and contour to the head restraint, as further described herein. In that regard, the head restraint pad 1230 is or includes padding for providing comfort to the head of the subject. In some arrangements, the head restraint pad 1230 is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like. In some arrangements, the head restraint pad 1230 has any suitable firmness for supporting the head of the subject, such as, but not limited to, in a range of about 0.1 pound per square inch (psi) to about 60 psi (e.g., in a range of about 0.1 psi to about 10 psi) or within other suitable ranges of firmness. In some arrangements, the head restraint pad 1230 has memory for expanding to fit contours of the head of the subject. In some arrangements, the head restraint pad 1230 can be compressed and after being pressed against the head of the subject to help secure the head.

The dimensions of the head restraint pad 1230 enable the head restraint pad 1230 (as enclosed by the enclosure 1235) to fit into a space defined by a portion of the side walls of the bottom portion 1315, a side surface of the head cradle pad 1220, and the bottom surface 1320. For example, the side surface of the head cradle pad 1220 is curved inward, leaving a space between the side surface of the head cradle pad 1220 and the portion of the side walls of the bottom portion 1315, as shown. Dimensions of the space defined by the portion of the side walls of the bottom portion 1315, the side surface of the head cradle pad 1220, and the bottom surface 1320 allow the head restraint pad 1230 to fit snugly into the space. Because the head restraint pad 1230 is made of soft material, the head restraint pad 1230 (as enclosed by the enclosure 1235) is compressed as the head restraint pad 1230 is being placed in the space, and expands against one or more of the portion of the side walls of the bottom portion 1315, the side surface of the head cradle pad 1220, and the bottom surface 1320 after the head restraint pad 1230 has been placed in the space. In that regard, the head restraint pad 1230 is placed in the disposable container 121 after the head cradle pad 1220 is placed in the disposable container 1210. As such, both the head restraint pad 1230 and the head cradle pad 1220 expand against one another and the side walls of the bottom portion 1315 in the disposable container 1210, reducing movement.

Figure 16:
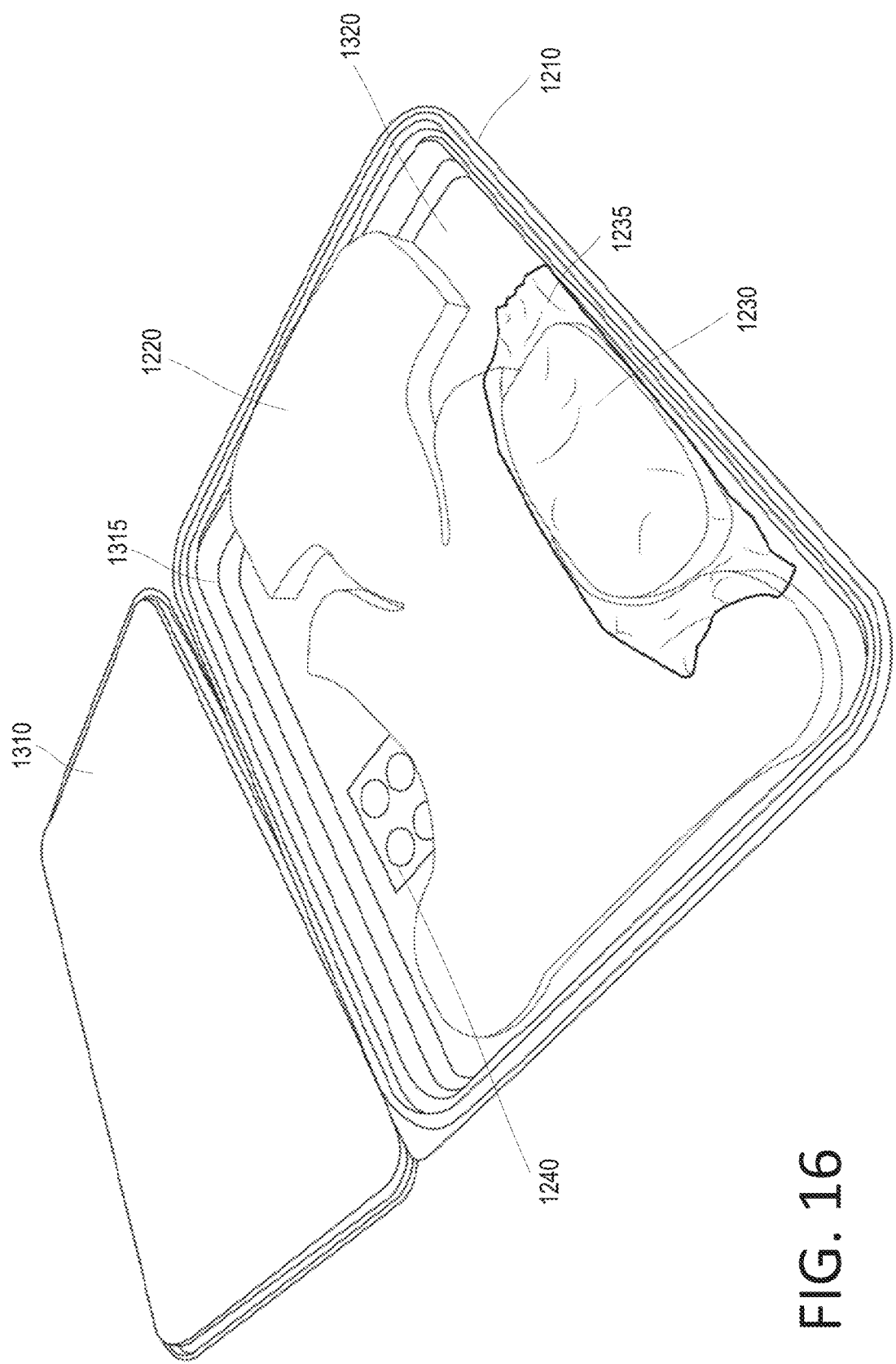
FIG. 16 shows a perspective view of the disposable container (opened) containing the head cradle pad, the head restraint pad, and a sheet including one or more fiducial markers of the disposable kit shown in FIG. 12, according to various arrangements.

FIG. 16 shows a perspective view of the disposable container 1210 (opened) containing the head cradle pad 1220, the head restraint pad 1230, and the sheet 1240 including one or more fiducial markers 1245 of the disposable kit 1200, according to various arrangements. Referring to FIGS. 12-16, the sheet 1240 including one or more fiducial markers 1245 can be placed in the disposable container 1210 before or after any of the items 1220, 1230, 1235, 1250a, 1250b, and 1255 are placed in the disposable container 1210.

In some arrangements, the disposable kit 1200 is used in conjunction with a robotic device (e.g., the robotic device 2102 of FIGS. 21C and 21D, such as but not limited to, a Transcranial Doppler (TCD) device). The robotic device may have auto-register or alignment capabilities. For example, an image processing circuit of the robotic device is configured to receive image data taken by a camera, including one or more images depicting a side of a subject's head. The images captured by the camera may include, for example, a two-dimensional array of pixel brightness values. The subject's head may have the fiducial markers 1245 disposed at anatomically significant locations such that the images include the subject's head with the fiducial markers 1245. In some embodiments, the fiducial markers 1245 are disposed at anatomically significant locations so as to signify the boundaries of the workspace of the robotic device (e.g., one or more probes moved by the robotics) during a medical procedure. The fiducial markers 1245 are configured to be detected by the image processing circuit. In one example, the fiducial markers 1245 are disposed at a corner of a subject's eye and at the tragus of the subject.

In that regard, each of the one or more fiducial markers 1245 has a first surface that includes an adhesive layer for affixing to the sheet 1240 (and to a body of a subject) and a second surface opposite to the first surface including a reflective surface for reflecting light that is captured by a camera of the robotic device. Accordingly, the fiducial markers 1245 can be affixed to a subject to define a workspace of the robotic device with respect to the subject, which can be referred to as registration of the robotic device (e.g., via optical registration using the camera of the robotic device).

Figure 17:
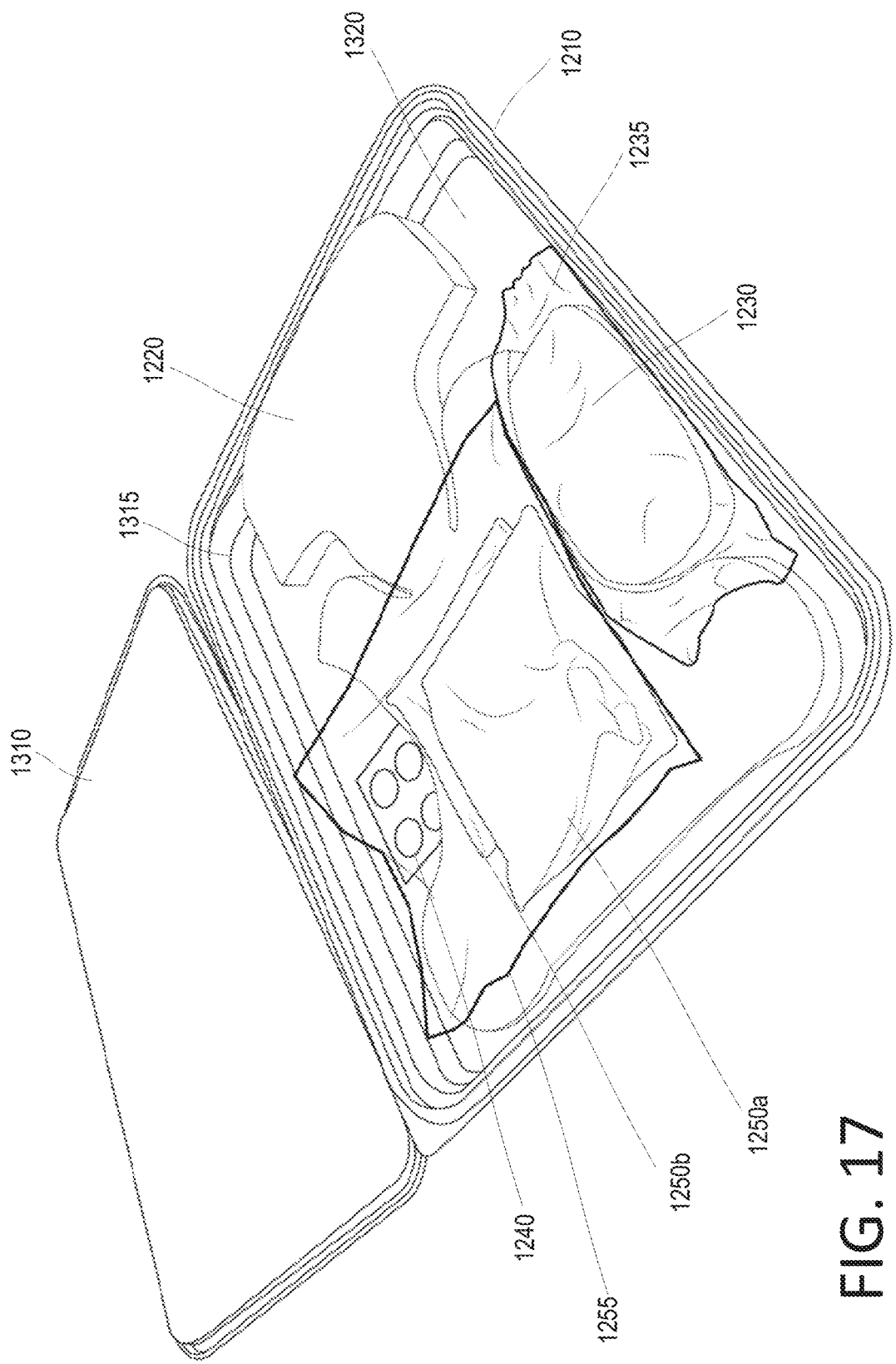
FIG. 17 shows a perspective view of the disposable container (opened) containing the head cradle pad, the head restraint pad, the sheet including one or more fiducial markers, and at least one disposable enclosure of the disposable kit shown in FIG. 12, according to various arrangements.

FIG. 17 shows a perspective view of the disposable container 1210 (opened) containing the head cradle pad 1220, the head restraint pad 1230, the sheet 1240 including one or more fiducial markers 1245, and at least one disposable enclosure (e.g., the disposable enclosures 1250a and 1250b) of the disposable kit 1200, according to various arrangements. Referring to FIGS. 12-17, the disposable enclosures 1250a and 1250b are configured to be placed over corresponding robotic pods 2106a and 2106b (e.g., to sealing and protect the robotic pods 2106a and 2106b from liquid and particle ingress). In some arrangements, the disposable enclosures 1250a and 1250b are made from a light and inexpensive material such as plastic so that the disposable enclosures 1250a and 1250b can be easily discarded after use. The disposable enclosures 1250a and 1250b are enclosed by the enclosure 1255 for additional ingress protection. The enclosure 1255 may be an enclosure such as, but not limited to, the enclosure 1235. The enclosure 1255 has a suitable size configured to enclose the disposable enclosures 1250a and 1250b in a side-by-side arrangement or in a stacked arrangement. The disposable enclosures 1250a and 1250b can be placed side-by-side or stacked in the disposable container 1210. The disposable enclosures 1250a and 1250b (as enclosed by the enclosure 1255) can be placed in the disposable container 1210 after the head cradle pad 1220 and the head restraint pad 1230 are placed in the disposable container 1210.

Figure 18:
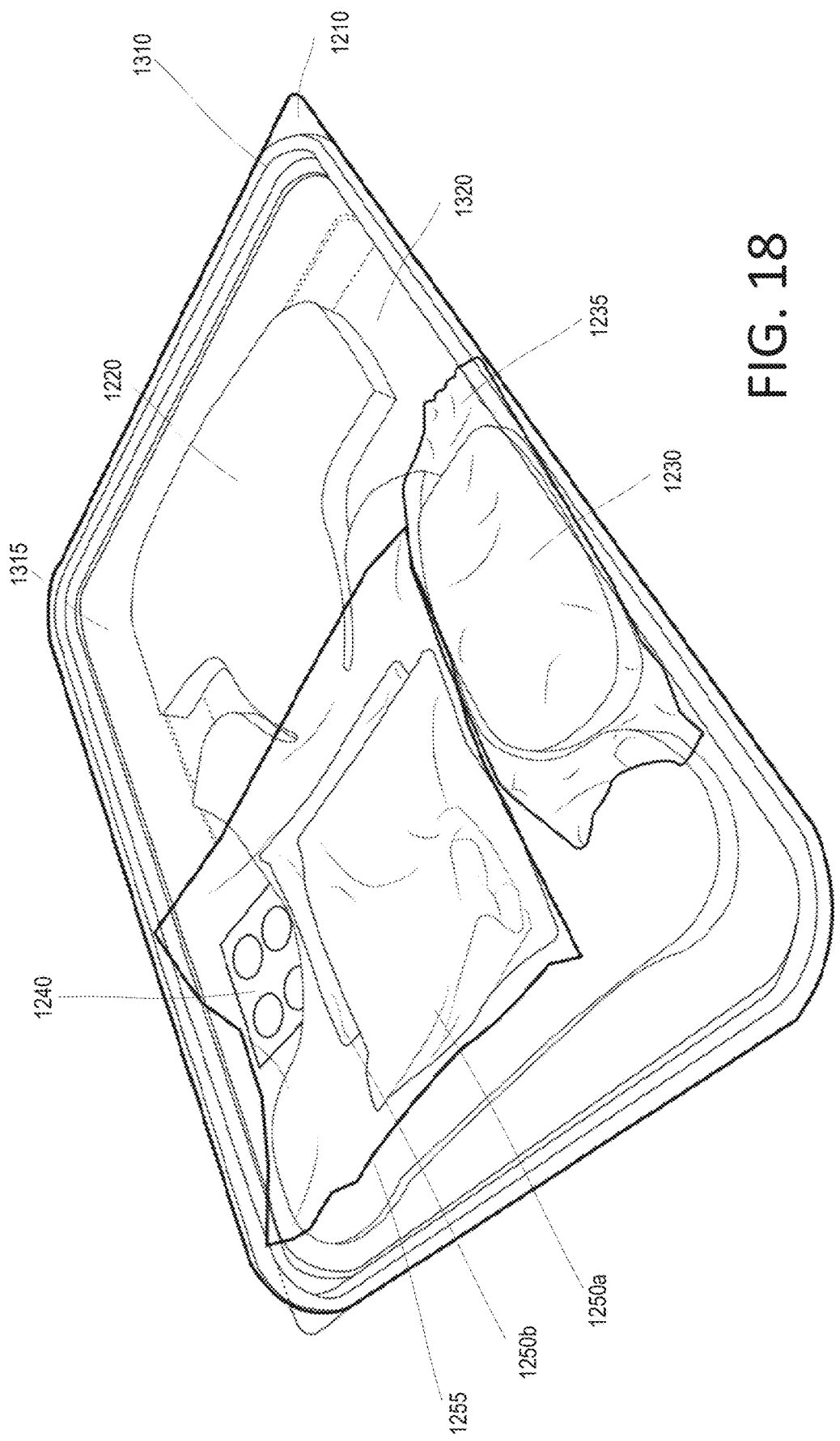
FIG. 18 shows a perspective view of the disposable container (closed) containing the head cradle pad, the head restraint pad, the sheet including one or more fiducial markers, and at least one disposable enclosure of the disposable kit shown in FIG. 12, according to various arrangements.

FIG. 18 shows a perspective view of the disposable container 1210 (closed) containing the head cradle pad 1220, the head restraint pad 1230, the sheet 1240 including the fiducial markers 1245, and at least one disposable enclosure (e.g., the disposable enclosures 1250*a* and 1250*b*) of the disposable kit 1200, according to various arrangements. Referring to FIGS. 12-17, the lid 1310 can be closed after the head cradle pad 1220, the head restraint pad 1230 (enclosed by the enclosure 1235), the sheet 1240 including one or more fiducial markers 1245, and the disposable enclosures 1250*a* and 1250*b* (enclosed by the enclosure 1255) are placed in the disposable container 1210.

Figure 19:
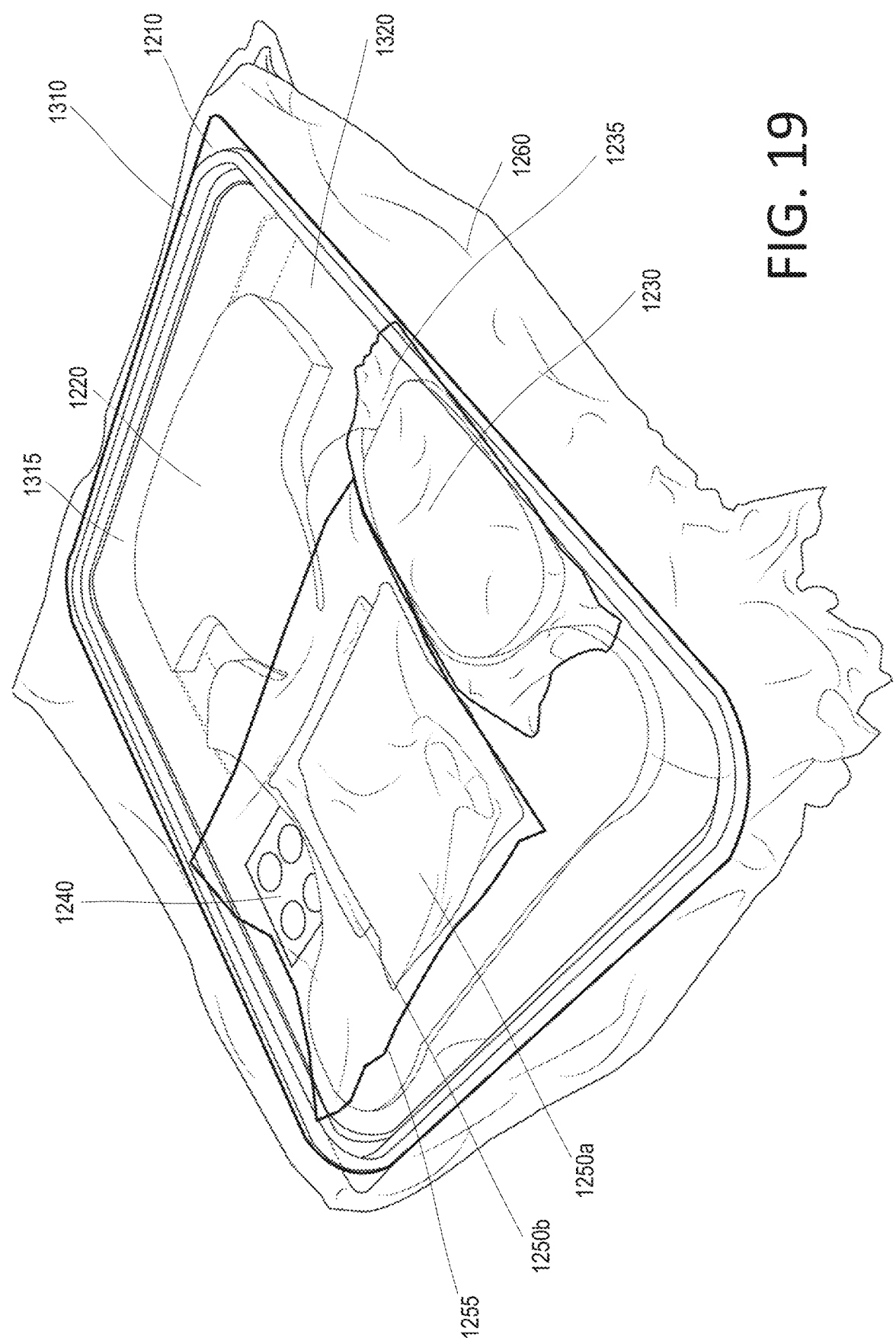
FIG. 19 shows a perspective view of a disposable packaging enclosing the disposable container (closed) containing the head cradle pad, the head restraint pad, the sheet including one or more fiducial markers, and at least one disposable enclosure of the disposable kit shown in FIG. 12, according to various arrangements.

FIG. 19 shows a perspective view of the disposable packaging 1260 enclosing the disposable container 1210 (closed) containing the head cradle pad 1220, the head restraint pad 1230, the sheet 1240 including the fiducial markers 1245, and at least one disposable enclosure (e.g., the disposable enclosures 1250*a* and 1250*b*) of the disposable kit 1200, according to various arrangements. The disposable packaging 1260 may be an enclosure such as, but not limited to, the disposable packaging 170. The enclosure 1260 has a suitable size configured to form-fit or otherwise enclose the disposable container 1210 (closed).

Accordingly, FIGS. 12-19 illustrate a sequence by which the disposable kit 1200 is assembled or otherwise provided, as described. For example, the opened disposable container 1210 is first provided. The head cradle pad 1220 is placed in the disposable container 1210. The head restraint pad 1230 (enclosed in the enclosure 1235) is placed in the disposable container 1210 after the head cradle pad 1220 is placed in the disposable container 1210. The disposable enclosures 1250*a* and 1250*b* (enclosed in the enclosure 1255) are placed in the disposable container 1210 after the head cradle pad 1220 and the head restraint pad 1230 are placed in the disposable container 1210. The sheet 1240 including the fiducial markers 1245 can be placed in the disposable container 1210 at any time. The disposable container 1210 is then closed and sealed. The disposable packaging 1260 then encloses and seals the disposable container 1210 therein. Other suitable sequences by which the disposable kit 1200 is assembled can be likewise implemented.

In some arrangements, the disposable kit 1200 provides similar benefits as those described above with respect to the disposable kit 100 (e.g., prevents or mitigates contamination of the items held therein). In addition, in some arrangements, the disposable kit 1200 can be used to contain used items that were previously housed therein for safe and easy disposal and for protection against contamination against the surrounding environment by the used items (as described above with respect to the disposable kit 100).

Figure 20A:
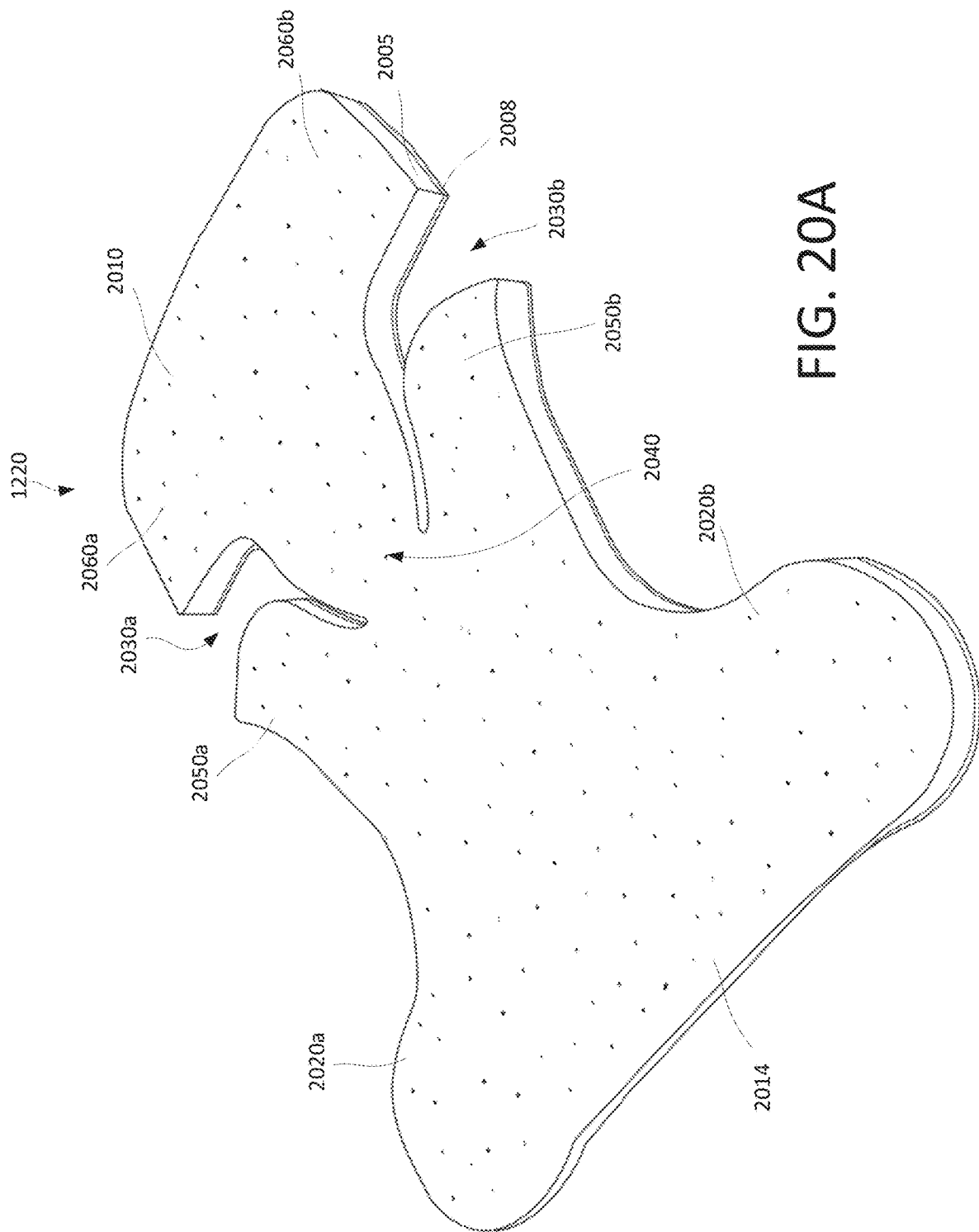
FIG. 20A shows a perspective view of the head cradle pad of the disposable kit shown in FIG. 12, according to various arrangements.
Figure 20D:
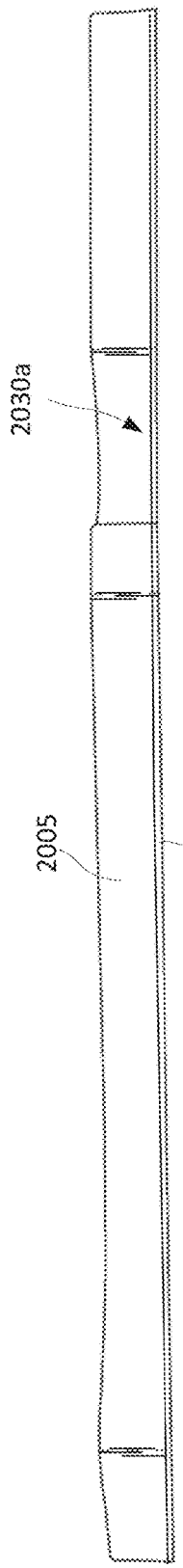
FIG. 20D shows a first side view of the head cradle pad of the disposable kit shown in FIG. 12, according to various arrangements.
Figure 20E:
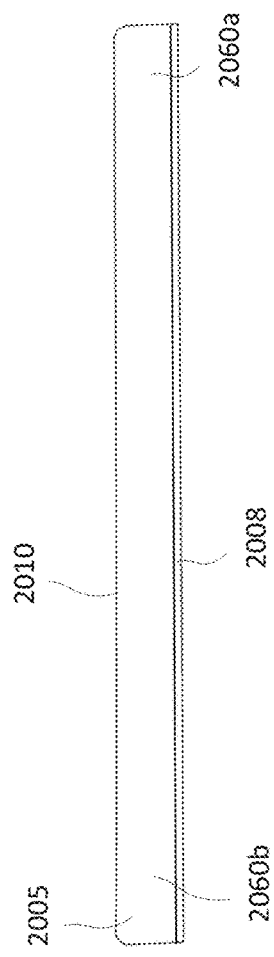
FIG. 20E shows a top view of the head cradle pad of the disposable kit shown in FIG. 12, according to various arrangements.
Figure 20F:
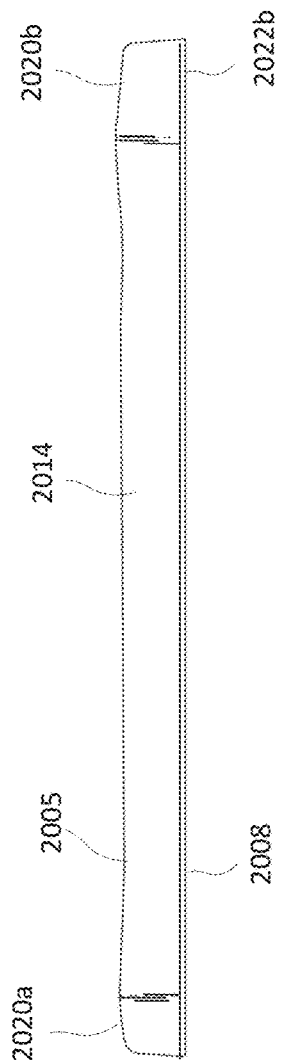
FIG. 20F shows a bottom view of the head cradle pad of the disposable kit shown in FIG. 12, according to various arrangements.
Figure 21A:
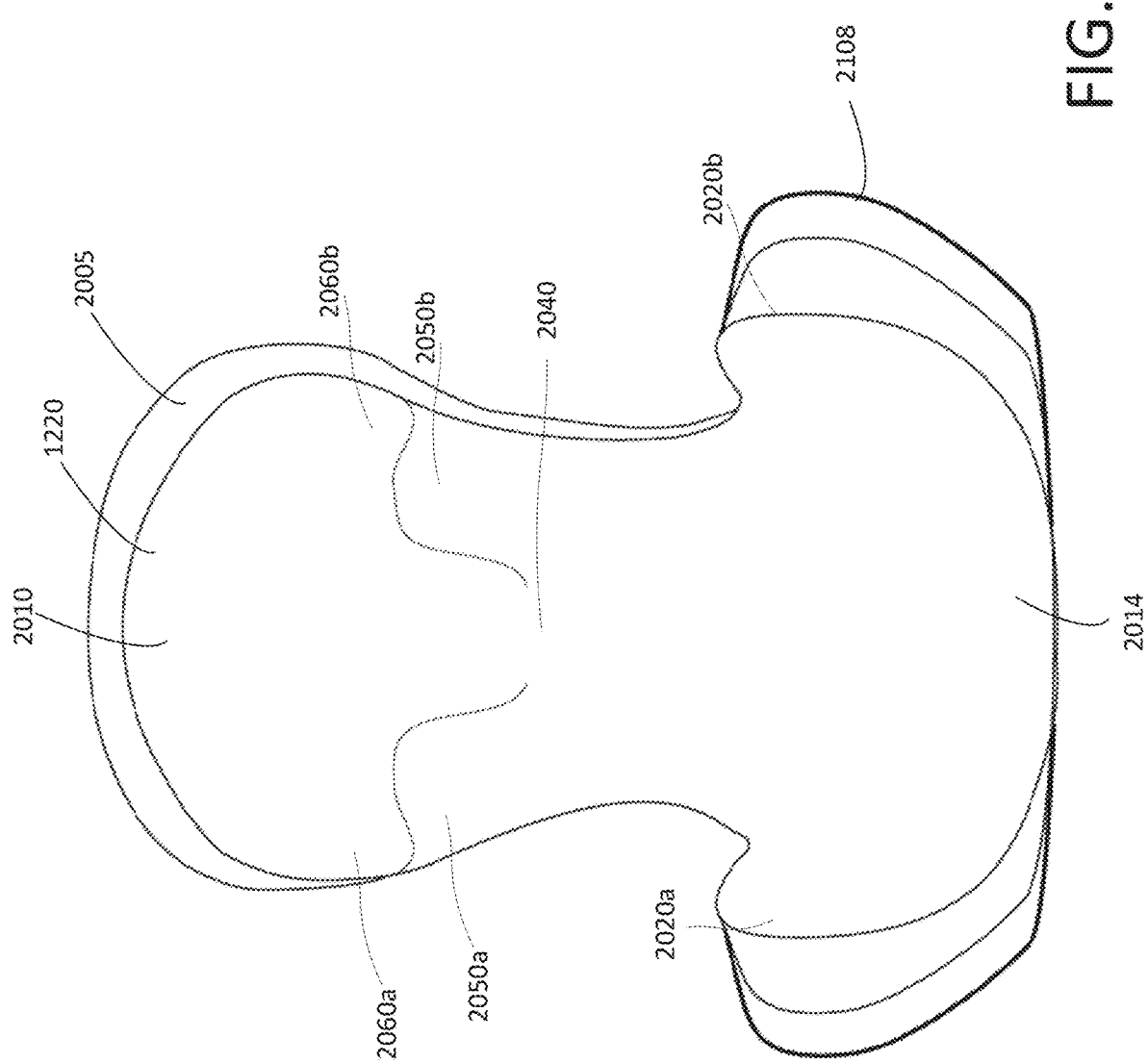
FIG. 21A shows the head cradle pad of the disposable kit shown in FIG. 12 deployed in a head cradle of a robotic device, according to various arrangements.
Figure 21B:
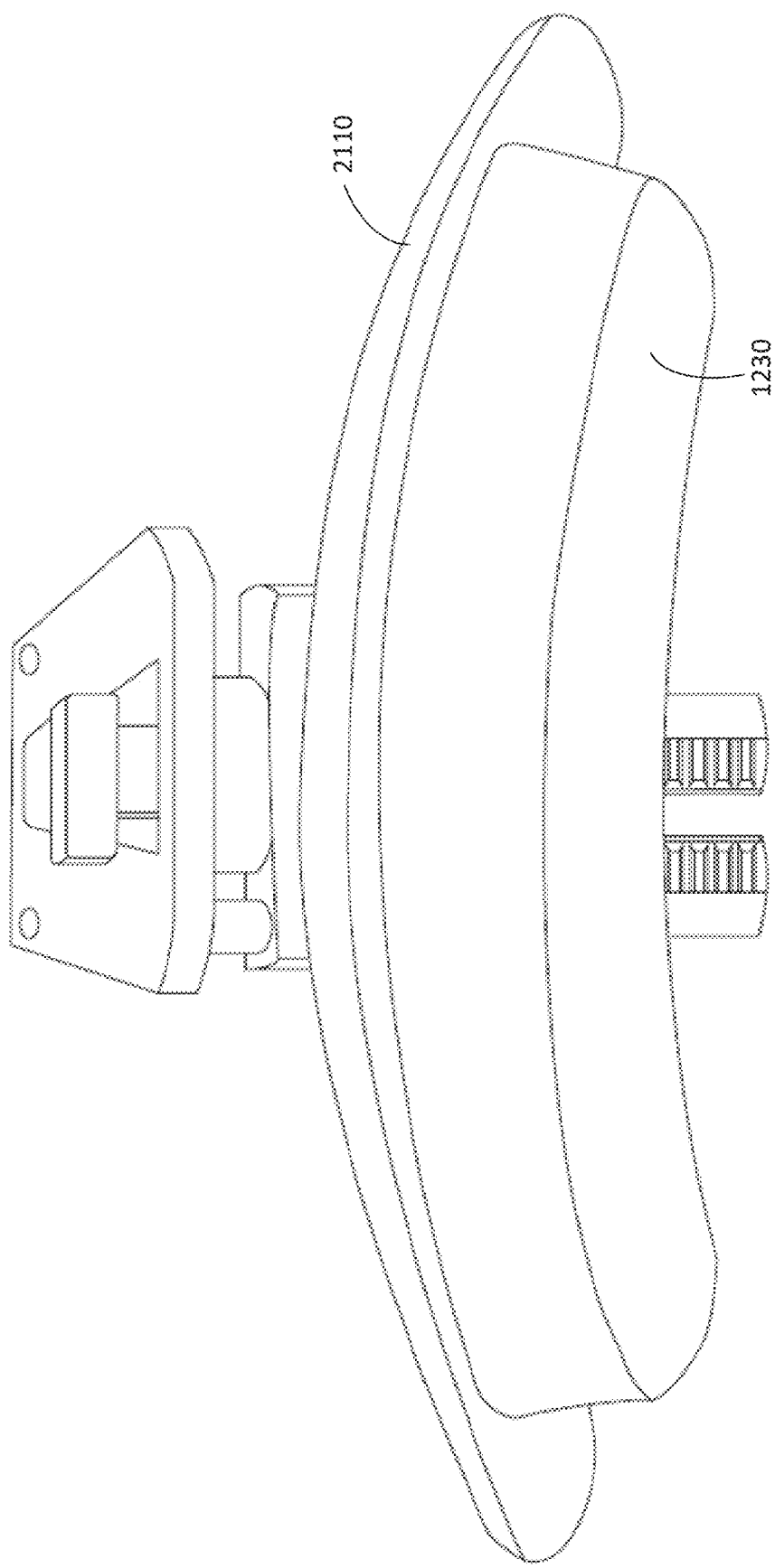
FIG. 21B shows the head restraint pad of the disposable kit shown in FIG. 12 deployed in a head restraint of a robotic device, according to various arrangements.

FIG. 20A shows a perspective view of the head cradle pad 1220 (in a default, flat, resting state), according to various arrangements. FIG. 20B shows a front view of the head cradle pad 1220 (in a default, flat, resting state), according to various arrangements. FIG. 20C shows a back view of the head cradle pad 1220 (in a default, flat, resting state), according to various arrangements. FIG. 20D shows a first side view of the head cradle pad 1220 (in a default, flat, resting state), according to various arrangements. FIG. 20E shows a top view of the head cradle pad 1220 (in a default, flat, resting state), according to various arrangements. FIG. 20F shows a bottom view of the head cradle pad 1220 (in a default, flat, resting state), according to various arrangements. FIG. 21A shows the head cradle pad 1220 deployed in the head cradle 2108 of the robotic device 2102, according to various arrangements. FIG. 21B shows the head restraint pad 1230 deployed in the head restraint 2110 of the robotic device 2102, according to various arrangements. FIGS. 21C-21E illustrate a method of using the disposable kit 1200, according to various arrangements.

Referring to FIGS. 12-21E, in some arrangements, the robotic device 2102 includes at least one robotic pod (e.g., the robotic pods 2106*a* and 2106*b*), the head cradle 2108, and a head restraint 2110. Each of the robotic pods 2106*a* and 2106*b* defines a cavity that faces the head cradle 2108. A probe (e.g., a transducer) extends from the cavity towards the head cradle 2108. Each of the robotic pods 2106*a* and 2106*b* includes robotics connected to the probe that enables automatic movement of the probe with respect to a subject. The head cradle 2108 is shaped and configured to receive and retain a head 2120 of a subject and/or portion of a neck 2124 of the subject when the head cradle pad 1220 is set on the head cradle 2108. The head restraint 2110 is shaped and configured to contact and apply pressure against a front of the head 2120 (e.g., forehead), for example, after placing the head restraint pad 1230 on the head restraint 2110. The head cradle pad 1220 is symmetrical about a center symmetry line.

The head cradle pad 1220 can be affixed to the head cradle 2108 according to various arrangements. An entirety of the head cradle pad 1220 conforms and corresponds to the entire shape of the head cradle 2108 strictly or almost strictly. For example, a bottom of the head cradle pad 1220 corresponds to the shape of the bottom of the head cradle 2108. The bottom of the head cradle 2108 refers to a portion of the head cradle 2108 that is farthest from the head restraint 2110. The bottom of the head cradle pad 1220 includes wings 2020*a* and 2020*b* extending from each side of the body of the head cradle pad 1220 to align with extended portions of the head cradle 2108. The wings 2020*a* and 2020*b* extend substantially perpendicularly in two opposing, outward directions from a center symmetry line about which the head cradle pad 1220 is symmetric. A substantially straight bottom edge of the second section 2014 extends continuously into a rounded end of each of the wings 2020*a* and 2020*b*. The rounded end for each of the wings 2020*a* and 2020*b* is formed by a rounded edge that gives the wing 2020*a* or 2020*b* its wing-like appearance, as the rounded end extends from the center symmetry line. The rounded edges of the wings 2020*a* and 2020*b* continues to extend toward the flanges 2050*a* and 2050*b*, extending inwardly toward the center symmetry line such that there is a gap of empty space (e.g., elliptical empty space) between the wings 2020*a* and 2020*b* and the respective flanges 2050*a* and 2050*b*. Accordingly, the bottom of the head cradle pad 1220 can receive, contact, and cushion a neck of the subject (or an upper portion of the neck) around a circumferential surface of the neck. The wings 2020*a* and 2020*b* allow the head cradle pad 1220 to cover additional circumferential surfaces of the neck. Furthermore, because the wings 2020*a* and 2020*b* of the head cradle pad 1220 extend widely from the body of the head cradle pad 1220, the head cradle pad 1220 can accommodate various shapes and sizes of necks and heads of subjects.

In some arrangements, the head cradle pad 1220 has a top or first section 2010 and a bottom or second section 2014. The second section 2014 is larger (e.g., by area) than the first section 2010. The first section 2010 and the second section 2014 are separated by and connected by a center connection portion 2040. In some arrangements, the head cradle pad 1220 is pressed and affixed, for example, via the adhesive at the back surface of the head cradle pad 1220 (e.g., the back surface of the pad layer 2005) into the recessed head cradle 2108. The first section 2010 and the second section 2014 of the head cradle pad 1220 are bunched together to fit within the recessed or concave shape of the head cradle 2108, sufficiently occupying most or all of the surface area of the head cradle 2108. For example, when the head cradle pad 1220 is affixed to the head cradle 2108, the first section 2010 and the second section 2014 contract or otherwise bend towards each other at the center connection portion 2040. Lateral sides or edges of the head cradle pad 1220 (on the first section 2010 and the second section 2014) also contract or otherwise bend towards each other at the center connection portion 2040. For example, the wings 2020a and 2020b bend towards each other about a center symmetry line of the head cradle pad 1220. The center symmetry line extends from the first section 2010 to the second section 2014, such that the head cradle pad 1220 is symmetric about the center symmetry line. The center symmetry line divides a portion of the first section 2010 into tabs 2060a and 2060b, which are symmetric about the center symmetry line. The center symmetry line divides a portion of the second section 2014 into wings 2020a and 2020b, which are symmetric about the center symmetry line. As another example, when the head cradle pad 1220 is affixed to the head cradle 2108, the areas surrounding and extending from the center connection portion 2040 bend towards each other, in directions towards the center connection portion 2040. Furthermore, the center connection portion 2040 bends inwards and towards itself to conform to the recessed contour of the head cradle 2108. The center connection portion 2040 (and the portion surrounding the center connection portion 2040) at the pad layer 2005 bends inwards toward itself, away from the adhesive layer 2008. When the adhesive layer 2008 is removed and the pad layer 2005 is being deployed to the head cradle 2108, an adhesive side of the pad layer 2005 is configured to face the head cradle 2108 while a pad side of the pad layer 2005 is configured to face and bend inward toward the center connection portion 2040. For example, a pad side of the first section 2010 and a pad side of the second section 2014 face and bend toward each other at the center connection portion 2040. Similarly, a pad side of the flange 2050a and a pad side of the flange 2050b face and bend toward each other at the center connection portion 2040.

In some arrangements, the head cradle pad 1220 has flanges 2050a and 2050b extending from the second section 2014 and from each side of the center connection portion 2040. The flanges 2050a and 2050b extend substantially diagonally in two, outward directions from the center symmetry line and the center connection portion 2040. A substantially rounded edge of each of the flanges 2050a and 2050b extends continuously from the center connection portion 2040 in a curved fashion toward a pointed edge on each of the flanges 2050a and 2050b. The pointed edge on each of the flanges 2050a and 2050b extends toward the second section 2014 in a curved fashion. In particular, an edge between the pointed edge of the flange 2050a and the rounded end the wing 2020a is curved inwards toward the center connection portion 2040. Similarly, an edge between the pointed edge of the flange 2050b and the rounded end the wing 2020b is curved inwards toward the center connection portion 2040.

Furthermore, the head cradle pad 1220 has tabs 2060a and 2060b extending outward from each side of the first section 2010 of the head cradle pad 1220 and from each side of the center connection portion 2040. The tabs 2060a and 2060b extend laterally and perpendicular in two opposite, outward directions from the center symmetry line. A curved top edge of the first section 2010 extends continuously into a rounded corner of each of the tabs 2060a and 2060b. The rounded corner for each of the tabs 2060a and 2060b extends toward a respective one of the flanges 2050a and 2050b and forms a pointed corner. The pointed corner of each of the tabs 2060a and 2060b and the pointed edge on a respective one of the flanges 2050a and 2050b form an opening of a respective one of spatial gaps 2030a and 2030b.

In some arrangements, when the head cradle pad 1220 (the pad layer 2005 and the adhesive layer 2008) is in its default, flat, resting state and un-affixed to the head cradle 2108, the flanges 2050a and 2050b extend towards the tabs 2060a and 2060b such that spatial gaps 2030a and 2030b of empty space are defined between one of the flange 2050a and 2050b and a respective, corresponding one of the tabs 2060a and 2060b. An opening of each of the spatial gaps 2030a and 2030b is defined by a pointed corner of a respective one of the tabs 2060a and 2060b and a pointed edge on a respective one of the flanges 2050a and 2050b. The sizes of the spatial gaps 2030a and 2030b correspond to the distances between the tabs 2060a and 2060b and the flanges 2050a and 2050b. The sizes of the spatial gaps 2030a and 2030b decrease from the openings of the spatial gaps 2030a and 2030b toward the center connection point 2040, until the spatial gaps 2030a and 2030b ends at the center connection point 2040.

In some arrangements, when the head cradle pad 1220 (e.g., the pad layer 2005) is affixed to the head cradle 2108, the contour and the concave shape of the head cradle 2108 define the shape of the head cradle pad 1220, causing the flange 2050a and the tab 2060a to bend or otherwise move towards each other to fill in the spatial gap 2030a therebetween such that the spatial gap 2030a is substantially eliminated and occupied by the head cradle pad 1220 (e.g., the pad layer 2005). Similarly, when the head cradle pad 1220 (e.g., the pad layer 2005) is affixed to the head cradle 2108, the contour and the concave shape of the head cradle 2108 defines the shape of the head cradle pad 1220, causing the flange 2050b and the tab 2060b to bend or otherwise move towards each other to fill in the spatial gap 2030b therebetween such that the spatial gap 2030b is substantially eliminated and occupied by the head cradle pad 1220 (e.g., the pad layer 2005). In some arrangements, when the head cradle pad 1220 (e.g., the pad layer 2005) is affixed to the head cradle 2108, the flange 2050a and the tab 2060a contact each other, forming a friction seal where the spatial gap 2030a was, so that particles (e.g., body hair) and liquid (e.g., bodily fluid, gel, and the like) do not fall to the head cradle. In some arrangements, when the head cradle pad 1220 (e.g., the pad layer 2005) is affixed to the head cradle 2108, the flange 2050b and the tab 2060b contact each other, forming a friction seal where the spatial gap 2030b was, so that particles (e.g., body hair) and liquid (e.g., bodily fluid, gel, and the like) do not fall to the head cradle.

In some arrangements, adhesive is provided on one or both of a side surface of the flange 2050a and a side surface of the tab 2060a that define the spatial gap 2030a when the head cradle pad 1220 is in a flat and resting state. The side surface of the flange 2050a and the side surface of the tab 2060a face one another and define a boundary of the spatial gap 2030a. The side surfaces of the flange 2050a and the tab 2060a are perpendicular or substantially perpendicular to a flat surface of the pad layer 2005 and a flat surface of the adhesive layer 2008. When the surface of the flange 2050a and the surface of the tab 2060a contact one another, the adhesive enables the surfaces affix to each other, improving the seal. Similarly, in some arrangements, adhesive is provided on one or both of a surface of the flange 2050b and a surface of the tab 2060b that define the spatial gap 2030b when the head cradle pad 1220 is in a flat and resting state. The side surface of the flange 2050a and the side surface of the tab 2060a face one another and define a boundary of the spatial gap 2030a. The side surfaces of the flange 2050a and the tab 2060a are perpendicular or substantially perpendicular to a flat surface of the pad layer 2005 and a flat surface of the adhesive layer 2008. When the surface of the flange 2050b and the surface of the tab 2060b contact one another, the adhesive enables the surfaces to affix to each other, thereby improving the seal.

Accordingly, the design and outline shape of the head cradle pad 1220 enable a single piece of material to be inserted and affixed into the head cradle 2108 such that the head cradle pad 1220 substantially occupies all surface area of the head cradle 2108, which protects the head cradle 2108 from contacting any portion of a subject. Furthermore, because the head cradle pad 1220 is a single piece of material, as opposed to a plurality of pieces, mass manufacturing of the head cradle pad 1220 is easier and more cost-effective. For example, multiple head cradle pads 1220 can simply be outlined and cut out and removed from a long single sheet of padding. Furthermore, even though the head cradle pad 1220 is a single piece of material, the design and function thereof (as described above) allows for substantially complete and impenetrable coverage of the head cradle 2108.

The head restraint pad 1230 is affixed to the head restraint 2110 according to various arrangements. In some arrangements, the head restraint pad 1230 is shaped and sized to substantially conform to the shape and size of the head restraint 2110. In some arrangements, the head restraint pad 1230 substantially occupies most or the entire surface of the head restraint 2110 when the head restraint pad 1230 is affixed to the head restraint 2110. The head restraint pad 1230 can be affixed to the head restraint 2110 by peeling off an adhesive layer at the back surface of a pad layer of the head restraint pad 1230 to expose adhesive at the back surface of the pad layer 2005 and pressing the head restraint pad 1230 onto the surface of the head restraint 2110. Furthermore, because the head restraint 2110 has a concave shape, the head restraint pad 1230 is designed to flex inwards at a substantially center location to conform to the contours of the head restraint 2110. Accordingly, the head restraint pad 1230 defines a concave shape when affixed to the inner surface of the head restraint 2110 such that the head restraint pad 1230 can conform, contact, and apply suitable pressure to a front of a subject's head (e.g., a forehead of the subject).

As shown, the disposable enclosure 1250a can enclose or otherwise cover the robotic pod 2106a according to various arrangements. In some arrangements, the disposable enclosure 1250a defines a first hole (e.g., the first hole 22120 of FIGS. 22B, 22C, 22E, 22G, and 22H) through which the probe (extending from the cavity of the robotic pod 2106a) extends. The first hole and the probe can form a seal between the probe and the disposable enclosure 1250a that prevents liquids and particles from penetrating through the disposable enclosure 1250a and into the robotic pod 2106a. As such, in some arrangements, the disposable enclosure 1250a adequately covers the cavity defined by the robotic pod 2106a such that liquid or particles are prevented from entering into the robotic pod 2106a (e.g., via the cavity) so that the components and mechanisms of the robotic pod 2106a are protected during use. In some arrangements, the disposable enclosure 1250a further defines one or more apertures at the top corners thereof to allow a camera extending from the top of the robotic pod 2106a to extend through the disposable enclosure 1250a.

With respect to a method of using the disposable kit 1200 according to various arrangements, the head cradle pad 1220 is affixed to the head cradle 2108. For example, the adhesive layer 2008 is pealed from the pad layer 2005, to expose the adhesive on the back surface of the pad layer 2005. The shape of the head cradle pad 1220 (e.g., the shape of the pad layer 2005) can be manipulated to conform or otherwise fit the shape and contour of the head cradle 2108. The head cradle pad 1220 (e.g., the pad layer 2005) is affixed to the head cradle 2108 via the adhesive, for example, by pressing the pad layer 2005 with the adhesive onto the head cradle 2108 such that the adhesive contacts and adheres to the concave surface of the head cradle 2108. The head restraint pad 1230 is affixed to the head restraint 2110. The head restraint pad 1230 can be affixed to the head restraint 2110 by peeling off the adhesive layer at the back surface of the pad layer of the head restraint pad 1230 to expose the adhesive at the back surface of the pad layer 2005 and pressing the head restraint pad 1230 with the adhesive onto the head restraint 2110 such that the adhesive contacts and adheres to the concave surface of the head restraint 2110. Affixing the head cradle pad 1220 and affixing the head restraint pad 1230 as shown in FIG. 21C can be performed in any suitable order or simultaneously. As shown in FIG. 21D, the disposable enclosure 1250a is placed over the robotic pod 2106a to enclose the robotic pod 2106a to provide ingress protection. The disposable enclosure 1250b can be likewise placed over the robotic pod 2106b to enclose the robotic pod 2106b to provide ingress protection. The probe of each of the robotic pods 2106a and 2106b is positioned through a corresponding, respective hole (e.g., the first hole 22120 of) the disposable enclosure 1250a or 1250b. The camera of each of the robotic pods 2106a and 2106b is positioned through a corresponding, respective top corner aperture (e.g., a second hole 22130 of FIGS. 22B-22D and 22G) of the disposable enclosure 1250a or 1250b. Next, the fiducial markers 1245 are applied to the subject (e.g., two fiducial markers 1245 are affixed at each side of the subject's head 2120). For each side of the subject's head 2120, one of the fiducial markers 1245 can be disposed at a corner of a subject's eye, and one of the fiducial markers 1245 can be disposed at the tragus of the subject, as shown in FIG. 21E. Gel can be applied on a gel zone 2122 by a healthcare provider or by an automatic gel applicator on each of the robotic pods 2106a and 2106, as shown in FIG. 21E.

Figure 22A:
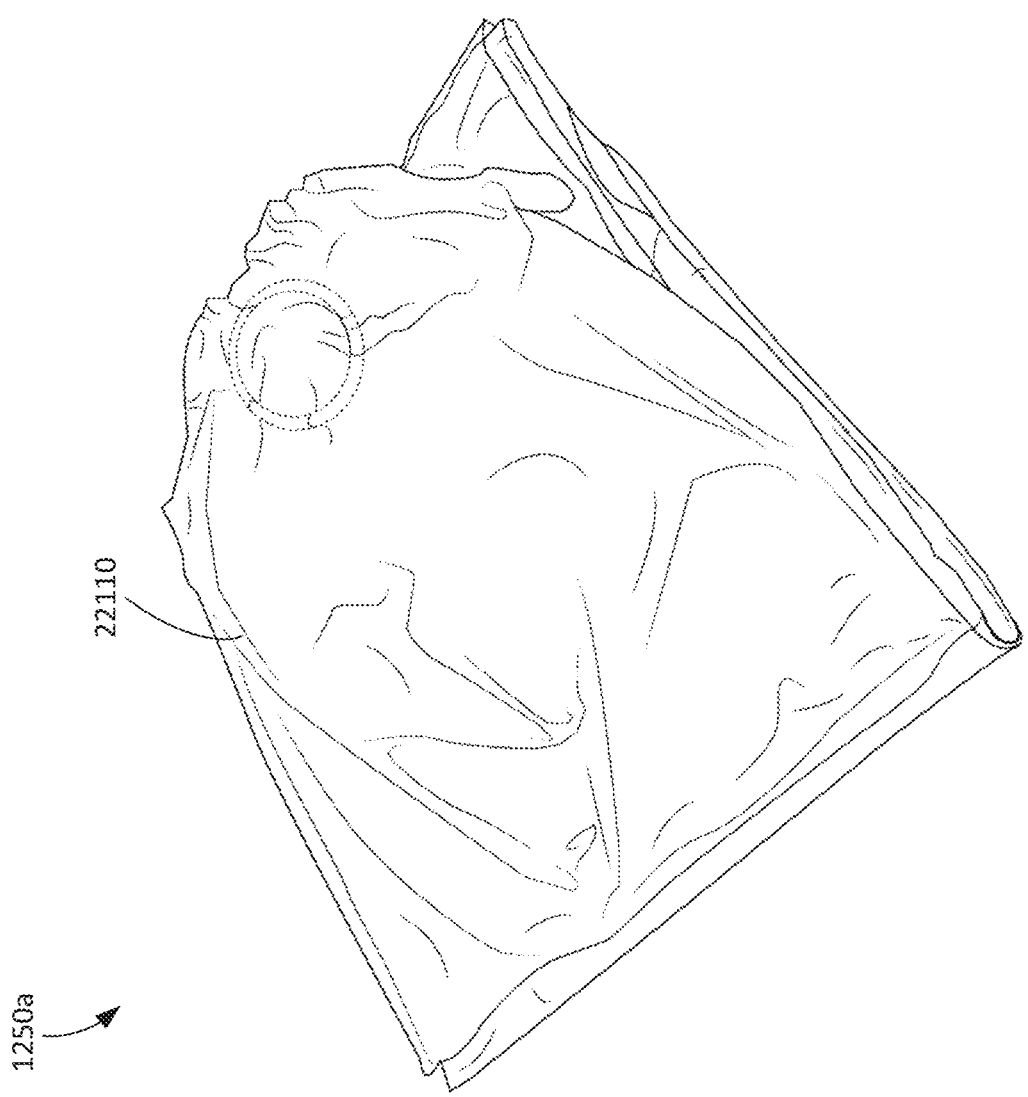
FIG. 22A shows a perspective view of the disposable enclosure (folded) of the disposable kit shown in FIG. 12, according to various arrangements.
Figure 22B:
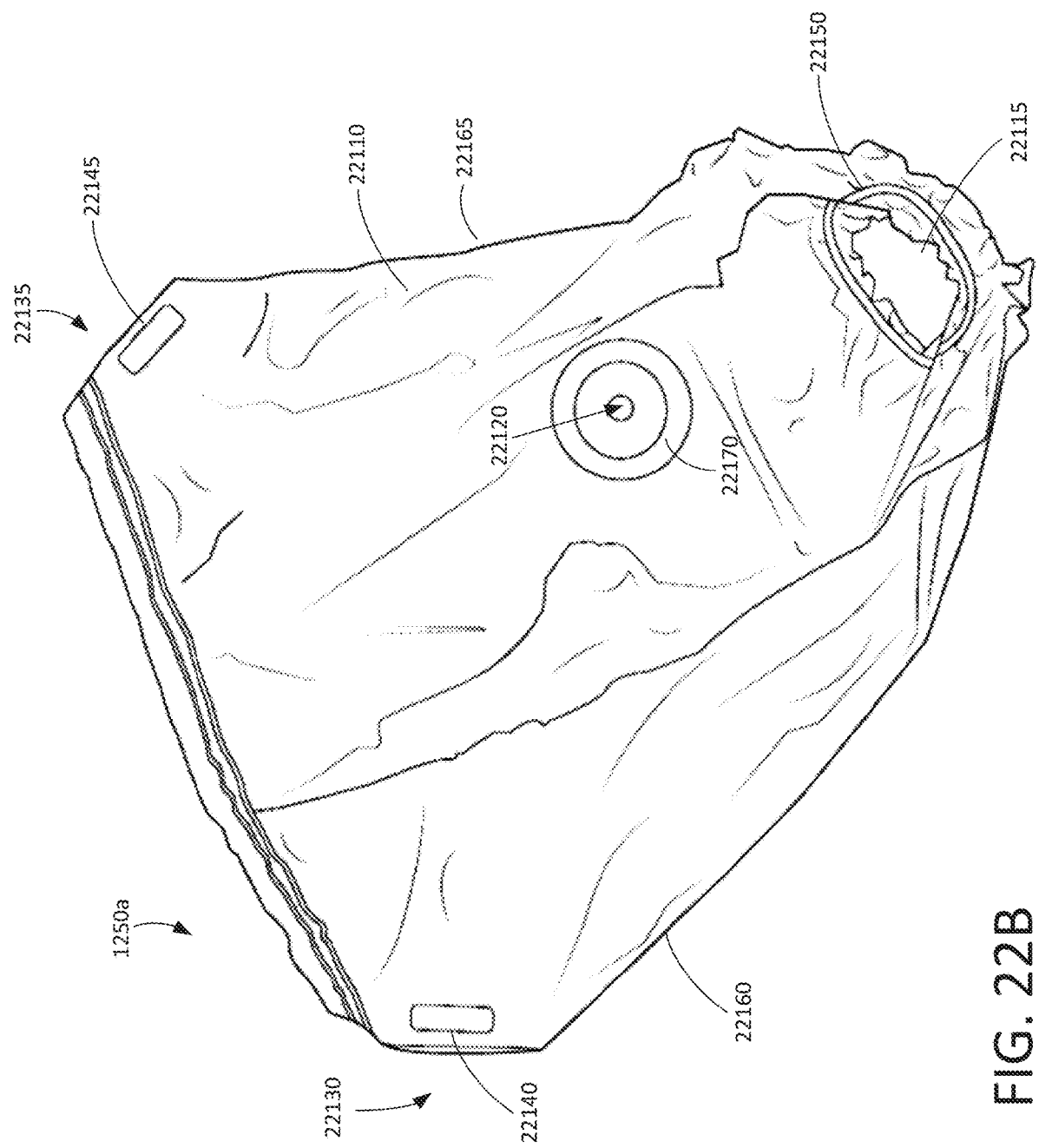
FIG. 22B shows a perspective view of the disposable enclosure (unfolded) of the disposable kit shown in FIG. 12, according to various arrangements.
Figure 22C:
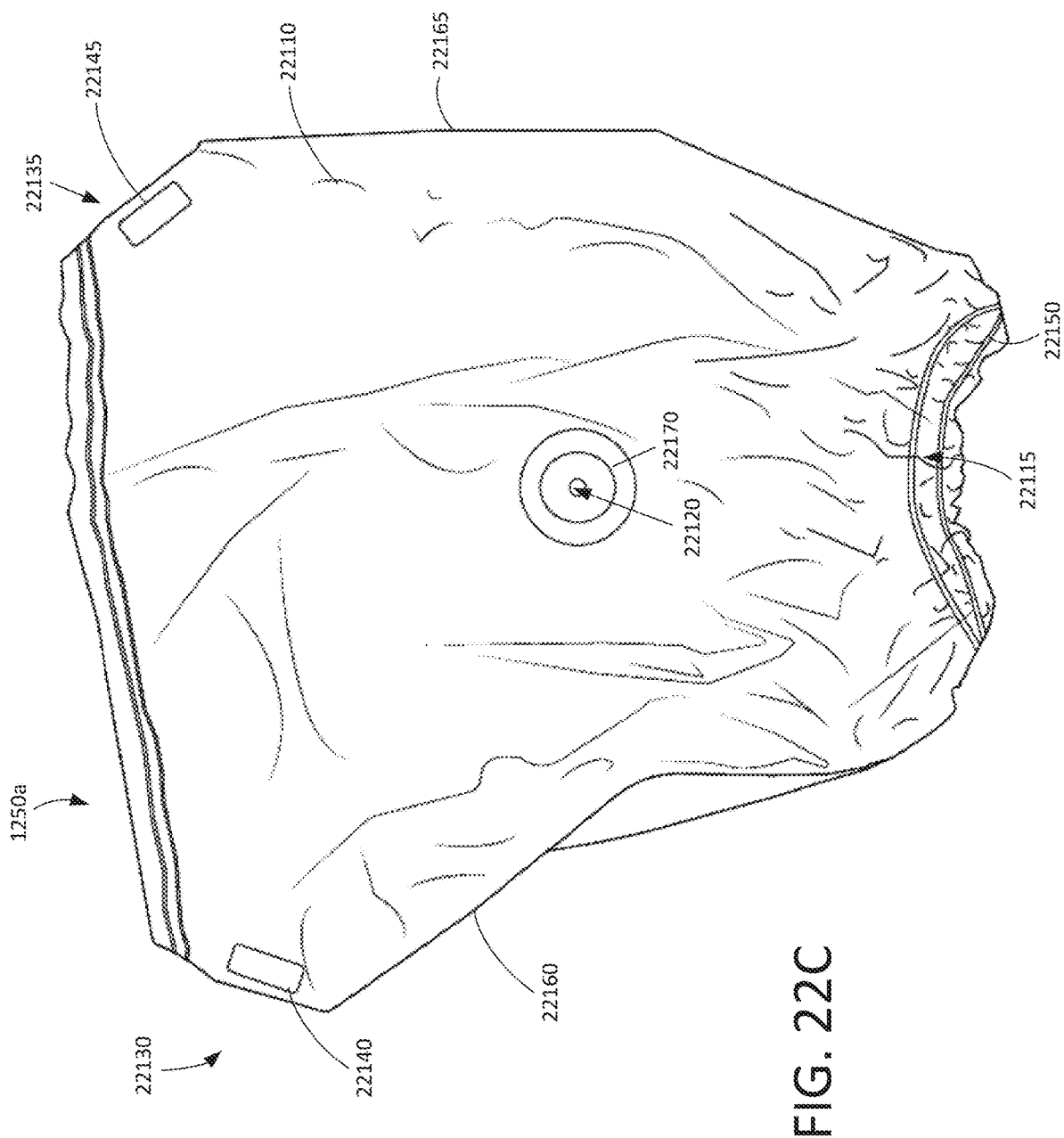
FIG. 22C shows a front view of the disposable enclosure (unfolded) of the disposable kit shown in FIG. 12, according to various arrangements.
Figure 22D:
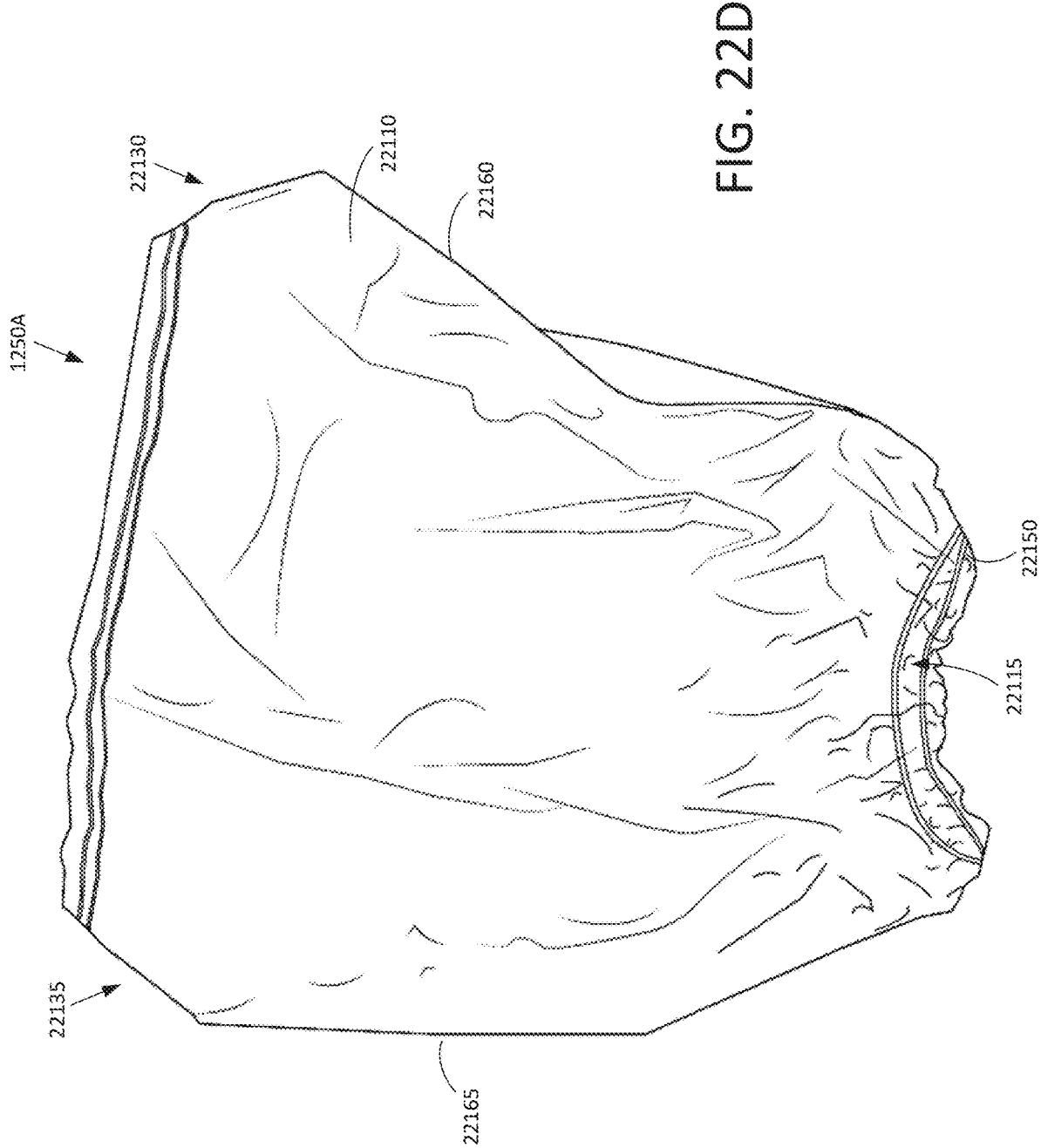
FIG. 22D shows a back view of the disposable enclosure (unfolded) of the disposable kit shown in FIG. 12, according to various arrangements.
Figure 22E:
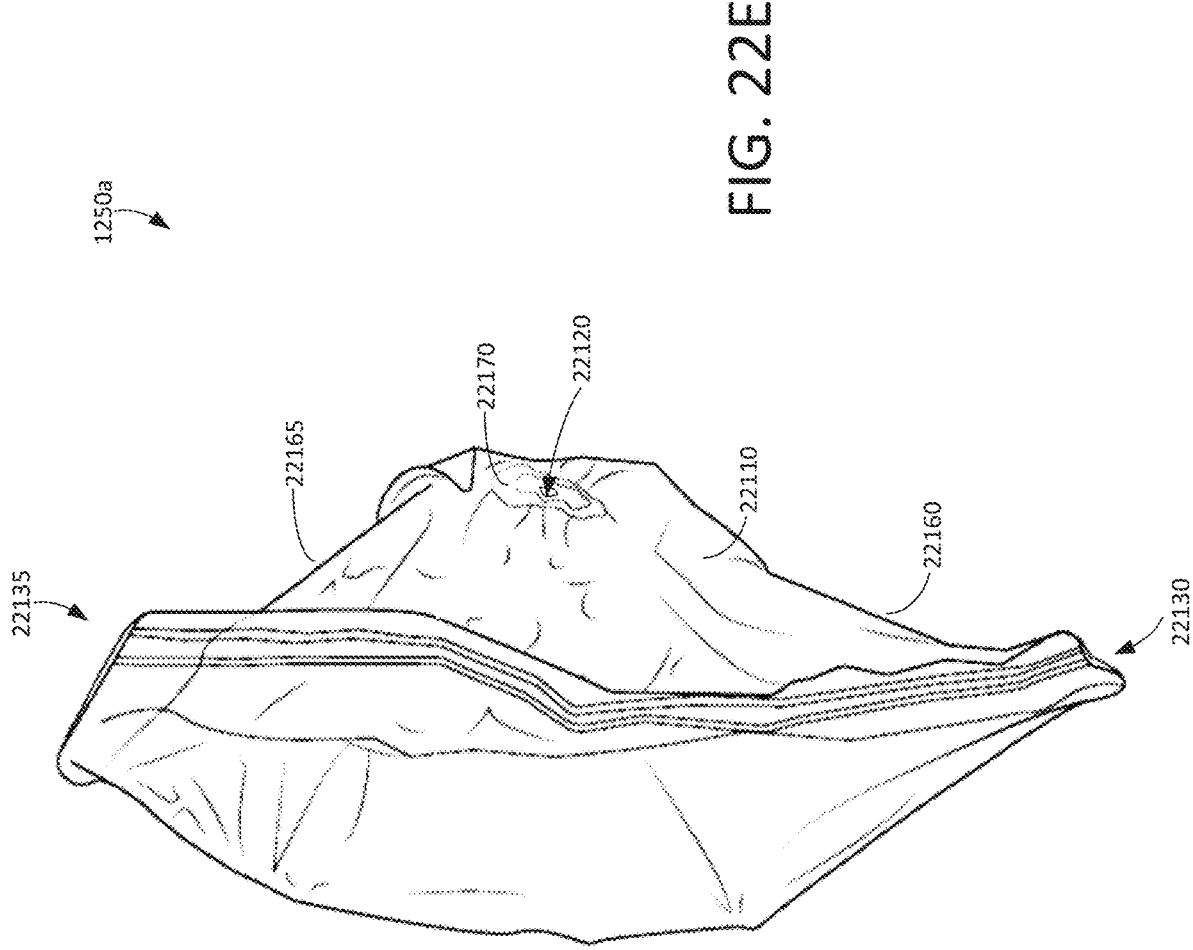
FIG. 22E shows a top view of the disposable enclosure (unfolded) of the disposable kit shown in FIG. 12, according to various arrangements.
Figure 22F:
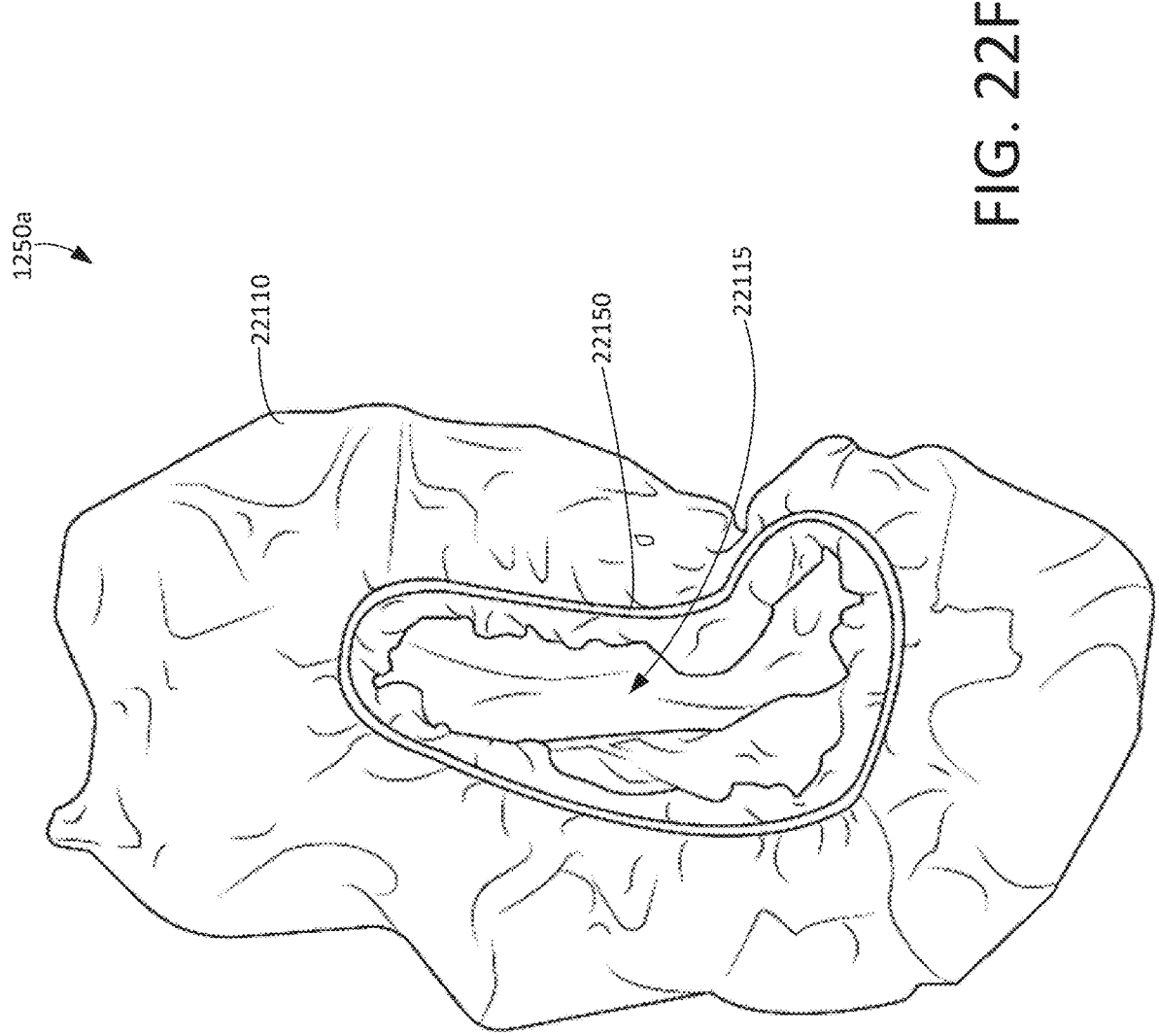
FIG. 22F shows a bottom view of the disposable enclosure (unfolded) of the disposable kit shown in FIG. 12, according to various arrangements.

FIG. 22A shows a perspective view of the disposable enclosure 1250a (folded), according to various arrangements. FIG. 22B shows a perspective view of the disposable enclosure 1250a (unfolded), according to various arrangements. FIG. 22C shows a front view of the disposable enclosure 1250a (unfolded), according to various arrangements. FIG. 22D shows a back view of the disposable enclosure 1250a (unfolded), according to various arrangements. FIG. 22E shows a top view of the disposable enclosure 1250a (unfolded), according to various arrangements. FIG. 22F shows a bottom view of the disposable enclosure 1250a (unfolded), according to various arrangements. FIG. 22G shows a first side view of the disposable enclosure 1250a (unfolded), according to various arrangements. FIG. 22H shows a second side view of the disposable enclosure 1250a (unfolded), according to various arrangements. Referring to FIGS. 12-22H, the disposable enclosures 1250a and 1250b may be identical, thus description pertaining to the disposable enclosure 1250a likewise pertains to the disposable enclosure 1250b. Examples of the disposable enclosures 1250a and 1250b include those disclosed in U.S. patent application Ser. No. 15/952,791, titled Enclosure For Device Including Probe, filed on Apr. 13, 2018, which is hereby incorporated by reference in its entirety.

Each of the two robotic pods 2106a and 2106b of the robotic device 2102 may include a probe movable by suitable robotics and a cavity within which probe can move. In that regard, the size, position, and shape of the cavity define a workspace of the probe. The cavity may expose components of the robotic pods 2106a and 2106b other than the probe. The disposable enclosure 1250a may be configured to prevent liquid and particles from entering into the cavity.

In some arrangements, the disposable enclosure 1250a includes a removable enclosure body 22110. The enclosure body 22110 is configured to cover an entirety of the cavity when the disposable enclosure 1250a is attached, fastened, or otherwise coupled to the housing of the robotic pod 2106a. The enclosure body 22110 is configured to enclose at least a portion of the housing. In that regard, the enclosure body 22110 is made of a material that provides ingress protection against liquid (e.g., blood, sweat, and water) and particles (e.g., dust and hair) to the cavity. In some arrangements, the enclosure body 22110 is made of an elastic material that can be form-fitted to at least a portion of the housing when the disposable enclosure 1250a is attached to the housing. Furthermore, in some arrangements, the enclosure body 22110 is made of a biocompatible material suitable for contacting a human body (e.g., the head of the subject).

Therefore, in considering ingress protection, elasticity, biocompatibility, and weight, the enclosure body 22110 can be made from a material such as but not limited to, polyethylene, polypropylene, polycarbonate, polyurethane, polyetherimide, polyvinyl chloride, and polyether ether ketone in some examples. In other examples, the enclosure body 22110 can be made from a layer of thin silicone, biocompatible waterproof fibers or fabric, a medical curtain (e.g., a polypropylene curtain), treated paper, Tyvek®, and the like.

The disposable enclosure 1250a (e.g., the enclosure body 22110) defines a first hole 22120. The first hole 22120 is configured to operatively engage the probe and expose a portion of the probe that extends from the disposable enclosure 1250a through the first hole 22120. For example, the portion of the probe that is exposed includes the first end that has a concave surface configured to be adjacent to or to contact a scanning surface (e.g., on a head of a subject). The probe can be inserted through the hole 22120 to expose the portion of the probe.

In some arrangements, the first hole 22120 forms a seal around the probe when the disposable enclosure 1250a is attached, fastened, or otherwise coupled to the housing, and when the probe is inserted through the first hole 22120, exposing at least a portion of the probe. In one example, dimensions (e.g., a radius) of the first hole 22120 are smaller than corresponding dimensions (e.g., a radius) of the probe. A portion of the enclosure body 22110 surrounding the first hole 22120 forms the seal around the probe by providing a friction fit with the probe to prevent liquid and particles from entering into the cavity (e.g., such that liquids or particles cannot enter between the probe and the portion of the enclosure body 22110 that define the first hole 22120).

In some arrangements, the enclosure body 22110 further includes a first marker 22170 positioned to indicate (e.g., allowing an operator to recognize) that the first hole 22120 is for and corresponds to the probe, to facilitate the operator to insert the probe into the first hole 22120.

In some arrangements, the enclosure body 22110 includes at least one second hole (e.g., second holes 22130 and 22135) configured to receive a camera of the robotic pod 2106a, such that the camera protrudes from the at least one second hole when the disposable enclosure 1250a covers the housing. By providing at least two second holes 22130 and 22135, improved cost of production and utilization of the disposable enclosure 1250a can be realized. For instance, while the robotic pod 2106a has the camera on one side of the housing, another robotic pod 2106b positioned opposite to the robotic pod 2106a in the same robotic device 2102 may have a camera on an opposite side of the housing to collect data with respect to another side of subject's head. By providing the two second holes 22130 and 22135, the same disposable enclosure 1250a can be used for any type of device robotic pod 2106a or 2106b regardless of the position of the camera relative to the housing. In that regard, the second hole 22130 is configured to receive the camera (positioned at a first position relative to the housing), such that the camera protrudes from the second hole 22130 when the disposable enclosure 1250a is attached to the housing. The second hole 22135 is configured to receive a camera (positioned at a second position relative to the housing that is different from the first position), such that the camera protrudes from the second hole 22135 when the disposable enclosure 1250a is attached to the associated housing. Ambidextrous operations as well as mass production can thus be enabled based on a same design.

In some arrangements, the enclosure body 22110 further includes a second marker (e.g., second markers 22140 and 22145) positioned to indicate (e.g., allowing an operator to recognize) that a second hole (e.g., the second holes 22130 and 22135, respectively) is for and corresponds to the camera. The second markers 22140 and 22145 can indicate an orientation (e.g., "LEFT" or "RIGHT") of the camera relative to the housing, such that the operator can attach the disposable enclosure 1250a to the robotic pod 2106a in a corresponding and proper orientation.

The enclosure body 22110 forms an opening 22115 through which the robotic pod 2106a is placed within an interior volume of the enclosure body 22110. A fastening mechanism 22150 is provided for attaching, fastening, or otherwise coupling the disposable enclosure 1250a to the housing to allow easy installation and removal of the disposable enclosure 1250a and to provide secure placement of the disposable enclosure 1250a while on the robotic pod 2106a and while the robotic pod 2106a is operating. Although the fastening mechanism 22150 is shown to be an hair restraint configured to expand when being placed on the robotic pod 2106a and tighten around the robotic pod 2106a once the disposable enclosure 1250a is positioned, other examples of the fastening mechanism include but are not limited to, Velcro®, adhesive strips, adhesives, buttons, zippers, clamps, and strings. In other arrangements, the opening 22115 may not have any fastening mechanism coupled thereto such that the enclosure body 22110 simply drapes over the robotic pod 2106a.

In some arrangements, the enclosure body 22110 may have a substantially rectangular or square shape. Two pieces of material or a single sheet of material can be joined at edges 22160 and 22165 via adhesives to form the disposable enclosure 1250a. In other examples, a zipper, stitching, welding, or another suitable mating mechanism can be provided along the edges 22160 and 22165 for enclosing and sealing the enclosure body 22110 along the edges 22160 and 22165.

Although the various kits, items, and components have been described herein as being disposable, in other arrangements, the various kits, items, and components can be reusable and not necessarily disposable after a one-time use.

Although discrete examples and arrangements are illustrated and described herein, any given arrangement, or feature, component, design, and the like of the given arrangement, can be incorporated into another given arrangement described herein. As a non-limiting example, in some arrangements, a component of the disposable kit 100 can be incorporated into the disposable kit 1200 and vice versa.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

What is claimed is:

1. A kit containing items to be used with a medical device including a head cradle to support a head of a subject, the disposable kit comprising:
   a container, configured to enclose:
      a head cradle pad configured to fit a contour of the head cradle and couple to the head cradle, the head cradle pad being made from a flexible material, the head cradle pad having a first portion and a second portion, wherein the first portion has a thicker width than the second portion; and
      at least one fiducial marker configured to dispose on the head of the subject.

2. The kit of claim 1, wherein
   the items comprise at least the head cradle pad and the at least one fiducial marker; and
   the items are used for an ultrasound medical procedure.

3. The kit of claim 1, comprising a head restraint, wherein the head restraint pad is configured to releasably affix to the head restraint.

4. The kit of claim 2, wherein
   the head restraint pad comprises a pad layer and an adhesive layer; and
   the head restraint pad affixes to the head restraint via the adhesive layer.

5. The kit of claim 3, wherein:
   the pad layer of the head restraint pad is configured to be pressed into a concave surface of the head restraint; and
   the adhesive layer of the head restraint pad is configured to contact and adhere to the concave surface of the head restraint when the pad layer of the head restraint pad is pressed into the concave surface of the head restraint.

6. The kit of claim 1, wherein each of the at least one fiducial marker comprises:
   an adhesive surface that affixes to the subject; and
   a light reflective surface opposite to the adhesive surface.

7. The kit of claim 6, wherein the at least one fiducial marker comprises at least two fiducial markers.

8. The kit of claim 6, wherein the container further encloses a sheet, and wherein:
   the adhesive surface of each of the at least one fiducial marker is affixed to the sheet; and
   the at least one fiducial marker is configured to peel off of the sheet.

9. The kit of claim 1, wherein the at least one fiducial marker comprises a first set of fiducial markers and a second set of fiducial markers, each of the first set and the second set of fiducial markers comprising at least one fiducial marker configured to adhere to opposite sides of the head of the subject.

10. The kit of claim 9, wherein:
the first set of the fiducial markers comprises a first fiducial marker and a second fiducial marker;
the first fiducial marker is to be disposed at an edge of an eye of the subject; and
the second fiducial marker is to be disposed at a tragus of the subject.

11. The kit of claim 9, wherein the first set of fiducial markers comprises two fiducial markers and the second set comprises two other fiducial markers.

12. The kit of claim 11 wherein:
each of the first and second set of the fiducial markers is affixed to a single sheet via respective adhesive surfaces; and
each of the first and second set of fiducial markers peels off from the single sheet.

13. The kit of claim 1, wherein the head cradle pad is configured to contact a bottom surface of the container and fits into a space defined by the bottom surface and side walls extending from the bottom surface.

14. The kit of claim 13, comprising a head restraint pad, wherein the head cradle pad comprises a side portion shaped to define a space into which the head restraint pad fits when positioned between the side portion, the bottom surface of the container, and side walls of the container.

15. The kit of claim 1, further comprising a packaging that encloses the container.

16. The kit of claim 15, wherein the packaging seals the contents of the container from ingress of liquid or particles.

17. The container of claim 15, wherein the packaging comprises a strip of tape along any opening of the container.

18. The kit of claim 1, wherein the medical device comprises a Transcranial Doppler device.

19. A method for making a kit containing items configured for a medical device including a head cradle to support a head of a subject, the method comprising:
assembling a container, wherein the container is configured to enclose:
a head cradle pad configured to fit a contour of the head cradle and couple to the head cradle, the head cradle pad being made from a flexible material, the head cradle pad having a first portion and a second portion, wherein the first portion has a thicker width than the second portion; and
at least one fiducial marker to be disposed on the subject.

20. The method of claim 19, wherein the head restraint pad comprises a pad layer and an adhesive layer configured to affix to the head restraint.

* * * * *